(12) United States Patent
Cashman et al.

(10) Patent No.: US 8,481,501 B2
(45) Date of Patent: Jul. 9, 2013

(54) SYNTHESIS OF METABOLICALLY STABLE ANALGESICS, PAIN MEDICATIONS AND OTHER AGENTS

(75) Inventors: John R. Cashman, San Diego, CA (US); James M. Macdougall, La Jolla, CA (US)

(73) Assignee: Human BioMolecular Research Institute, San Diego, CA (US)

( * ) Notice: Subject to any disclaimer, the term of this patent is extended or adjusted under 35 U.S.C. 154(b) by 1269 days.

(21) Appl. No.: 11/628,132

(22) PCT Filed: May 31, 2005

(86) PCT No.: PCT/US2005/019000
§ 371 (c)(1),
(2), (4) Date: Mar. 29, 2010

(87) PCT Pub. No.: WO2005/117589
PCT Pub. Date: Dec. 15, 2005

(65) Prior Publication Data
US 2010/0190728 A1    Jul. 29, 2010

Related U.S. Application Data

(60) Provisional application No. 60/575,451, filed on May 28, 2004.

(51) Int. Cl.
*A01N 43/04* (2006.01)
*A61K 31/70* (2006.01)

(52) U.S. Cl.
USPC .......................................... 514/24; 536/122

(58) Field of Classification Search
None
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,845,770 A | 11/1974 | Theeumes et al. | |
| 3,916,899 A | 11/1975 | Theeumes et al. | |
| 4,008,719 A | 2/1977 | Theeumes et al. | |
| 5,013,556 A | 5/1991 | Woodle et al. | |
| 5,780,479 A * | 7/1998 | Kim | 514/282 |
| 6,323,212 B1 * | 11/2001 | Nagase et al. | 514/282 |
| 6,541,478 B1 | 4/2003 | O'Malley et al. | |
| 6,737,518 B1 | 5/2004 | Gutman et al. | |

OTHER PUBLICATIONS

O'Brien Science (1997), vol. 278, pp. 66-70.*
Ledgerwood et al. Addictive Behaviors (2002), vol. 27, pp. 483-491.*
Stachulski et al. Bioorganic & Medicinal Chemistry Letters (2003), vol. 13, pp. 1207-1214.*
Antonelli et al., *J Pharmacol & Exp Therapeutics* 307(2):651 (2003).
Benjamin et al., Brain Res 621:137-140 (1993).
Bollenback et al., *J Amer Chem Soc* 77:3310-3315 (1955).
Buchwald et al., *Surgery* 88:507 (1980).
Carrupt et al., *J Med Chem* 34: 1272-1275 (1991).
Cheng & Prusiff, *Biochem Pharmacol* 22:3099-3108 (1973).
Croop et al., *Arch Gen Psychiat* 54:1130-1135 (1997).
Czech & Bartsch, *J Org Chem* 49:4076-4078 (1984).
During et al., *Ann Neurol* 25:351 (1989).
Eckhardt et al., *FEBS Lett* 470:309-314 (2000).
Garbutt et al., *JAMA* 281:1318-1325 (1999).
Gellert & Holtzman, *J Pharmacol Exp Ther* 205:536-546 (1978).
Hanna et al., *Anesthesiology* 102:815-821 (2005).
He et al., *Cell* 108:271-282 (2002).
Howard et al., *J Neurosurg* 71:105 (1989).
Jaffe et al., *J Consult Clin Psychol* 64:1044-1053 (1996).
Keith et al., *Mol Pharm* 53:377-384 (1998).
Kelder et al., *Pharmaceutical Research* 16:1514-1519 (1999).
Kiefel et al., *J Carbohydr Chem* 18:937-959 (1999).
Kieffer et al., *Cell* 108:587-590 (2002).
Kranzler, *Am J Psychiat* 152:391-397 (1995).
Kuzuhara & Fletcher, *J Org Chem* 32:2531-2534 (1967).
Langer and Peppas, *J Macromol Sci Rev Macromol Chem* 23:61(1983).
Langer, *Science* 249:1527-1533 (1990).
Levy et al., *Science* 228:190 (1985).
Lewis et al., *J Am Chem Soc* 104:4976-4978 (1982).
MacDougall et al., *Bioorg Med Chem* 12:5983-5990 (2004).
MacDougall et al., *J Med Chem* 47:5809-5815 (2004).
MacDougall et al., *Bioorg Med Chem* 15:1583-1586 (2005).
Mason et al., *Arch Gen Psychiat* 56:719-724 (1999).
O'Brien et al., *Alcohol* 13:35-39 (1996).
Palm et al., *J Pharm Sci* 85:32-39 (1996a).
Pasternak, *Life Sci* 41:2845-2849 (1987).
Pasternak, *Clin Neuropharmacol* 16:1-18 (1993).
Penson et al., *Br J Clin Pharmacol* 53:347-354 (2002).
Postema et al., *Organic Lett* 5:1721-1723 (2003).
Portoghese et al., *J Med Chem* 31:1344-1347 (1987).
Rathke, *J Am Chem Soc* 92:3222-3223 (1970).
Saudek et al., *N Engl J Med* 321:574 (1989).
Schulteis et al., *Psychopharmacology* 129:56-65 (1997).
Sefton, *CRC Crit Ref Biomed Eng* 14:201 (1987).
Simon et al., *Synthetic Commun* 21:407-412 (1991).
Stachulski et al., *Bioorg Med Chem Lett* 13:1207-1214 (2003).
Stain-Texier et al., *Drug Metab Dispos* 26:383-387 (1998).
Stevens et al., *J Med Chem* 43:2759-2769 (2000).
Storck & Clarke, *J Am Chem Soc* 78:4619-4624 (1956).
Swift et al., *AM J Psychiat* 151:1463-1467 (1994).
Thomas et al., *J Med Chem* 47:1070-1073 (2004).
Tiedemann et al., *J Org Chem* 64:4030-4041 (1999).
Traynor & Nahorski, *Mol Pharmacol* 47:848-854 (1995).
Treat, In *Liposomes in the Therapy of Infectious Disease and Cancer*, Lopez-Berestein and Fidler eds., Liss, New York, pp. 353-365 (1989).

(Continued)

*Primary Examiner* — Patrick Lewis
(74) *Attorney, Agent, or Firm* — Edward D. Robinson; TechLaw LLP

(57) ABSTRACT

Disclosed are analgesic-related compositions and methods of using the compositions for modulation of analgesic receptor activity. The compositions and methods are useful for reducing pain, as well as for therapeutic intervention of addictions or other diseases or disorders amenable to treatment or prophylaxis by modulation of analgesic receptor signaling.

15 Claims, 21 Drawing Sheets

OTHER PUBLICATIONS

Ulm et al., *J Clin Psychiat* 56 (suppl. 7):5-14 (1995).
Volpicelli et al., *Arch Gen Psychiat* 54:737-742 (1997).
Walker et al., *Eur J Pharmacol* 383:115 (1999).
Wall et al., *Drug Metab Disposition* 9:369-375 (1981).
Wallace et al., *Tetrahedron Lett* 2693-2694 (1998).
Welsh, *J Org Chem* 19:1409 (1954).
Whistler et al., *Neuron* 23:737-746 (1999).
Zaveri et al., *Eur J Pharmacol* 428:29-36 (2001).

* cited by examiner

5: CH₂-2,3,4,6-tetra-O-benzyl-D-glucose
6a: CH₂-D-glucose
6b: pyridine-3-yl
6c: 3-dimethylaminophenyl
6d: 3-methoxyphenyl
6e: CH₂-thiophene-3-yl
6f: 3,5-dimethoxyphenyl
6g: 4-chlorophenyl
6h: 3-hydroxyphenyl

SYNTHESIS OF METABOLICALLY STABLE ANALGESICS, PAIN MEDICATIONS AND OTHER AGENTS

CROSS-REFERENCES TO RELATED APPLICATIONS

The present application claims priority to U.S. Provisional Patent Application No. 60/575,451, filed May 28, 2004, the entire disclosure of which is incorporated by reference herein.

FIELD OF THE INVENTION

The present invention pertains to pharmaceutical agents that interact with analgesic receptors, methods of preparing these agents, and their use for analgesia, pain, addictions, and other conditions.

BACKGROUND OF THE INVENTION

Morphine and other opiates act as powerful analgesics [Foye, W. O. in "*Principles of Medicinal Chemistry,*" Third Edition, Lea & Febiger, Philadelphia, 1989]. Considerable effort has been put forth to develop and understand the appropriate use of narcotic analgesics for terminal patients and for easing the pain of cancer, yet new medications are greatly needed. Morphine elicits a number of pharmacological activities mediated by mu opioid receptors, including analgesia, respiratory depression, and inhibition of gastrointestinal transit. [See O. Ray, "*Drugs, Society and Human Behavior,*" Third Edition, The C. V. Mosby Co., St. Louis (1983)]. However, adverse side effects and the abuse potential have limited morphine availability and optimal use. Solubility and potency issues limit the amount of injectable morphine as well. There is a need for longer-lived agents for severe pain. There is a need for agents that do not need to be administered by expensive i.v. or epidural routes of administration. There is also a need for medications that do not cause respiratory depression, tolerance, urinary retention, constipation, physical dependence, and/or addiction. In addition, some of the existing pain conditions are resistant to the analgesic action of currently available opiates. There is also a need for effective analgesics that only work in the periphery and do not enter the brain.

Tolerance is defined as a reduced sensitivity to the effect of an opiate and generally indicates an attenuation in analgesic efficacy causing dependence revealed by the physical manifestations of withdrawal. [See B. L. Kieffer et al., *Cell,* 108: 87-90 (2002).] Tolerance is almost exclusively associated with analgesia. It has been long thought that tolerance is caused by a reduction in surface receptors and opioid receptor signaling. However, morphine does not promote efficient mu receptor internalization, [see J. L. Whistler et al., *Neuron,* 23:737-46 (1999)] whereas other opioids such as the mu-selective peptide DAMGO and the alkaloid fentanyl do promote such internalization. In vitro models show that DAMGO administered at concentrations below the threshold for inducing internalization can induce internalization of the mu receptor in the presence of morphine. [See L. He et al., *Cell,* 108:271-82 (2002).] Analgesia following continuous administration of morphine is markedly enhanced when a sub-internalizing dose of DAMGO is co-administered to rats. [See L. He et al., supra.] This link between mu receptor internalization on the cellular level and tolerance in vivo suggests that receptor internalization may provide protection against tolerance. Determining which analogs of M6G effect receptor internalization may therefore be an important step to developing a non-addictive analgesic and furthering our understanding of the addiction process. Development of antagonists of the mu, delta, or kappa receptor also result in useful medications. Replacement of the N-17 methyl group in these M6G analogs with other alkyl, cycloalkyl and alkenyl groups could provide pharmacologically active antagonists at the opioid receptors. Such antagonists could be useful in treatment of diseases of the CNS including drug addiction, gambling addiction, and alcoholism. Elaboration of a derivative that is constantly charged and contains a quaternary amine or a guanadino group could also provide a new set of analgesics that only work in the periphery.

A major pathway for removing morphine and related opiates from the body is through the formation of water soluble glucuronide conjugates in the liver and subsequent excretion in the urine. In the case of morphine, three glucuronides are formed: morphine-6-β-D-glucuronide, morphine-3,3-D-glucuronide and morphine-3,6-di-β-D-glucuronide. Morphine-6-O-D-glucuronide (M6G) is an analgesic with a potency 100-fold greater than morphine itself. [See G. W. Pasternak, *Life Sci.,* 41:2845-2849 (1987).] The low bioavailability (11%) of M6G due to hydrolysis in the gut by stomach acid is a significant limitation in the development of a drug from this compound. [See R. T. Penson et al., *Br. J. Clin. Pharmacol.,* 53:347-354 (2002).] Development of new medications based upon M6G is promising because of its analgesic potency, favorable side effect profile, and distinct pharmacological activity. [See M. H. Hanna et al., *Anesthesiology,* 102:815-821 (2005).]

Glucuronides as a rule are thought to be highly polar metabolites and unable to cross the blood brain barrier (BBB). [See G. W. Pasternak, *Clin. Neuropharmacol.,* 16:1-18 (1993).] However, M6G is apparently much more lipophilic than predicted. [See P. A. Carrupt et al., *J. Med. Chem.,* 34:1272-1275 (1991).] Polar surface area (PSA) calculations suggest molecules above 90 Å$^2$ do not get into the brain. [See K. Palm et al., *J. Pharm. Sci.,* 85:32-39 (1996a).] For BBB penetration via the transcellular route a molecule should have a MW of <450 and a PSA<90 Å$^2$. Related calculations show that oral absorption is optimal with a PSA<120 Å$^2$. [See J. Kelder et al., *Pharmaceutical Research,* 16:1514-1519 (1999).] In rats, after oral administration, M6G was absorbed per se in the proximal intestine, showing that M6G is capable of membrane penetration. [See R. Stain-Texier et al., *Drug Metab. Dispos.,* 26:383-387, (1998).] But analogs of M6G with a molecular weight greater than 450 are predicted to not get into the brain, and because of the more polar nature compared to morphine, are predicted by others to not have more favorable CNS biodistribution and onset of action properties.

BRIEF SUMMARY OF THE INVENTION

In one aspect, the present invention provides analgesic-related agents having pharmacological activity against analgesic receptors. In typical embodiments, the agents comprise an analgesic or derivative thereof linked to an optionally substituted aryl, optionally substituted heteroaryl, or a saccharide. In preferred embodiments, the analgesic or derivative thereof is an opiate or an opiate derivative. The analgesic-related agent can be an agonist or an antagonist of a corresponding analgesic receptor to which the agent specifically binds.

The agents of the present invention are useful, for example, for reducing pain in a subject, or for the treatment or prophylaxis of a disease or disorder amenable to such treatment or prevention by modulation (e.g., inhibition or stimulation) of analgesic receptors. Accordingly, in another aspect, the present invention provides pharmaceutical compositions comprising an analgesic-related agent as set forth herein. Also provided are methods for reducing pain, or for treating or preventing a disease or disorder amenable to such treatment or prevention by modulation of analgesic receptor activity, by administration of an effective amount of an analgesic-related agent to a subject. Diseases or disorders amenable to therapeutic intervention in accordance with the compositions and methods provided herein include, for example, addictions or other disorders of the CNS that are mediated, at least in part, directly or indirectly, by analgesic receptors. In certain variations of the pharmaceutical compositions or methods, such as, e.g., for the treatment of pain, the analgesic-related agent is an analgesic receptor agonist. In other embodiments, such as, e.g., for the treatment of drug addiction, gambling addiction, or alcoholism, the agent is typically an analgesic receptor antagonist.

For modulation of analgesic receptors in the periphery, without significant effect on such receptors in the brain, the agent is typically has a constant charge at physiological pH. Such agents can include, for example, quaternary amines, quanidines, and the like, and are particularly suitable for use as, e.g., peripheral analgesics.

DEFINITIONS

Unless defined otherwise, all technical and scientific terms used herein have the same meaning as commonly understood by one of ordinary skill in the art to which this invention belongs. Although any methods and material similar to those described herein can be used in the practice or testing of the present invention, only exemplary methods and materials are described. For purposes of the present invention, the following terms are defined below.

The terms "a," "an," and "the" include plural referents unless the context clearly dictates otherwise.

The term "alkyl" refers to saturated aliphatic groups including straight chain, branched chain, and cyclic groups, all of which may be optionally substituted. Suitable alkyl groups include methyl, ethyl and the like, and may be optionally substituted.

The term "alkenyl" refers to unsaturated groups which contain at least one carbon-carbon double bond and includes straight chain, branched chain, and cyclic groups, all of which may be optionally substituted.

The term "alkynyl" refers to unsaturated groups which contain at least one carbon-carbon triple bond and includes straight chain, branched chain, and cyclic groups, all of which may be optionally substituted. Suitable alkynyl groups include ethynyl, propynyl, butynyl and the like which may be optionally substituted.

The term "aryl" refers to aromatic groups which have at least one ring having conjugated "pi" electron system and includes carbocyclic aryl, biaryl, both of which may be optionally substituted.

The term "aralkyl" refers to an alkyl group substituted with an aryl group. Suitable aralkyl groups include benzyl, and the like, and may be optionally substituted.

The term "heteroaryl" refers to carbon containing 5-14 membered cyclic unsaturated radicals containing one, two, three, or four O, N, P, or S atoms and having 6, 10 or 14 $\pi$ electrons delocalized in one or more than one rings.

The term "pharmaceutically acceptable derivative" refers to any derivative of a compound as described herein that is suitable for pharmacological use, including, e.g., pharmaceutically acceptable esters, amides, or salts. Pharmaceutically acceptable esters, amides, or salts" refers to esters, amides, or salts derived from the combination of a compound of this invention and an organic or inorganic acid.

The term "analgesic" refers to a compound capable of producing analgesia, i.e., reducing or inhibiting pain by altering perception of nociceptive stimuli without producing anesthesia or loss of consciousness. In preferred embodiments of the present invention, an analgesic is an opiate.

The terms "opiate" and refers to any agent, natural or synthetic, capable of specifically binding to an opioid receptor, including opium or any of its derivatives (e.g., morphine), as well as synthetic or semi-synthetic narcotics.

The term "analgesic-related agent" refers to a metabolite, analog, or derivative of an analgesic. The term "opiate-related agent" refers to a metabolite, analog, or derivative of an opiate, such as further described herein. In accordance with the present invention, analgesic-related agents, including opiate-related agents, can have agonist or antagonist activity with respect to one or more analgesic receptors to which the agent specifically binds.

The term "inhibit" means to reduce by a measurable amount, or to prevent entirely.

The phrase "promote efficient receptor internalization" means that an agent is capable of promoting cellular internalization of a receptor to which the agent specifically binds such that, as compared to control cells not contacted with the agent, cells contacted with the agent display no more that 80%, typically no more than 70% or 60%, and more typically no more than 50% or 40%, of surface staining for the corresponding receptor by FACS.

"Treating," "treatment," or "therapy" of a disease or disorder means slowing, stopping, or reversing progression of the disease or disorder, as evidenced by a reduction or elimination of either clinical or diagnostic symptoms, using the compositions and methods of the present invention as described herein.

"Preventing," "prophylaxis," or "prevention" of a disease or disorder means prevention of the occurrence or onset of a disease or disorder or some or all of its symptoms.

"Addiction" as used herein refers to a disease or disorder characterized by a habitual psychological and physiologic dependence on a substance or practice that is substantially beyond voluntary control. Addictions amenable to treatment using the compounds and methods described herein include substance addictions such as, e.g., addictions to narcotics (e.g., morphine, heroin), alcohol, and nicotine, as well as behavioral addictions such as, e.g., addiction to gambling.

The term "subject" as used herein means any mammalian patient to which the compositions of the present invention may be administered according to the methods described herein. Subjects specifically intended for treatment or prophylaxis using the methods of the present invention include humans.

The term "therapeutically effective regime" means that a pharmaceutical composition or combination thereof is administered in sufficient amount and frequency and by an appropriate route to reduce pain, or to at least detectably prevent, delay, inhibit, or reverse development of at least one symptom or biochemical marker of a disease or disorder amenable to treatment by modulation of an analgesic receptor.

The term "therapeutically effective amount" refers to an amount of an agent of the present invention, or a combination of an agent of the present invention with other agent(s), that is present to achieve a desired result, e.g., reducing pain, or preventing, delaying, inhibiting, or reversing a symptom or biochemical marker of a disease or disorder amenable to treatment by modulation of an analgesic receptor, when administered in an appropriate regime.

DETAILED DESCRIPTION

Figure 1:
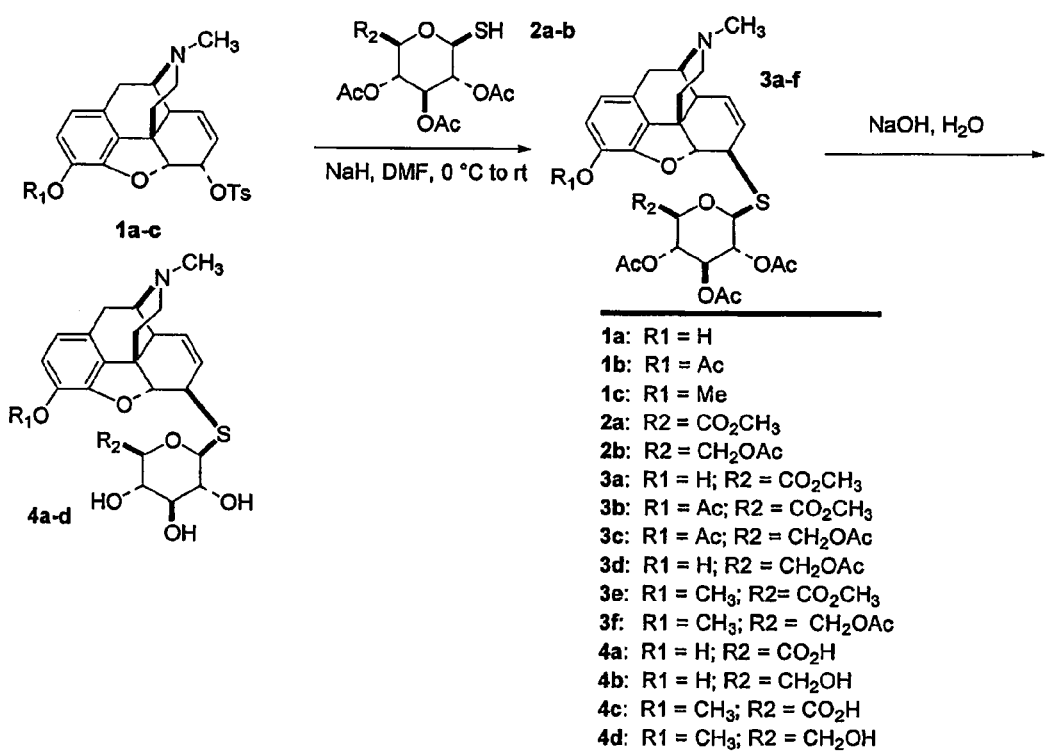
FIG. 1 depicts the synthesis of compounds represented by Formula IV.

The present invention pertains to analgesics and analgesic derivatives, particularly opiate-related compounds. The structure, synthesis, and biological evaluation of these compounds are described herein, as well as pharmaceutical compositions comprising these compounds and their pharmacological use such as, e.g., for treatment of pain and substance addiction. In certain embodiments, the compounds described herein are related to the morphine metabolite M6G. Unexpectedly, analogues unrelated to M6G possessed more favorable pharmacological properties than M6G in several functional in vitro and in vivo tests.

In vitro pharmacological and metabolic studies and animal models of different components of analgesic receptor signaling and substance addiction can predict medications development that will be effective in different components of a human model in the treatment of pain and substance addiction. Using a dynamic medicinal chemistry feedback from the in vitro and in vivo components, both of which streamline information to facilitate ultimate medications development, compounds useful for, e.g., treatment of pain and/or addiction have been identified. Pharmacological activity of these compounds in one or more components of the addiction cycle provides, inter alis, a basis for combination therapies such that multiple components of the addiction cycle can be covered by a given pharmacological agent.

For purposes of setting forth embodiments of the present invention, it is understood that the chemical formulas described herein include pharmaceutically acceptable derivatives of the respective compounds, including salts, esters, and amides, as well as all possible stereochemical arrangements of substituents, including racemic or stereo chemically pure compounds.

Compounds

In one aspect of the present invention, compounds are provided having pharmacological activity against analgesic receptors and which are useful for, e.g., the treatment of pain or diseases or disorders amenable to treatment via modulation of such receptors, including addictions. Compounds of the present invention generally have the following Formula I:

A-B—C (I)

where A is an analgesic or derivative thereof, B is a linking group, and C is selected from the group consisting of optionally substituted aryl, optionally substituted heteroaryl, and a saccharide; and all pharmaceutically acceptable derivatives thereof. In preferred variations, the analgesic A is an opiate. Opiates particularly suitable for use in accordance with the invention described herein include, for example, naltrexones, phenyl piperidines, piperidinols, prodines, piperidyl propionanilides, isoprodines, prodilidines, benzomorphans, morphans, azabicyclanes, morphinans, prodines, diphenylaminoethylpropionates, methadones, isomethadones, propoxyphenes, dextromethorphans, benzazocin-8-ols, norbinaltrophines, naltrindoles, and guanidinenaltrindoles. The linking group B can be, for example, —S— or —NH(CO)(CH$_2$)$_n$—, where the subscript n is an integer of from 0 to 5.

In certain embodiments, C is aryl or heteroaryl, optionally substituted with halogen, (C$_1$-C$_5$)alkoxy, nitro, or CO$_2$R, where R is H or (C$_1$-C$_5$)alkyl. In specific embodiments, C is, e.g., phenyl, thiophene, or a saccharide. Particularly suitable saccharides are those having the following Formula II:

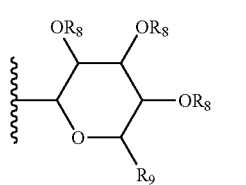

(II)

where each R$_8$ is independently H, (C$_1$-C$_5$)alkylC(O)—, (C$_7$-C$_{10}$)aralkylC(O)—, (C$_7$-C$_{10}$)aralkyl, (C$_6$-C$_{12}$)aryl, or (C$_6$-C$_{12}$)aryl(CO)—; R$_9$ is CH$_2$OH, CH$_2$O(C$_1$-C$_5$)alkyl, CH$_2$O$_2$C(C$_1$-C$_5$)alkyl, CH$_2$O(C$_7$-C$_{10}$)aralkyl, CH$_2$O(C$_6$-C$_{12}$)aryl, CO$_2$H, CO$_2$(C$_1$-C$_5$)alkyl, CO$_2$(C$_6$-C$_{12}$)aryl, or CO$_2$(C$_7$-C$_{10}$)aralkyl; and the wavy line indicates the point of attachment to the rest of the molecule.

In one suitable variation, the compound has the following Formula III:

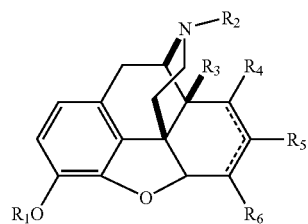

(III)

where the dashed line indicates a single, double, or normalized bond; R$_1$ is H, (C$_1$—O$_5$)alkylC(O)—, (C$_7$-C$_{10}$)aralkylC(O)—, (C$_7$-C$_{10}$)aralkyl, (C$_1$-C$_5$)alkyl, (C$_6$-C$_{12}$)aryl, (C$_6$-C$_{12}$)aryl(CO)—, or silyl; R$_2$ is (C$_1$-C$_5$)alkyl, (C$_3$-C$_6$)cycloalkyl, (C$_3$-C$_6$)cycloalkyl-alkyl, (C$_5$-C$_7$)cycloalkenyl-alkyl, (C$_6$-C$_{12}$)aryl, (C$_7$-C$_{12}$)aralkyl, (C$_6$-C$_{12}$)heteroaryl, (C$_7$-C$_{12}$)heteroaralkyl, (C$_2$-C$_5$)alkenyl, (C$_2$-C$_5$)alkynyl, optionally substituted with a substituent selected from the group consisting of halogen, (C$_1$-C$_5$)alkoxy, nitro, or CO$_2$R, where R is H or (C$_1$-C$_5$)alkyl; R$_3$ is H or OH; R$_4$ is H; R$_5$ is H or is combined with R$_6$ to form a heteroaryl group substituted with YR$_7$; R$_6$ is YR$_7$ or is combined with R$_5$ to form a heteroaryl group substituted with YR$_7$; Y is —S— or —NH(CO)(CH$_2$)$_n$—, where the subscript n is an integer of from 0 to 5; and R$_7$ is an optionally substituted aryl, optionally substituted heteroaryl, or a saccharide, the saccharide having Formula II as set forth above. Particularly suitable R$_2$ groups include, for example, cyclopropylmethyl, cyclobutylmethyl, and allyl.

In some alternative embodiments, the compound has the following Formula IVa or IVb:

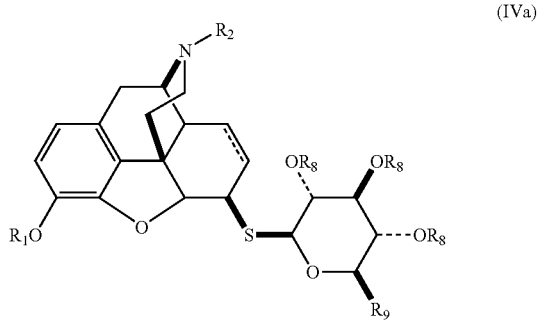

where R$_1$ is H, (C$_1$-C$_5$)alkylC(O)—, (C$_1$-C$_{10}$)aralyl, or (C$_1$-C$_5$)alkyl; R$_2$ is (C$_1$-C$_5$)alkyl, C$_3$-C$_6$(cycloalkyl)alkyl, C$_5$-C$_7$ (cycloalkenyl)alkyl, (C$_6$-C$_{12}$)aryl (C$_7$-C$_{12}$)aralkyl, trans(C$_4$-C$_5$)alkenyl, allyl, or furan-2-ylalkyl; each R$_8$ is independently H, (C$_1$-C$_5$)alkylC(O), (C$_7$-C$_{10}$)aralylC(O), (C$_7$-C$_{10}$)aralyl, or (C$_1$-C$_5$)alkyl; and R$_9$ is CH$_2$OH, CH$_2$O$_2$C(C$_1$-C$_5$)alkyl, CH$_2$O(C$_7$-C$_{10}$)aralkyl, CO$_2$H, CO$_2$(C$_1$-C$_5$)alkyl, or CO$_2$(C$_7$-C$_{10}$)aralkyl.

In yet another variation, the compound has the following Formula Va or Vb:

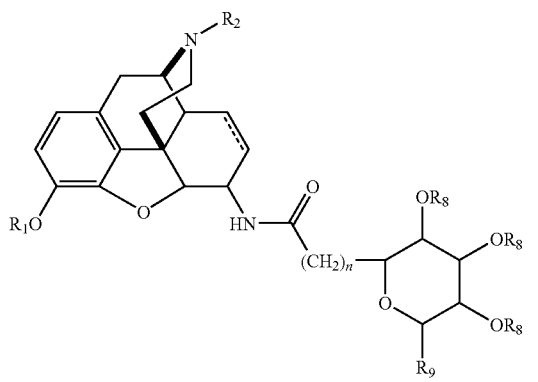

(Vb)

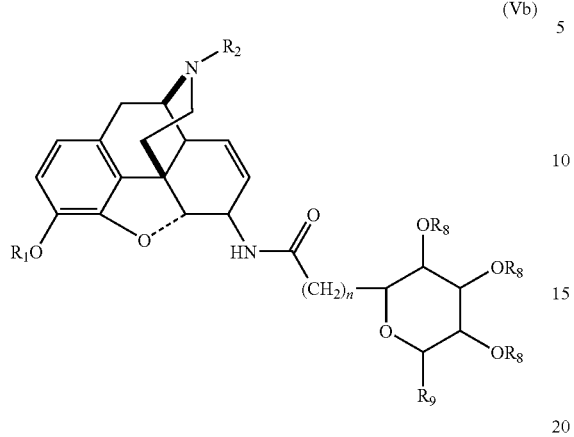

(VII)

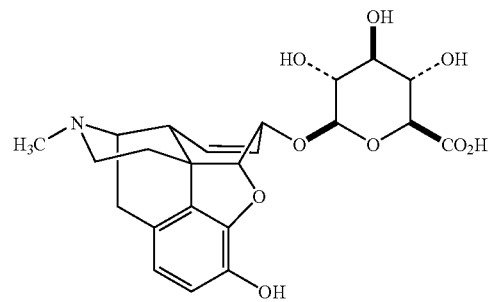

where $R_1$ is H, $(C_1\text{-}C_5)$alkylC(O)—, $(C_1\text{-}C_{10})$aralyl or $(C_1\text{-}C_5)$alkyl; $R_2$ is $(C_1\text{-}C_5)$alkyl, $C_3\text{-}C_6$(cycloalkyl)alkyl, $C_5\text{-}C_7$ (cycloalkenyl)alkyl, $(C_6\text{-}C_{12})$aryl $(C_7\text{-}C_{12})$aralkyl, trans$(C_4\text{-}C_5)$alkenyl, allyl or furan-2-ylalkyl; $R_8$ is independently H, $(C_1\text{-}C_5)$alkylC(O), $(C_7\text{-}C_{10})$aralylC(O), $(C_7\text{-}C_{10})$aralyl, or $(C_1\text{-}C_5)$alkyl, $R_9$ is $CH_2OH$, $CH_2O_2C(C_1\text{-}C_5)$alkyl, $CH_2O(C_7\text{-}C_{10})$aralyl, $CO_2H$, $CO_2(C_1\text{-}C_5)$alkyl or $CO_2(C_7\text{-}C_{10})$ aralkyl; and the subscript n is an integer of from 0 to 5.

In still other embodiments, the compound has the following Formula VIa or VIb:

(VIa)

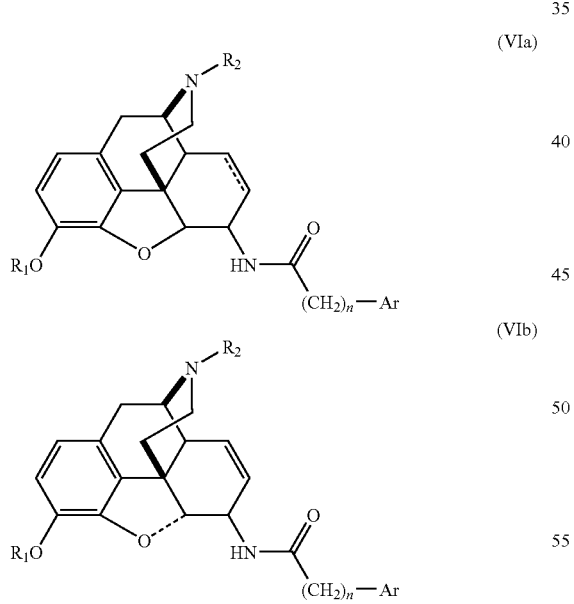

(VIII)

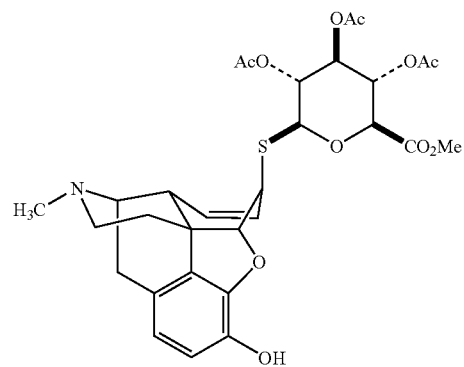

(VIX)

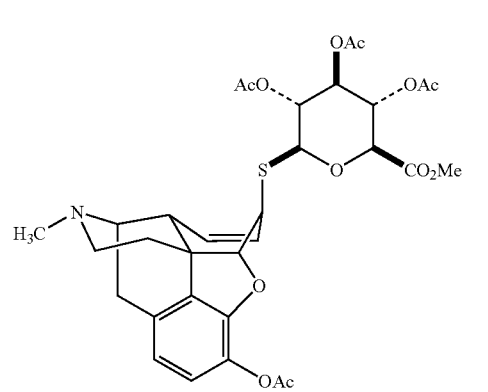

(VIb)

(X)

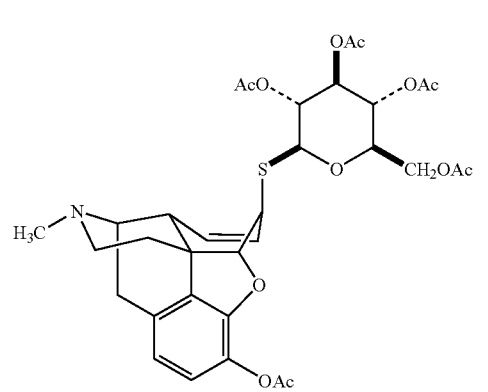

where $R_1$ is H, $(C_1\text{-}C_5)$alkylC(O)—, $(C_7\text{-}C_{10})$aralyl, or $(C_1\text{-}C_5)$alkyl; $R_2$ is $(C_1\text{-}C_5)$alkyl, $C_3\text{-}C_6$(cycloalkyl)alkyl, $C_5\text{-}C_7$ (cycloalkenyl)alkyl, $(C_6\text{-}C_{12})$aryl $(C_7\text{-}C_{12})$aralkyl, trans$(C_4\text{-}C_5)$alkenyl, allyl, or furan-2-ylalkyl; and the subscript n is an integer of from 0 to 5.

In specific embodiments, the compound of the present invention has any one of the following Formulas VII through XXX:

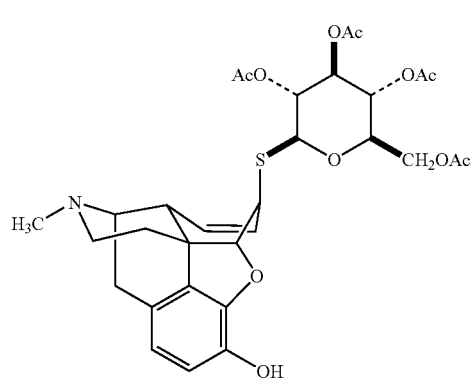
(XI)
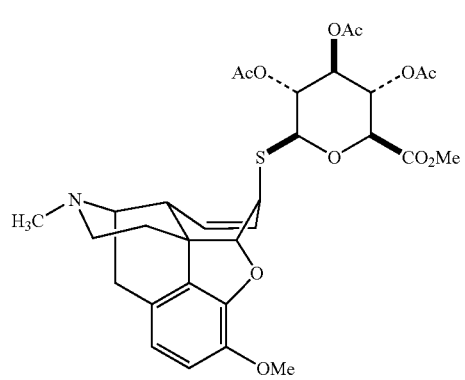
(XII)
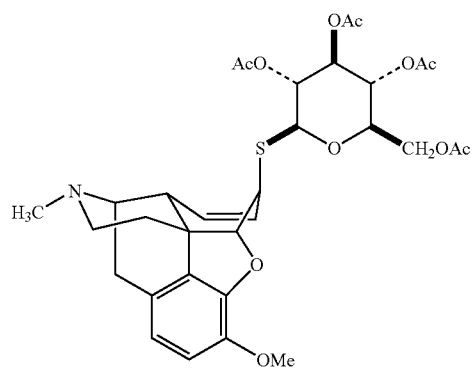
(XIII)
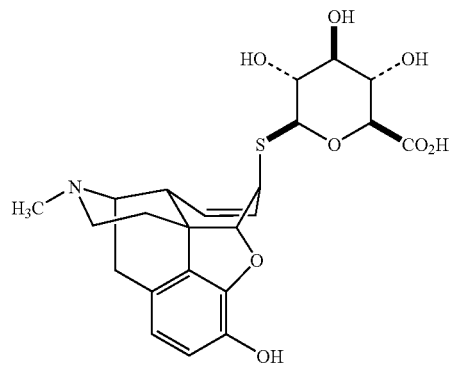
(XIV)
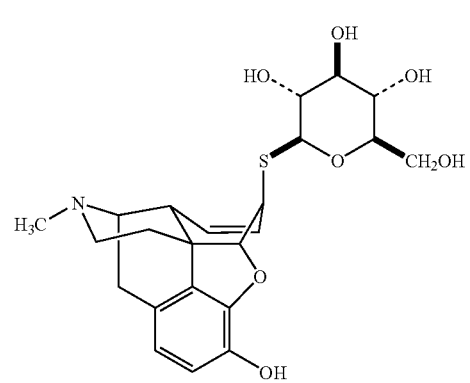
(XV)
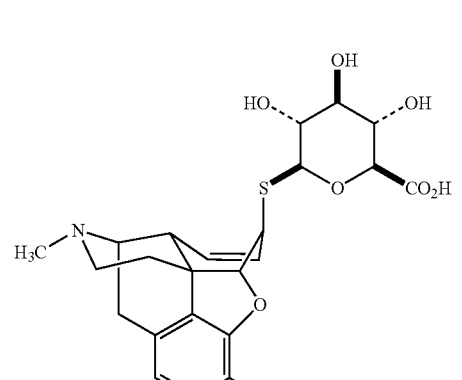
(XVI)
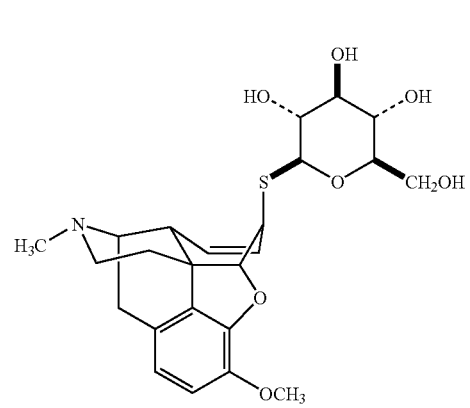
(XVII)
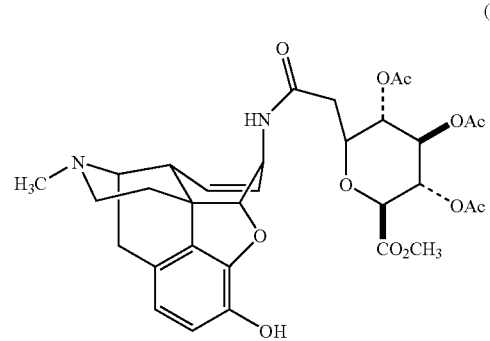
(XVIII)

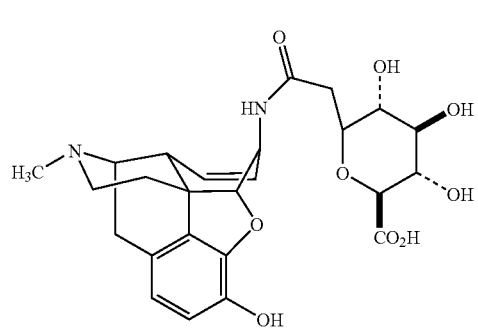
(XIX)
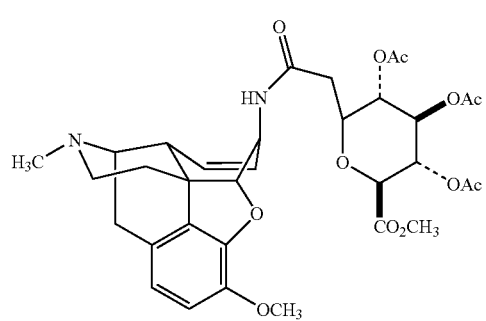
(XX)
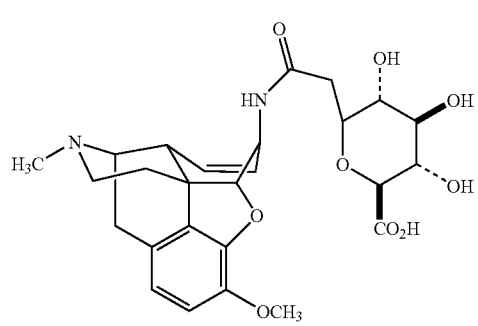
(XXI)
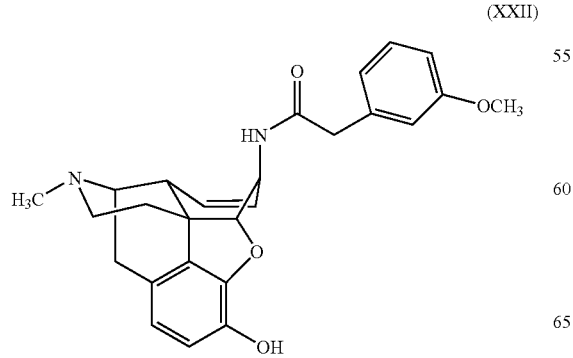
(XXII)
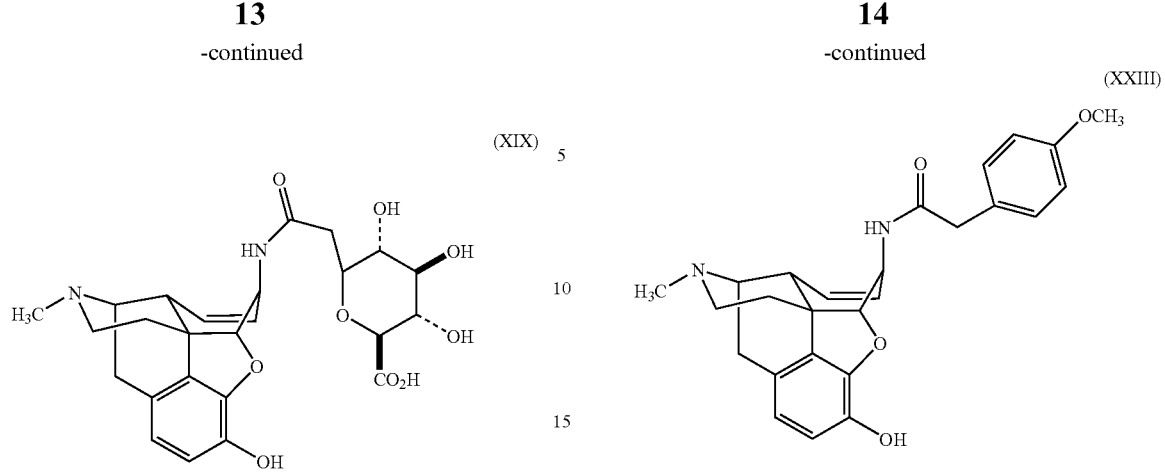
(XXIII)
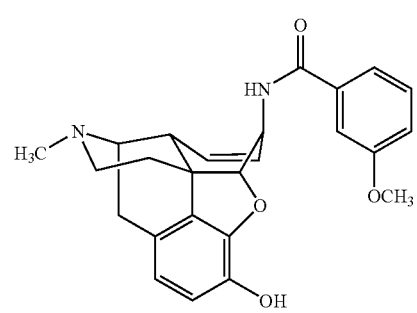
(XXIV)
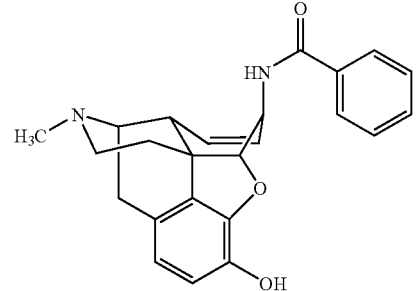
(XXV)
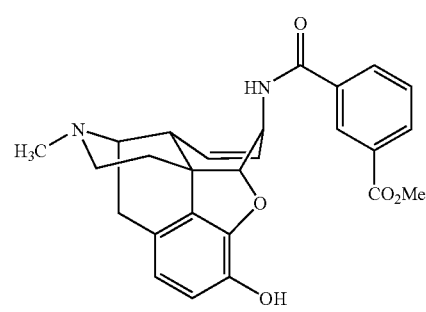
(XXVI)
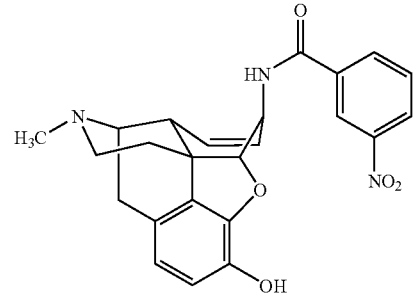
(XXVII)

-continued

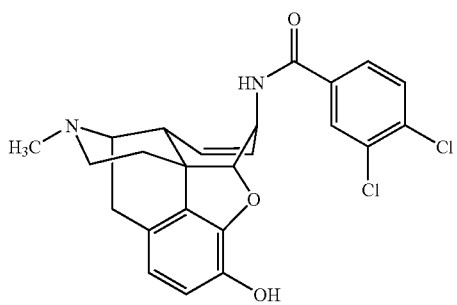

(XXVIII)

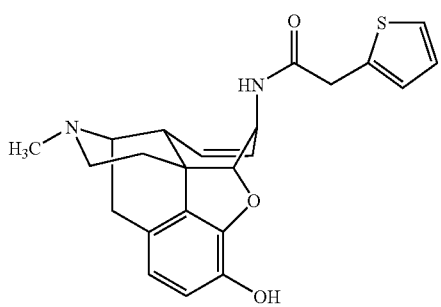

(XXIX)

and

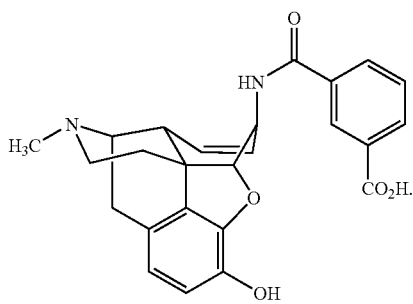

(XXX)

Other Embodiments

In certain embodiments, compounds of the present invention include morphine, dihydromorphine-6-glucuronide, codeine, and dihydrocodeine-6-glucuronide sulfur analogues having the following Formula IV:

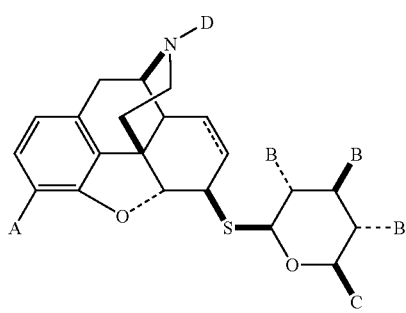

(IV)

wherein A is OR, OH, or OC(O)R; B is OC(O)R, OH, or OR; C is $CO_2R$, $CO_2H$, $CH_2OR$, or $CH_2OH$; D is alkyl, cycloalkyl, alkenyl, alkynyl, optionally substituted aryl, or optionally substituted aralkyl; and R in the substituents A, B, C, D is an alkyl or aryl group.

In other embodiments, compounds of the present invention include the codeine, dihydrocodeine, morphine, and dihydromorphine analogues having the following Formula V:

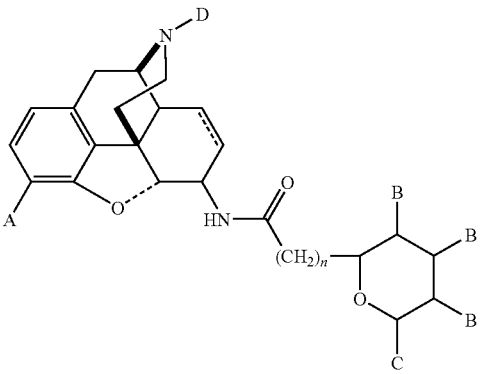

(V)

where A is RO, OH, or OC(O)R; B is OC(O)R, OH, or OR; C is $CO_2R$, $CO_2H$, $CH_2OR$, or $CH_2OH$; D is alkyl, cycloalkyl, alkenyl, alkynyl, optionally substituted aryl, or optionally substituted aralkyl; and R in the substituents A, B, C, D is an alkyl or aryl group.

In yet other variations, compounds of the present invention include the morphine, dihydromorphine, codeine, and dihydrocodeine amides of the following Formula VI:

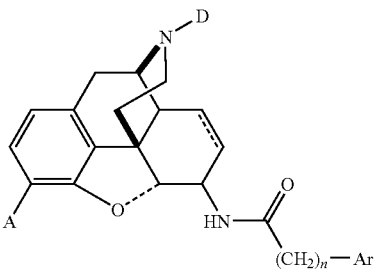

(VI)

where A is RO, OH, or OC(O)R, where n is an integer from 0-5; aryl is phenyl, 3,4-dichlorophenyl, 3-methoxyphenyl, 4-methoxyphenyl, 3-nitrophenyl, 3-carbomethoxyphenyl, 3-carboxyphenyl or thiophen-2-yl, or an optionally substituted aryl or heteroaryl derivative; D is alkyl, cycloalkyl, alkenyl, alkynyl, optionally substituted aryl, or optionally substituted aralkyl; and R in the substituents A and D is each independently an alkyl or aryl group.

Figure 2:
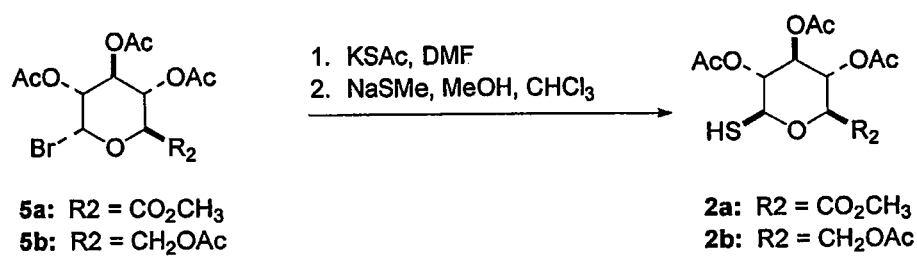
FIG. 2 depicts the synthesis of thiosaccharides 2a and 2b.

The compounds of Formula IV can be synthesized by the $S_N2$ reaction of the 6β-tosylates of morphine, 3-O-acetylmorphine and codeine 1a-c with the sodium salts of the thiosaccharides 2a-b in dimethylformamide (see FIG. 1) giving 3a-f. For the preparation of the starting tosylates, [see L. H. Welsh, *J. Org. Chem.*, 19:1409 (1954); G. Stork and F. Clarke, *J. Am. Chem. Soc.*, 78:4619-4624 (1956)]. The ester protecting groups are subsequently removed by stirring overnight in aqueous sodium hydroxide to provide additional compounds which are the S-β-D-glucuronides or S-β-D-glucose conjugates of morphine, codeine and their congeners 4a-d. The thiosaccharides 2a-b used in these preparations were made by the reaction of the corresponding glycosyl bromides with potassium thioacetate followed by selective S-deacetylation with sodium thiomethoxide (see FIG. 2). [See G. N. Bollenback et al., *J. Org. Chem.*, 77:3310-3315 (1955)] for the preparation of the starting glycosyl bromides. [See Wallace et al., *Tetrahedron Lett.*, 2693-2694 (1998)] for a related S-deacetylation. This synthetic methodology constitutes a general synthetic route for the attachment of saccharides to morphine, codeine and their N-17 derivatives at the C-6 position via a sulfur atom and is applicable to the preparation of the dihydromorphine and dihydrocodeine derivatives of these compounds. In addition, utilizing the 6β-tosylates of morphine, codeine and derivatives allows for the preparation of the C-6α derivatives of all compounds mentioned above.

Figure 3:
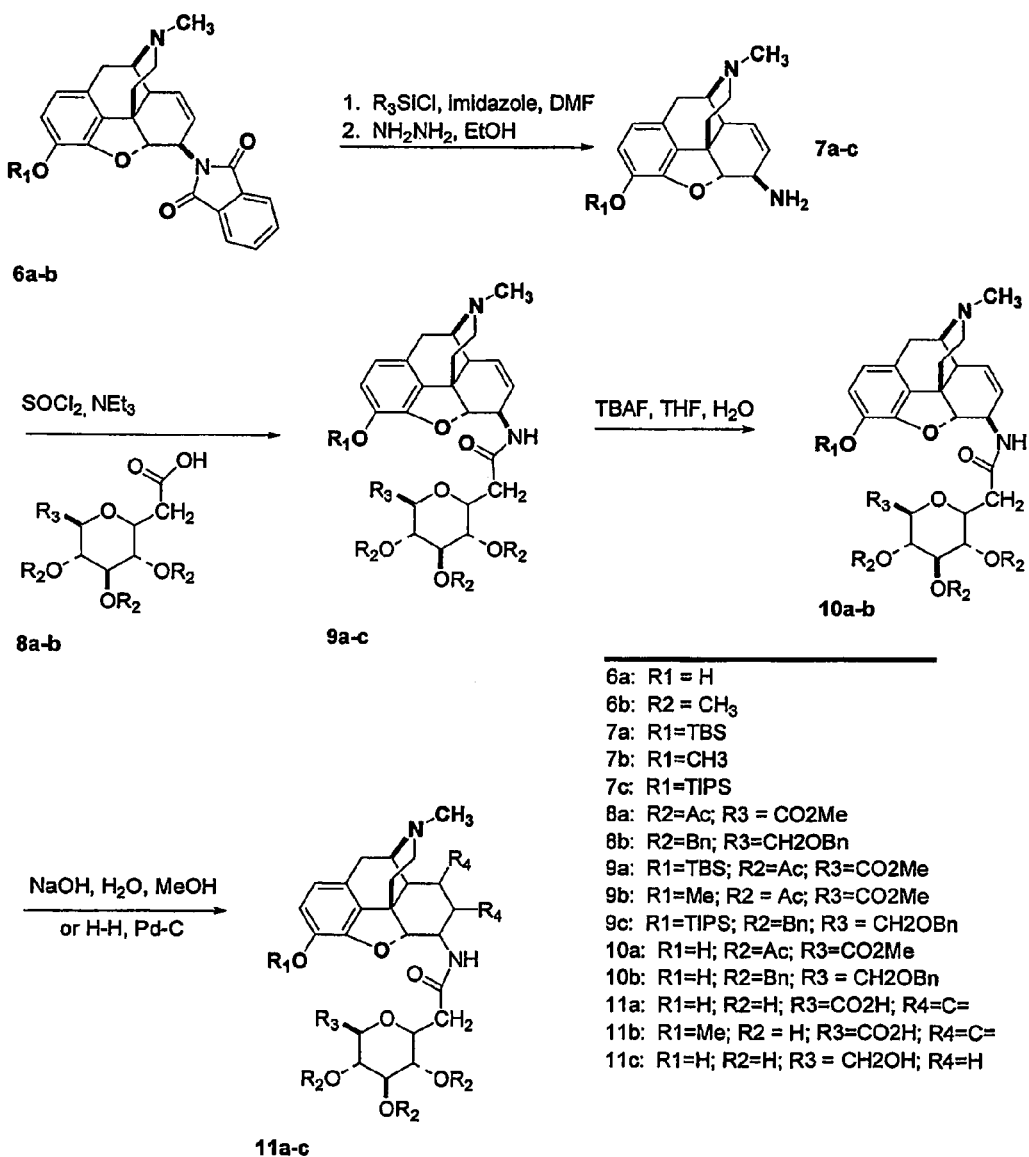
FIG. 3 depicts the synthesis of compounds of Formula V.

The compounds of Formula V can be synthesized from the 6β-phthalimides of morphine, dihydromorphine, codeine, dihydrocodeine and their N-alkyl and cycloalkyl derivatives 6 (see FIG. 3). [See S. Makleit et al., *Synthetic Commun.*, 21:407-412 (1991).] For compounds in the morphine series the phenolic hydroxyl group is protected as a silyl ether by the reaction with tert-butyldimethylsilylchloride or triisopropylsilylchloride and imidazole in room temperature dimethylformamide. The phthalimide group is then removed by heating with hydrazine hydrate in EtOH to give the amines 7. The amines 7 are reacted with the acid chloride of C-glycosides 8 giving the amides 9. When the R1 in 9 is a silyl ether it can be removed by treatment with TBAF to give the phenols 10. The sugar protecting groups in 9 or 10 are removed by treatment with aqueous NaOH or by hydrogenation giving compounds II. The C-glycosides 8 used in these syntheses were prepared by known methods [M. Lewis et al., *J. Am. Chem. Soc.*, 104:4976-4978 (1982)]. This synthetic sequence provides a general route for the attachment of saccharides to morphine and their N-17 derivatives at the C-6 position via an amide bridge and is applicable to the preparation of the dihydromorphine and dihydrocodeine derivatives of these compounds.

Figure 4:
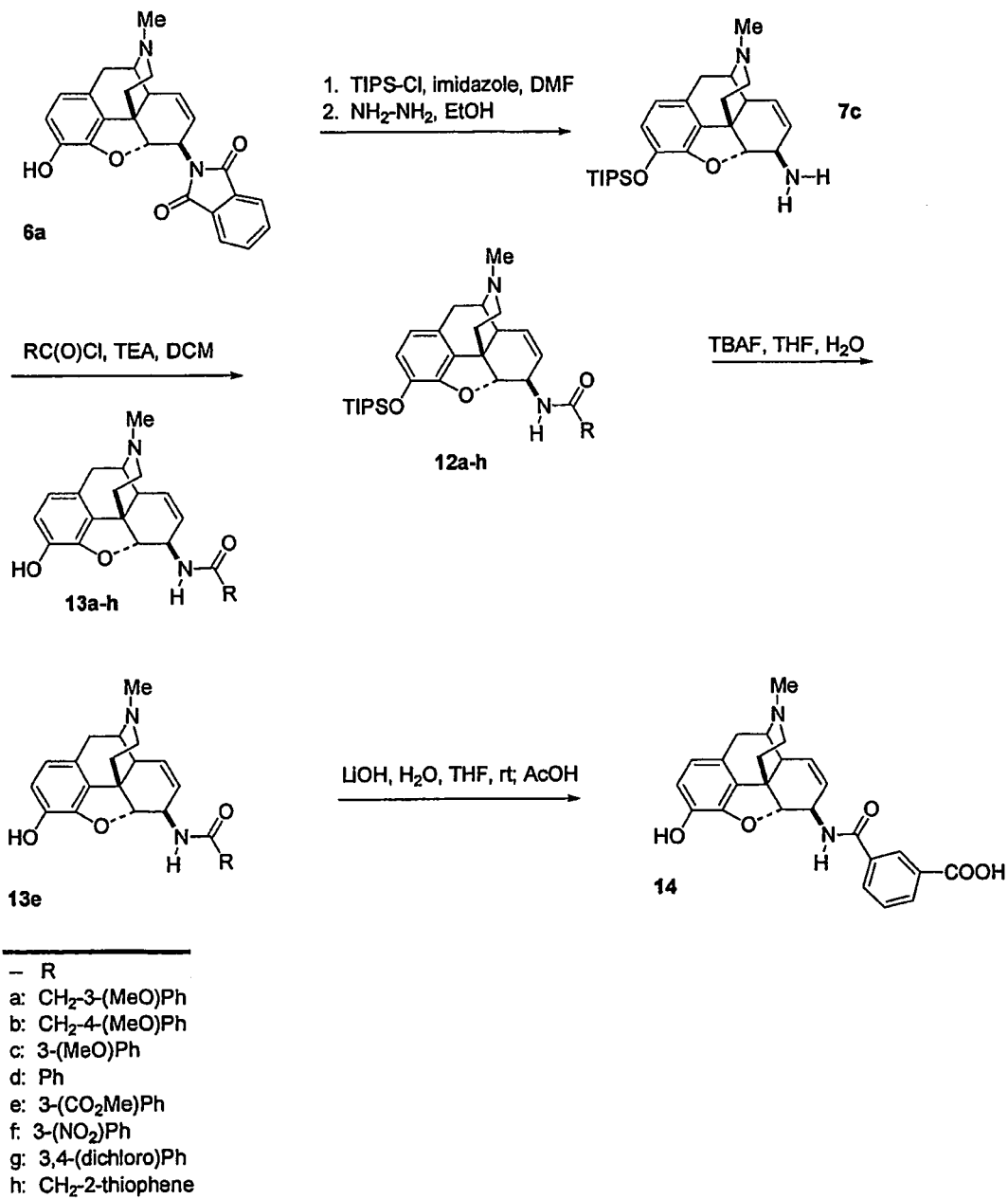
FIG. 4 depicts the synthesis of compounds of Formula VI.

The compounds of Formula VI can be synthesized from the 6β-aminomorphine 7c (see FIG. 4) used in the preparation of compounds of Formula V. The amine 7c is treated with aryl and heteroaryl acid chlorides to give the amides 12a-h. The treatment of 12a-h with TBAF in aqueous THF provides the 6β-amidomorphines 13a-h. Treatment of the methyl ester 13e with aqueous sodium hydroxide provide the carboxylic acids 14. This synthetic sequence provides a general route for the attachment of aryl and heteroaryl substituents to morphine, codeine and their N-17 alkyl derivatives at the C-6 position via an amide bridge and is applicable to the preparation of the dihydromorphine and dihydrocodeine derivatives of these compounds. This synthetic methodology also provides for the preparation of the C-6a derivatives of all of the above compounds by starting with the C-6 epimer of the amine 7c. Replacement of the N-methyl substituent of the bridgehead N for the compounds described herein with cyclopropyl methyl or cyclobutyl methyl or similar substituents will typically afford antagonists of the receptors for the activity described below. Such antagonists are useful for antagonizing drug addiction, gambling addiction, alcoholism, or other diseases of the CNS. Further, application of the synthetic methodology described herein (attachment of metabolically stable saccharides or their chemical homologues or isosteric equivalents) to other analgesics including naltrexone, phenyl piperidines, piperidinols, prodines, piperidyl propionanilides, isoprodines, prodilidines, benzomorphans, morphans, azabicyclanes, morphinans, prodines, diphenylaminoethylpropionates, methadones, isomethadones, propoxyphenes, dextromethorphans, benzazocin-8-ols, and all related stereoisomers and N-substituted derivatives (cyclopropyl methyl, cyclobutylmethyl, allyl, and the like) will lead to pharmacologically active CNS agents useful for reducing pain, as well as for the treatment of addiction and other diseases.

In yet other variations, the analgesic-related agent of the present invention has a constant charge (i.e., is ionized 100% or substantially 100% of the time) at physiological pH. Such variations can be synthesized by, for example, putting a quaternary amine or quanidino moiety off the aromatic or saccharide group. Such modifications will typically yield derivatives that do not get into the brain and are therefore useful for peripheral indications (e.g., as peripheral analgesics for reducing pain in the periphery without significant effect on brain receptors).

Pharmaceutical Compositions and Methods of Administration

The analgesic-related agents of the present invention are useful in a variety of applications relating to modulation of analgesic receptor signaling within the nervous system. For example, the agents of the present invention are useful as analgesics for the treatment of pain (e.g., for easing pain associated with surgical procedures or terminal illnesses such as cancer). The agents are also useful for the treatment of diseases or disorders amenable to amelioration via modulation analgesic (e.g., opioid) receptor signaling, particularly, for example, diseases or disorders of the CNS. Such diseases or disorders include, e.g., various addictions. Addictions amenable to treatment using the agents described herein include, for example, addictions to drugs such as narcotics (e.g., morphine, heroin, and other opiates), nicotine, and alcohol, as well as behavioral addictions (e.g., gambling addiction).

Accordingly, the present invention further provides pharmaceutical compositions and methods for the treatment of pain as well as for the treatment of addictions and other CNS-related disorders. The analgesic-related agents of the present invention can be delivered or administered to a mammal, e.g., human subject, alone, in the form of a pharmaceutically acceptable salt or hydrolysable precursor thereof, or in the form of a pharmaceutical composition wherein the compound is mixed with suitable carriers or excipient(s) in a therapeutically effective amount. In a preferred embodiment, for treating a drug addiction in a subject and when administered in an appropriate therapeutically effective regime, a sufficient amount of the analgesic-related agent is present to inhibit analgesic receptors in vivo so as to predispose the subject to ingest lower amounts of a drug.

The analgesic-related agents that are used in the methods of the present invention can be administered as pharmaceutical compositions comprising the agent together with one or more other pharmaceutically acceptable components. Pharmaceutical compositions can be in the form of solids (such as, e.g., powders, granules, dragees, tablets, or pills), semi-solids (such as, e.g., gels, slurries, or ointments), liquids, or gases (such as, e.g., aerosols or inhalants).

Suitable formulations for use in the present invention are found in, for example, [Remington's Pharmaceutical Sciences, Mack Publishing Company, Philadelphia, Pa., 17th ed. (1985) and Langer, *Science*, 249:1527-1533 (1990)]. The pharmaceutical compositions described herein can be manufactured in a conventional manner, e.g., mixing, dissolving, granulating, dragee-making, levigating, emulsifying, encapsulating, entrapping, or lyophilizing processes.

In preparing the formulations of the present invention, pharmaceutically recognized equivalents of each of the compounds can be alternatively used. These pharmaceutically recognized equivalents can be pharmaceutically acceptable esters, amides, or salts or pharmaceutically acceptable acid addition salts.

A pharmaceutically acceptable salt is a non-toxic metal, alkaline earth metal, or an ammonium salt commonly used in the pharmaceutical industry including, for example, a sodium, potassium, lithium, calcium, magnesium, barium, ammonium, and protamine zinc salt, which is prepared by methods well-known in the art. The term also includes a non-toxic acid addition salt, which is generally prepared by reacting the compounds of the present invention with a suitable organic or inorganic acid. Representative salts include, e.g., hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, and napsylate.

A pharmaceutically acceptable acid addition salt is a salt that retains the biological effectiveness and properties of the free bases and that is not biologically or otherwise undesirable, formed with inorganic acids such as, e.g., hydrochloric acid, hydrobromic acid, sulfuric acid, nitric acid, phosphoric acid, and the like, and organic acids such as, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salylic acid, and the like [see, e.g., Bundgaard ed., *Design of Prodrugs*, Elsevier Science Publishers, Amsterdam (1985)].

The analgesic-related agents can be formulated with common excipients, diluents or carriers, and compressed into tablets, for formulated as elixirs or solutions for convenient oral administration. The agents can also be formulated as sustained release dosage forms and the like.

In order to exert the desired therapeutic effects associated with binding of analgesic receptors in the brain, the analgesic-related agents of the present invention must reach brain cells and brain tissue, requiring their passage from the blood to the brain by crossing the blood brain barrier, comprising the microcapillary membranes of the cerebrovascular endothelium. The present invention provides methods for administering a therapeutically effective dosage regime of the analgesic-related agent to a peripheral tissue in a patient (i.e., tissues other than central nervous system tissues). This can be achieved in various ways, including oral, buccal, rectal, parenteral, intraperitoneal, intradermal, transdermal, subcutaneous, intratracheal, and intramuscular administration. Moreover, the agents can be administered in a local rather than systemic manner, in a depot or sustained release formulation (e.g., patient controlled analgesia). In addition, the agents can be administered in a vesicle, in particular a liposome [see, e.g., Langer, supra; Treat, In *Liposomes in the Therapy of Infectious Disease and Cancer*, Lopez-Berestein and Fidler eds., Liss, New York, pp. 353-365 (1989)].

For injection, the analgesic-related agents of the present invention can be formulated into preparations by dissolving, suspending, or emulsifying them in an aqueous or nonaqueous solvent such as, e.g., vegetable or other similar oils, synthetic aliphatic acid glycerides, esters of higher aliphatic acids, or propylene glycol; and, if desired, with conventional additives such as, e.g., solubilizers, isotonic agents, suspending agents, emulsifying agents, stabilizers, and preservatives. Preferably, for injection, the compounds of the present invention can be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art.

For oral administration, the analgesic-related agent can be formulated readily by combining with pharmaceutically acceptable carriers that are well-known in the art. Such carriers enable the compounds to be formulated as tablets, pills, dragees, capsules, emulsions, lipophilic and hydrophilic suspensions, liquids, gels, syrups, slurries, suspensions, and the like, for oral ingestion by a subject to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Particularly suitable excipients include fillers such as, for example, sugars (e.g., lactose, sucrose, mannitol, or sorbitol), cellulose preparations (e.g., maize starch, wheat starch, rice starch, potato starch, gelatin, gum tragacanth, methyl cellulose, hydroxypropylmethyl-cellulose, sodium carboxymethylcellulose, and/or polyvinyl pyrrolidone (PVP). If desired, disintegrating agents can be added, such as the cross-linked polyvinyl pyrrolidone, agar, or alginic acid or a salt thereof such as, e.g., sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, titanium dioxide, lacquer solutions, and/or suitable organic solvents or solvent mixtures. Dyestuffs or pigments can be added to the tablets or dragee coatings for identification or to characterize different combinations of active compound doses.

Pharmaceutical preparations that can be used orally include, for example, push-fit capsules made of gelatin, as well as soft, sealed capsules made of gelatin and a plasticizer, such as, e.g., glycerol or sorbitol. The push-fit capsules can contain the active ingredients in admixture with filler such as, for example, lactose, binders (e.g., starches), and/or lubricants (e.g., talc or magnesium stearate) and, optionally, stabilizers. In soft capsules, the active compounds can be dissolved or suspended in suitable liquids, such as, e.g., fatty oils, liquid paraffin, or liquid polyethylene glycol.

For buccal administration, the compositions can take the form of tablets or lozenges formulated in a conventional manner.

For administration by inhalation, the compounds for use in accordance with the present invention are conveniently delivered in the form of an aerosol spray preparation from pressurized packs or a nebulizer, with the use of a suitable propellant, e.g., dichlorodifluoromethane, trichlorofluoromethane, dichlorotetrafluoroethane, carbon dioxide or other suitable gas, or from propellant-free, dry-powder inhalers. In the case of a pressurized aerosol the dosage unit can be determined by, for example, providing a valve to deliver a metered amount. Capsules and cartridges of, e.g., gelatin for use in an inhaler or insufflator can be formulated containing a powder mix of the compound and a suitable powder base such as, for example, lactose or starch.

Analgesic-related agents of the present invention can be formulated for parenteral administration by injection, e.g., by bolus injection or continuous infusion. Formulations for injection can be presented in unit dosage form, e.g., in ampules or in multidose containers, with an added preservative. The compositions can take such forms as, e.g., suspensions, solutions, or emulsions in oil-based or aqueous vehicles, and can contain formulator agents such as, for example, suspending, stabilizing, and/or dispersing agents.

Pharmaceutical formulations for parenteral administration include aqueous solutions of the active compounds in water-soluble form. Alternatively, suspensions of the active compounds can be prepared as appropriate oily injection suspensions. Suitable lipophilic solvents or vehicles include fatty oils (e.g., sesame oil), synthetic fatty acid esters (e.g., ethyl oleate or triglycerides), or liposomes. Aqueous injection suspensions can contain substances that increase the viscosity of the suspension, such as, for example, sodium carboxymethyl cellulose, sorbitol, or dextran. Optionally, the suspension can also contain suitable stabilizers or agents that increase the solubility of the compounds to allow for the preparation of highly concentrated solutions. Alternatively, the active ingredient can be in powder form for constitution with a suitable vehicle, e.g., sterile pyrogen-free water, before use.

Analgesic-related agents can also be formulated in rectal compositions such as suppositories or retention enemas, e.g., containing conventional suppository bases such as, for example, cocoa butter, carbowaxes, polyethylene glycols, or other glycerides, all of which melt at body temperature, yet are solidified at room temperature.

In addition to the formulations described previously, the compounds can also be formulated as a depot preparation. Such long-acting formulations can be administered by implantation (for example, subcutaneously or intramuscularly) or by intramuscular injection. Accordingly, for example, the compounds can be formulated with suitable polymeric or hydrophobic materials (e.g., as an emulsion in an acceptable oil) or ion exchange resins, or as sparingly soluble derivatives (e.g., a sparingly soluble salt).

Alternatively, other delivery systems for hydrophobic pharmaceutical compounds can be employed. Liposomes and emulsions are well-known examples of delivery vehicles or carriers for hydrophobic drugs. In some methods, long-circulating, e.g., stealth, liposomes can be employed. Such liposomes are generally described in U.S. Pat. No. 5,013,556 to Woodle et al.

The compounds of the present invention can also be administered by controlled release means and/or delivery devices: In certain variations, a pump is used [see, e.g., Langer, supra; Sefton, *CRC Crit. Ref Biomed. Eng.*, 14:201 (1987); Buchwald et al., *Surgery*, 88:507 (1980); Saudek et al., *N. Engl. J. Med.*, 321:574 (1989)]. In other embodiments, polymeric materials are used [see, e.g., Medical Applications of Controlled Release, Langer and Wise eds., CRC Pres., Boca Raton, Fla. (1974); *Controlled Drug Bioavailability, Drug Product Design and Performance*, Smolen and Bull eds., Wiley, New York (1984); Ranger and Peppas, *J. Macromol. Sci. Rev. Macromol. Chem.*, 23:61 (1983); see also Levy et al., *Science*, 228:190 (1985); During et al., *Ann. Neurol.*, 25:351 (1989); Howard et al., *J. Neurosurg.*, 71:105 (1989)]. Controlled release means and delivery devices are also described in, e.g., U.S. Pat. Nos. 3,845,770; 3,916,899; 3,536,809; 3,598,123; and 4,008,719.

Certain organic solvents such as, e.g., dimethylsulfoxide (DMSO) also can be employed, although usually at the cost of greater toxicity. Additionally, the compounds can be delivered using a sustained-release system such as, for example, semipermeable matrices of solid hydrophobic polymers containing the therapeutic agent. Various types of sustained-release materials have been established. Sustained-release capsules can, depending on their chemical nature, release the compounds for a few hours up to over 100 days.

The pharmaceutical compositions can also comprise suitable solid or gel phase carriers or excipients. Examples of such carriers or excipients include, but are not limited to, calcium carbonate, calcium phosphate, various sugars, starches, cellulose derivatives, gelatin, and polymers such as, e.g., polyethylene glycols.

For treatment of drug addiction, compounds of the present invention may also be administered by incorporating the agent into a drug-containing product (for example, in the case of nicotine ingestion, a tobacco product such as, e.g., a cigarette). For example, in certain embodiments, a compound of the present invention is sprayed or otherwise applied onto the drug-containing product prior to ingestion.

Pharmaceutical compositions suitable for use in accordance with the present invention include compositions wherein the active ingredients are contained in a therapeutically effective amount. The therapeutically effective amounts for the methods of the present invention can depend on a variety of factors, including, e.g., age, body weight, general health, sex, diet, time and manner of administration, rate of excretion, drug combination, the judgment of the treating physician, and the severity of the particular affliction being treated. The amount of active agent will also depend upon the specific activity of the opiate-related agent and whether that agent is co-administered with any other therapeutic or prophylactic ingredients.

Typically, a subject treated in accordance with the methods provided herein has been identified as suffering from pain; has been diagnosed with a disease or disorder amenable to treatment or prophylaxis via modulation of analgesic (e.g., opioid) receptors; or has otherwise been identified as a subject that will obtain a physiological benefit using the compound. In certain variations, a subject, suffering from pain or diagnosed with a disease or disorder amenable to treatment or prophylaxis via modulation of analgesic receptors (e.g., addiction), is not suffering from a second disease or disorder. Further, in some embodiments, the subject is monitored during treatment for a physiological and/or clinical effect. For example, for treatment of pain, a subject can be monitored for relative severity of pain over the course of treatment; or, for the treatment of a disease or disorder amenable to amelioration via modulation of analgesic receptor signaling, a subject can be monitored for one or more symptoms associated with the disease or disorder.

EXAMPLES

The following examples are offered to illustrate, but not to limit the claimed invention. Compound reference numbers for Examples 1-32 correspond to those used hereinabove. Different compound reference designations are used in each of Example 33 and, collectively, Examples 34-45.

The following general information applies with respect to the synthesis and analysis of compounds set forth in Examples 1-32: All reactions were conducted under a positive pressure of nitrogen with magnetic stirring at ambient temperature using oven-dried glassware unless otherwise indicated. Air- and moisture-sensitive liquids were transferred via syringe through rubber septa. Silica gel (230-400 mesh) was used for column chromatography. DMF was dried by filtration through a column of neutral alumina and stored over activated 4 Å molecular sieves under nitrogen prior to use. All other solvents and reagents were used as received. $^1$H NMR and $^{13}$C NMR spectra were recorded at 500 MHz and 125 MHz, respectively. Melting points are uncorrected. Where combustion analyses are not specified, analytical purities were determined by straight phase HPLC using a Hitachi L74 liquid chromatograph with a D7500 integrator and a Hamilton PRP-I stainless steel column (250 mm×4.6 mm i.d.). HPLC mobile phases: A=55:45:0.01 MeOH/isopropanol/$HClO_4$; B=45:55/0.01 MeOH/isopropanol/$HClO_4$; C=70:30 $CH_3CN$/MeOH; D=MeOH.

Further, "type I," "type II," and "type III" as used hereinbelow refer generally to compounds of Formulas IV, V, and VI, respectively, described supra.

Example 1

6β-S-(Methyl-2',3',4'-tri-O-acetyl-β-D-glucopyranosyluronate)morphine 3a

A 60% dispersion of NaH (46 mg, 1.16 mmol) was added to a 0° C. DMF solution of 2a (424 mg, 1.21 mmol) and the resulting red mixture was stirred for 10 min. To the mixture of the thiol thus formed was added a 0° C. DMF (8 mL) solution of 1b (183 mg, 0.416 mmol) by syringe over 1 min. The resulting solution was stirred for 4 h while warming to rt. The reaction was poured into 0.5% aqueous HC (20 mL) and the pH was raised to 9 by the careful addition of solid $NaHCO_3$. The mixture was extracted with $CH_2Cl_2$ (3×50 mL) and the combined organic layers were washed with $H_2O$ (10 mL), brine (10 mL), dried over $Na_2SO_4$, filtered and concentrated to a grey solid that was purified by flash chromatography (15×2.5 cm $SiO_2$, 60:1 to 20:1 $CH_2Cl_2$/EtOH) to provide 3a as an off-white solid (144 mg, 56%). An analytical sample of 3a was obtained as a white solid by recrystallization from absolute EtOH: $R_f$=0.10 (20:1 $CH_2Cl_2$/MeOH); mp=135° C. (decomposed); $^1$H NMR δ 6.63 (d, J=7.9 Hz, 1H), 6.50 (d, J=7.9 Hz, 1H), 5.81 (ddd, J=9.1, 5.7, 3.0 Hz, 1H), 5.29-5.21 (m, 2H), 5.05 (d, J=9.2 Hz, 1H), 5.03 (s, 1H), 4.70 (d, J=9.6 Hz, 1H), 4.06 (d, J=9.6 Hz, 1H), 3.74 (s, 3H), 3.31 (m, 1H), 3.03-2.99 (m, 2H), 2.58 (dd, J=11.7, 4.0 Hz, 1H), 2.43 (s, 3H), 2.38-2.28 (m, 2H), 2.15-2.09 (m, 2H), 2.05 (s, 3H), 2.02 (s, 3H), 1.76 (dd, J=12.2, 1.8 Hz, 1H); $^{13}$C NMR (CDCl$_3$) δ 170.3, 169.6, 169.5, 167.0, 144.7, 138.5, 131.8, 130.4, 128.5, 126.7, 119.7, 116.8, 93.7, 84.6, 76.3, 73.4, 70.0, 69.4, 59.2, 53.1, 47.2, 45.0, 44.5, 43.1, 39.8, 35.6, 20.9, 20.8, 20.7; HRMS calcd for $C_{30}H_{36}NO_{11}S$ [M+H$^+$] 618.2009, found 618.2011; the average purity of 3a was found to be ≥99% by analytical HPLC giving $t_R$=3.47 min (mobile phase A) and $t_R$=3.98 min (mobile phase B).

Example 2

3-O-Acetyl-6β-S-(methyl-2',3',4'-tri-O-acetyl-β-D-glucopyranosyluronate) morphine 3b According to the procedure described for 3a, NaH (53 mg, 1.33 mmol), 1a (484 mg, 1.38 mmol) and 2a (246 mg, 0.51 mmol) provided 3b as an off-white powder (211 mg, 63%): $R_f$=0.33 (20:1 $CH_2Cl_2$/EtOH); mp 194° C. (decomposed); $^1$H NMR (CDCl$_3$) δ 6.74 (d, J=8.2 Hz, 1H), 6.58 (d, J=8.2 Hz, 1H), 5.83-5.80 (m, 1H), 5.53 (dd, J=1.5, 10.2 Hz, 1H), 5.29-5.21 (m, 2H), 5.09 (s, 1H), 5.00 (t, 1H), 4.72 (d, J=10.3 Hz, 1H), 4.06 (d, J=9.3 Hz, 1H), 3.76-3.73 (4H), 3.33 (m, 1H), 3.07-3.03 (2H), 2.60-2.58 (m, 1H), 2.44 (s, 3H), 2.37-2.20 (s, 3H over m, 2H), 2.15 (dt, J=3.7, 11.8 Hz, 1H), 2.04 (s, 3H), 2.03 (s, 3H), 2.02 (s, 3H), 1.80 (d, J=11.6 Hz, 1H); $^{13}$C NMR (CDCl$_3$) δ 170.3, 169.5, 169.4, 168.8, 167.0, 149.0, 133.0, 132.6, 132.0, 131.8, 128.0, 121.8, 119.5, 94.5, 85.1, 76.2, 73.3, 70.3, 69.4, 59.0, 53.0, 46.9, 45.6, 44.5, 43.2, 40.0, 35.7, 20.93, 20.90, 20.8, 20.7; MS (ESI) m/z=660 [M+H$^+$]; Anal. ($C_{32}H_{37}NO_{12}S$) calcd: C, 58.26; H, 5.65; N, 2.12; S, 4.86. Found C, 57.94; H, 5.75; N, 2.07; S, 4.97.

Example 3

3-O-Acetyl-6β-S-(2',3',4',5'-tetra-O-acetyl-β-D-glucopyranosyl)-6β-thiomorphine 3c According to the method described for 3a, thiol 2b (500 mg, 1.37 mmol), NaH (53 mg, 1.32 mmol) and tosylate 1b (246 mg, 0.51 mmol) gave 3c as an off-white foam (255 mg, 74%): $R_f$=0.20 (20:1 $CH_2Cl_2$/MeOH); mp=151.9° C.; $^1$H NMR (CDCl$_3$) δ 6.73 (d, J=8.2 Hz, 1H), 6.58 (d, J=8.2 Hz, 1H), 5.83-5.79 (m, 1H), 5.50 (dd, J=1.8, 9.7 Hz, 1H), 5.24-5.17 (m, 2H), 5.04 (t, J=9.9 Hz, 1H), 4.96 (t, J=9.9 Hz, 1H), 4.69 (d, J=10.2 Hz, 1H), 4.19 (d, J=4.2 Hz, 2H), 3.79-3.75 (m, 1H), 3.71 (d, J=6.0 Hz, 1H), 3.30 (dd, J=3.3, 5.6 Hz, 1H), 3.04 (d, J=18.8 Hz, 1H), 2.57 (dd, J=4.0, 12.2 Hz, 1H), 2.42 (s, 3H), 2.34-2.29 (m, 2H), 2.14-2.11 (m, 1H), 2.07 (s, 6H), 2.05 (s, 6H), 2.00 (s, 6H), 1.80-1.77 (m, 1H); $^{13}$C NMR (CDCl$_3$) δ 170.8, 170.1, 169.5, 169.3, 169.5, 148.8, 132.8, 132.1, 131.7, 131.6, 127.9, 121.6, 119.3, 94.4, 85.1, 75.9, 73.8, 70.3, 68.5, 62.4, 58.8, 46.7, 45.8, 44.3, 43.0, 39.7, 35.6, 20.7, 20.6, 20.5; MS m/z=674 [M+H]$^+$; HRMS m/z calcd for 674.2271, found 674.2238; the average purity of 3c was found to be 97.3% by analytical HPLC giving $t_R$=4.86 min (mobile phase A) and $t_R$=5.66 min (mobile phase B).

Example 4

6-βS-(2',3',4',5'-Tetra-O-acetyl-β-D-glucopyranosyl)-6β-thiomorphine 3d

This compound was isolated as a side product in the preparation of 3c (47 mg, 14.6%): $R_f$=0.08 (20:1 $CH_2Cl_2$/MeOH); mp 165.4° C.; $^1$H NMR δ 6.63 (d, J=8.2 Hz, 1H), 6.51 (d, J=8.2 Hz, 1H), 5.79 (ddd, J=3.6, 5.8, 9.6 Hz, 1H), 5.50 (dd, J=1.7, 9.6 Hz, 1H), 5.22 (t, J=9.3 Hz, 1H), 5.09-4.99 (m, 3H), 4.69 (d, J=10.2 Hz, 1H), 4.27-4.19 (m, 2H), 3.78-3.74 (m, 1H), 3.67 (d, J=5.8 Hz, 1H), 3.32 (m, 1H), 3.01 (d, J=18.9 Hz, 1H) over bs (1H), 2.61-2.58 (m, 1H), 2.44 (s, 3H), 2.39-2.27 (m, 2H), 2.16-2.11 (m, 2H), 2.08 (s, 3H), 2.06 (s, 3H), 2.05 (s, 3H), 2.03 (s, 3H), 1.78-1.75 (m, 1H); $^{13}$C NMR δ 171.1, 170.4, 169.69, 169.66, 144.6, 130.3, 131.8, 130.6, 128.3, 126.9, 119.7, 116.7, 94.2, 84.9, 76.1, 74.0, 70.4, 68.7, 62.5, 59.2, 47.2, 45.8, 44.5, 43.2, 39.8, 35.8, 21.0, 20.83, 20.80, 20.6; MS m/z=632 [M+H]$^+$; HRMS m/z calcd for $C_{31}H_{38}NO_{11}S$ 632.2166, found 632.2136; the average purity of 3d was found to be ≥98% by analytical HPLC giving $t_R$=3.98 min (mobile phase A) and $t_R$=4.40 min (mobile phase B).

Example 5

6β-S-(Methyl-2',3',4'-tri-O-acetyl-β-D-glucopyranosyluronate)codeine 3e

According to the general procedure described for 3a, 1c (231 mg, 0.51 mmol), 2a (483 mg, 1.38 mmol) and NaH (1.33 mmol) gave 3e as an off-white solid (249 mg, 77%): $R_f$=0.30, 20:1 $CH_2Cl_2$/EtOH); mp=172° C.; $^1$H NMR (CDCl$_3$) δ 6.64 (d, J=8.1 Hz, 1H), 6.54 (d, J=8.1 Hz, 1H), 5.82 (ddd, J=3.0, 6.0, 9.2 Hz, 1H), 5.53 (dd, J=1.8, 9.4 Hz, 1H), 5.27-5.22 (m, 2H), 5.14 (s, 1H), 4.99 (t, J=2.1 Hz, 1H), 4.71 (d, J=10.3 Hz, 1H), 4.02 (d, J=7.3 Hz, 1H), 3.83 (s, 3H), 3.79 (d, J=6.0 Hz, 1H), 3.73 (s, 3H), 3.29 (dd, J=3.3, 5.8 Hz, 1H), 3.05-3.00 (d, J=19.0 Hz, 1H over m, 1H), 2.55 (dd, J=4.3, 12.2 Hz, 1H), 2.42 (s, 3H), 2.35 (td, J=3.4, 12.4 Hz, 1H), 2.29 (dd, J=6.0, 19.0 Hz, 1H), 2.15 (td, J=5.0, 12.4 Hz, 1H), 2.02 (s, 3H), 2.016 (s, 3H), 2.00 (s, 3H), 1.77 (dd, J=1.5, 12.3 Hz, 1H); $^{13}$C NMR δ 170.2, 169.5, 169.4, 166.9, 146.3, 142.2, 133.1, 130.7, 127.9, 127.7, 119.1, 112.8, 93.6, 85.2, 76.1, 73.4, 70.3, 69.3, 59.1, 56.4, 53.0, 47.0, 45.5, 44.7, 43.3, 40.0, 36.2, 20.9, 20.8, 20.7, 20.6; MS (ESI) 632 [M+H]$^+$; Anal. ($C_{31}H_{37}NO_{11}S$) C, H, N, S.

Example 6

6-S-(2',3',4',5'-Tetra-O-acetyl-β-D-glucopyranosyl) 6β-thiocodeine, 3f

According to the procedure described for 3a, the thiol 2b (440 mg, 1.21 mmol), NaH (47 mg, 1.16 mmol) and 1c (203 mg, 0.448 mmol) provided 3f as an off-white foam (237 mg, 82%). An analytical sample was obtained by recrystallization from boiling hexanes: $R_f$=0.26 (20:1 $CH_2Cl_2$/EtOH); mp=142.5° C.; $^1$H NMR (CDCl$_3$) δ 6.65 (d, J=8.2 Hz, 1H), 6.55 (d, J=8.2 Hz, 1H), 5.85-5.81 (m, 1H), 5.52 (dd, J=1.9, 9.6 Hz, 1H), 5.22-5.19 (m, 2H), 5.06 (t, J=9.8 Hz, 1H), 4.97 (dd, J=9.5, 10.1 Hz, 1H), 4.69 (d, J=10.1 Hz, 1H), 4.23-4.16 (m, 2H), 3.83 (s, 3H), 3.76 (d, J=6.0 Hz, 1H), 3.76-3.71 (m, 1), 3.29 (dd, J=3.3, 5.8 Hz, 1H), 3.06-3.01 (m, 2H), 2.56 (dd, J=4.0, 12.2 Hz, 1H), 2.42 (s, 3H), 2.38-2.30 (m, 2H), 2.18-2.15 (m, 1H), 2.12 (s, 3H), 2.09 (s, 6H), 2.00 (s, 3H), 1.99-1.80 (m, 1H); $^{13}$C NMR (CDCl$_3$) δ 171.0, 170.4, 169.6, 169.5, 146.3, 142.2, 132.9, 130.7, 127.9, 127.6, 119.1, 112.7, 93.8, 85.5, 76.1, 74.0, 70.5, 68.5, 62.5, 59.1, 56.4, 47.0, 46.1, 43.3, 40.0, 20.93, 20.92, 20.8, 20.5; MS m/z=646 [M+H]$^+$; HRMS calcd for $C_{32}H_{40}NO_{11}S$ 646.2322, found 646.2304; the average purity of 3f was found to be ≧99% by analytical HPLC giving $t_R$=5.00 min (mobile phase A) and $t_R$=5.71 min (mobile phase B).

Example 7

Morphine-6β-S-D-glucuronide 4a

To a solution of 3b (50.0 mg, 0.076 mmol) in 1.6 mL of MeOH was added 5% aqueous NaOH (0.12 mL). The resulting golden solution was stirred at rt for 18.5 h, acidified to a pH of 5 with ten drops of glacial AcOH and concentrated. The resulting white, amorphous solid was purified by flash chromatography on silica gel (16×1 cm, 5:1 to 1:1 $CH_3CN$/MeOH), followed by drying for 4 h at 100° C. (0.25 mm Hg) to provide a white powder (19.4 mg, 54%): $R_f$=0.26 (1:1 $CH_3CN$/MeOH with 0.2% AcOH); mp=>300° C. (decomposed); $^1$H NMR (D2O) δ 6.65 (d, J=8.1 Hz, 1H), 6.61 (d, J=8.1 Hz, 1H), 5.92 (m, 1H), 5.61 (d, J=9.6 Hz, 1H), 5.19 (s, 1H), 4.69 (d, J=9.9 Hz, 1H), 3.87 (d, J=5.9 Hz, 1H), 3.77 J=9.0 Hz, 1H), 3.64 (m, 1H), 3.57-3.51 (m, 2H), 3.38 (t, J=9.2 Hz, 1H), 3.13-3.09 (m, 2H), 2.83 (dd, J=3.7, 12.3 Hz, 1H), 2.59-2.54 (s, 3H over m, 2H), 2.19 (dt, J=8.5, 13.2 Hz, 1H), 1.87 (d, J=12.0 Hz, 1H); $^{13}$C NMR (D$_2$O) δ 174.6, 144.3, 139.6, 129.8, 128.8, 127.7, 123.3, 119.0, 116.9, 91.7, 85.0, 79.3, 76.1, 71.3, 70.7, 58.0, 45.6, 43.3, 42.6, 40.3, 37.2, 33.0, 19.7; MS (ESI) m/z=478 [M+H]$^+$; Anal ($C_{23}H_{27}NO_8S$) calcd: C, 57.85; H, 5.70; N, 2.93; S 6.71. Found C, 57.75; H, 5.95; N, 2.73; S, 6.58.

Example 8

6β-Thiomorphine-6β-S-D-glucopyranoside, 4b

To an amber solution of 3c (50 mg, 0.0742 mmol) in MeOH (6 mL) was added 5% aqueous NaOH (0.4 mL). A white precipitate formed within 5 min. The mixture was stirred for 18 h and then the pH was reduced to 7 by the addition of 1.5 N AcOH (15 drops). The solution was stirred 5 min and then the pH was reduced to 8.5 by the addition of saturated NaHCO$_3$ (15 drops). The mixture was concentrated and the residue was dissolved in 0.5 mL of water with 3 drops of 13% NH$_4$OH and purified by preparative TLC (SiO$_2$, 200:40:5: 0.05 $CH_2Cl_2$/MeOH/H$_2$O/13% NH$_4$OH). The single uv active band was removed from the SiO$_2$ and the SiO$_2$ was washed with 4:1 CHCl$_3$/MeOH (100 mL). The filtrate was concentrated and the residue was refiltered through a cotton plug using 9:1 CHCl$_3$/MeOH (10 mL) as the eluant. The filtrate was concentrated and the resulting solid was dried for 4 h at 100° C. (0.25 mm Hg) giving the title compound as a white powder (20 mg, 59%): $R_f$=0.21; mp=>300° C. (dec) $^1$H NMR (CD$_3$OD) δ 6.55 (d, J=8.0 Hz, 1H), 6.46 (d, J=8.0 Hz, 1H), 5.90 (ddd, J=2.9, 5.8, 9.0 Hz, 1H), 5.52 (dd, J=1.6, 9.7 Hz, 1H), 5.22 (s, 1H), 4.54 (d, J=9.8 Hz, 1H), 3.90 (d, J=11.2 Hz, 1H), 3.77 (d, J=6.0 Hz, 1H), 3.70 (dd, J=5.2, 11.9 Hz, 1H), 3.42 (dd, J=3.2, 5.6 Hz, 1H), 3.42-3.41 (m, 3H), 3.24 (dd, J=8.4, 9.6 Hz, 1H), 3.07 (bs, 1H), 3.05 (d, J=18.7 Hz, 1H), 2.68 (dd, J=4.0, 12.3 Hz, 1H), 2.49 (s, 3H), 2.49-2.39 (m, 2H), 2.18 (dt, J=7.9, 12.8 Hz, 1H), 1.81-1.79 (m, 1H); $^{13}$C NMR 6146.3, 140.4, 131.5, 131.4, 130.3, 126.7, 120.4, 117.9, 95.3, 88.4, 82.3, 79.9, 74.8, 71.6, 63.2, 60.7, 48.2, 46.3, 45.3, 43.0, 40.4, 36.7, 30.9, 24.2; MS m/z=464 [M+H]$^+$; HRMS m/z calcd for $C_{23}H_{30}NO_7S$ 464.1743, found 464.1727; the average purity of 4b was found to be 97.0% by analytical HPLC giving $t_R$=3.94 min (mobile phase A) and $t_R$=4.42 min (mobile phase B).

Example 9

Codeine 6β-S-glucuronide, 4c

According to the procedure described for the preparation of 4a, 3e (60.4 mg, 0.095 mmol), MeOH (2 mL) and 5% aqueous NaOH (0.28 mL) provided 4c (38 mg, 79%) as a white solid: $R_f$=0.08 (1:1 MeCN/MeOH with 0.2% AcOH); mp=>300° C. (decomposed); 1H NMR (D$_2$O) 6.82 (d, J=8.2 Hz, 1H), 6.69 (d, J=8.2 Hz, 1H), 5.83 (ddd, J=2.8, 6.0, 9.5 Hz, 1H), 5.22 (s, 1H), 4.66 (d, J=9.9 Hz, 1H), 3.84 (d, J=6.0 Hz, 1H), 3.81 (s, 3H), 3.76 (d, J=6.0 Hz, 1H), 3.57-3.50 (m, 2H), 3.42 (dd, J=3.3, 5.7 Hz, 1H), 3.40-3.34 (m, 1H), 3.08 (d, J=19.0 Hz, 1H), 3.01 (m, 1H), 2.60 (dd, J=4.0, 12.4 Hz, 1H), 2.43-2.37 (s, 3H over m, 1H), 2.30 (td, J=3.4, 12.6 Hz, 1H), 2.12 (td, J=4.8 Hz, 13.0, 1H), 1.75 (d, J=12.0 Hz, 1H); $^{13}$C NMR (D2O) δ 174.5, 144.4, 140.5, 131.0, 129.5, 127.3, 127.1, 119.0, 112.9, 92.8, 85.1, 79.3, 76.1, 71.3, 70.8, 57.1, 55.7, 45.1, 43.2, 43.0, 40.5, 37.7, 33.8, 19.3; HRMS calcd for $C_{24}H_{25}NO_8S$ [M−H$^-$] 490.1536, found 490.1525; the average purity of 4c was found to be 96% by analytical HPLC giving $t_R$=1.62 min (mobile phase C) and $t_R$=1.46 min (mobile phase D).

Example 10

6β-Thiocodeine-6β-S-D-glucose, 4d

The ester 3f (120 mg, 0.186 mmol) was dissolved in MeOH (4 mL) and 5% aqueous NaOH (0.6 mL) was added. The mixture was stirred at rt for 18 h and then treated with saturated aqueous NH$_4$Cl (1 mL). The mixture was concentrated and the residue was purified by preparative TLC (SiO$_2$) using $CH_2Cl_2$/MeOH/water/13% concentrated NH$_4$OH (200:40:5: 0.050) as the eluant. A single uv active band was removed from the SiO$_2$ with a razor blade and this SiO$_2$ was washed with 4:1 CHCl$_3$/MeOH (100 mL). The filtrate was concentrated and the residue was refiltered through a cotton plug using 9:1 CHCl$_3$/MeOH (10 mL) as the eluant. The filtrate was concentrated and the resulting solid was dried for 4 h at 100° C. (0.25 mm Hg) giving the 4d as a white powder (23 mg, 26%): $R_f$=0.17; mp=201.6° C.; $^1$H NMR (CD3OD) δ 6.79 (d, J=8.3 Hz, 1H), 6.68 (d, J=8.3 Hz, 1H), 6.02 (ddd, J=3.0, 5.9, 9.1 Hz, 1H), 5.55 (dd, J=1.8, 9.8 Hz, 1H), 5.36 (s, 1H), 4.57 (d, J=9.8 Hz, 1H), 4.10 (dd, J=3.0, 6.2 Hz, 1H), 3.91 (dd, J=1.6, 12.1 Hz, 1H), 3.83 (d, J=6.1 Hz, 1H), 3.81 (s, 3H), 3.70 (dd, J=5.1, 12.0 Hz, 1H), 3.39-3.23 (complex m, 6H), 3.01-3.00 (m, 1H), 2.98 (s, 3H), 2.90 (dd, J=6.6, 19.8 Hz, 1H), 2.41 (dt, J=4.8, 13.8 Hz, 1H), 2.04 (dd, J=2.7, 14.0H, 1H); $^{13}$C NMR (CD3OD) δ 147.8, 144.5, 131.7, 130.1, 128.9, 125.3, 121.1, 116.2, 94.5, 88.3, 82.3, 79.9, 79.6, 74.8, 71.6, 63.1, 62.3, 57.3, 45.7, 44.3, 41.9, 38.8, 34.8, 23.0; MS m/z=478 [M+H]$^+$; HRMS m/z calcd for C$_{24}$H$_{32}$NO$_7$S 478.1899, found 478.1886; the average purity of 4d was found to be 96.5% by analytical HPLC giving t$_R$=4.79 min (mobile phase A) and t$_R$=5.64 min (mobile phase B).

Example 11

6βMethyl 2',3',4'-tri-O-acetyl-β-D-glucopyranosyluronate)acetamido-codeine 9b

Thionyl chloride (0.2 mL, 2.74 mmol) was added to carboxylic acid 8a (20.0 mg, 0.053 mmol) and the resulting colorless solution was stirred for 4 h under nitrogen. Toluene (1 mL) was added and the solution was concentrated by distillation under high vacuum with the aid of a 45° C. water bath. The resulting residue was cooled in a 0° C. ice bath. A 0° C. CH$_2$Cl$_2$ (2 mL) solution of amine 9b (32 mg, 0.106 mmol) containing 3 drops of NEt$_3$ was added by syringe. The resulting solution was stirred 20 h without replenishing the ice bath, diluted with CH$_2$Cl$_2$ (15 mL), washed with saturated aqueous NaHCO$_3$ (2×2 mL) and brine (2 mL). The organic layer was dried, filtered and concentrated to a thick yellow oil. Purification by flash chromatography (10×1 cm SiO$_2$, 10:1 CH$_2$Cl$_2$/MeOH) provided the title compound as a white solid (10 mg, 29%): R$_f$=0.17 (10:1 CH$_2$Cl$_2$/MeOH); $^1$H NMR (CDCl$_3$) δ 7.06 (d, J=6.8 Hz, 1H), 6.666 (d, J=8.2 Hz, 1H), 6.54 (d, J=8.2 Hz, 1H), 5.888 (ddd, J=3.0, 5.8, 9.4 Hz, 1H), 5.60 (dd, J=1.5, 9.4 Hz, 1H), 5.30 (s, 1H), 5.08 (t, J=3.0 Hz, 1H), 4.78 (s, 1H), 4.68-4.66 (m, 2H), 4.57 (d, J=10.4 Hz, 1H), 4.51 (t, J=6.2 Hz, 1H), 3.86 (s, 3H), 3.82 (s, 3H), 3.30 (m, 1H), 3.03 (d, J=18.5 Hz, 1H), 2.97 (m, 1H), 2.73 (dd, J=11.1, 17.0 Hz, 1H), 2.55 (dd, J=3.9, 11.6 Hz, 1H), 2.43 (s, 3H), 2.37-2.29 (m, 3H), 2.16 (s, 3H), 2.15 (s, 3H), 2.04 (s, 3H), 2.03-1.99 (m, 1H), 1.81-1.79 (m, 1H); MS (ESI) m/z=657 [M+H]$^+$.

Example 12

6α-(Methyl 2',3',4'-tri-O-acetyl-β-D-glucopyranosyluronate)acetamido-morphine, 10a According to the procedure described for compound 9b, carboxylic acid 8a (38.5 mg, 0.102 mmol), thionyl chloride (0.6 mL) and amine 7a (30 mg, 0.075 mmol) provided 10a as a white solid (29 mg, 51%): R$_f$=0.11 (20:1 CH$_2$Cl$_2$/MeOH); $^1$H NMR (CDCl$_3$) δ 7.01 (d, J=6.7 Hz, 1H), 6.59 (d, J=7.7 Hz, 1H), 6.45 (d, J=7.7 Hz, 1H), 5.88-5.84 (m, 1H), 5.59 (dd, J=1.6, 9.6 Hz, 1H), 5.08 (t, J=3.0 Hz, 1H), 4.72-4.66 (m, 2H), 4.58 (d, J=16.4 Hz, 1H), 4.49 (t, J=6.3 Hz, 1H), 3.82 (s, 3H), 3.84-3.72 (m, 2H), 3.29 (m, 1H), 3.01 (d, J=18.5 Hz, 1H), 2.94 (m, 1H), 2.75-2.69 (dd, J=11.0, 17.1 Hz, 1H), 2.53 (m, 1H), 2.43 (s, 3H), 2.42-2.29 (m, 2H), 2.19-1.99 (m, 2H), 2.163 (s, 3H), 2.157 (s, 3H) 2.06 s, 3H), 1.78-1.75 (m, 1H), 0.98 (s, 9H), 0.194 (s, 3H), 0.174 (s, 3H); MS (ESI) 757 [100, (M+H)$^+$]. The intermediate silyl ether (20 mg. 0.026 mmol) was dissolved in THF (1 mL). TBAF (0.030 mL, 0.030 mmol) and water (0.020 ml) were added and the purple solution was stirred at rt for 50 min, diluted with CH$_2$Cl$_2$ (20 mL) and washed with NH$_4$Cl (4 mL), brine (2 mL) and water (2 mL). The organic layer was dried (Na$_2$SO$_4$) filtered and concentrated to a pink foam (22 mg): R$_f$=0.22 (10:1 CH$_2$Cl$_2$/MeOH); MS m/z=643 [M+H]$^+$ Example 13

6β-(α-Glucuronosyl)acetamidomorphine 11a

Prepared by the procedure described for Example 7 from 10a (20 mg, 0.031 mmol), 5% aqueous NaOH (0.4 mL) and MeOH (2 mL) to give 11a as a white solid (2.1 mg, 18%): R$_f$=0.19 (SiO$_2$/MeOH with 0.2% AcOH); MS m/z=501 [M−H]$^−$.

Example 14

6β-α-D-glucuronosyl)acetamidocodeine 11b

The title compound was obtained by the procedure described for Example 7 as a white solid (13.5 mg, 86%): R$_f$=0.14 (MeOH with 0.2% AcOH); $^1$H NMR (D$_2$O) δ 6.97 (d, J=8.4 Hz, 1H), 6.84 (d, J=8.4 Hz, 1H), 5.89-5.85 (m, 1H), 5.71 (d, J=12.2 Hz, 1H), 4.94 (s, 1H), 4.62-4.59 (m, 1H), 4.36 (d, J=5.7 Hz, 1H), 4.22 (m, 1H), 4.03 (d, J=6.2 Hz, 1H), 3.88 (s, 3H), 3.80-3.73 (m, 2H), 3.35-3.30 (m, 2H), 3.03-2.94 (s, 3H overlapping m, 1H), 2.77-2.71 (m, 1H), 2.59 (dd, J=3.6, 16.1 Hz, 1H), 2.31 (td, J=4.7, 13.5 Hz, 1H), 2.06 (m, 1H); MS m/z=515 [M−H]$^−$.

Example 15

6β-(2',3',4',5'-Tetra-O-benzyl-β-D-glucopyranosyl)-3-O-Triisopropylsilyl-acetamidomorphine 9c Reference JMM-VI-113-2. SOCl$_2$ (1.5 mL) was added to the carboxylic acid 8b (115 mg, 0.20 mmol) and the solution was stirred at rt for 16 h. The excess SOCl$_2$ was removed by distillation and the colorless oil that resulted was dissolved in CH$_2$Cl$_2$ (2.5 mL) and added to the amine 7c (43.5 mg, 0.10 mmol) and NEt$_3$ (0.035 mL, 0.25 mmol) in CH$_2$Cl$_2$ (1 mL). The solution was stirred at rt for 1 h, concentrated and purified by flash chromatography (SiO$_2$, 30:1 to 10:1 EtOAc/MeOH), providing 9c as a white solid (70 mg, 70%): R$_f$=0.46 (10:1 CH$_2$Cl$_2$/MeOH); $^1$H NMR (CDCl$_3$) d 7.35-7.10 (20H), 6.59 (d, J=8.0 Hz, 1H), 6.40 (d, J=8.0 Hz, 1H), 6.22 (d, J=6.9 Hz, 1H), 5.71 (ddd, J=3.0, 6.0, 9.5 Hz, 1H), 5.41 (dd, J=1.9, 9.5 Hz, 1H), 4.89-4.48 (9H), 4.36 (t, J=6.3 Hz, 1H), 3.72-3.46 (5H), 3.29 (t, J=9.0 Hz, 1H), 3.17 (dd, J=3.0, 5.2 Hz, 1H), 2.96 (d, J=18.7 Hz, 1H), 2.88 (bs, 1H), 2.72 (dd, 2.7, 15.2 Hz, 1H), 2.50-1.72 (10H), 1.30-1.05 (21H).

Example 16

6β-(2',3',4',5'-Tetra-O-benzyl-β-D-glucopyranosyl) acetamidomorphine 10b

JMM-VI-114-2. The silyl ether 9c (60 mg, 59.7 mmol) was dissolved in THF (2 mL) and water (0.050 mL) was added and then TBAF (0.090 mL, 0.090 mmol, 1.0 M solution in THF). After 2.5 h, 1% concentrated HCl (4 mL) was added and the mixture was stirred for 2 min, diluted with water (10 mL) and made basic with solid NaHCO$_3$. The mixture was extracted with CH$_2$Cl$_2$ (5×30 mL), dried (Na$_2$SO$_4$), filtered and concentrated. Flash chromatography (24:1 to 12:1 EtOAc/MeOH) provided 10b as a white solid (42 mg, 83%): R$_f$=0.15 (12:1 EtOAc/MeOH); $^1$H NMR (CDCl$_3$) δ 7.34-7.10 (20H), 6.64 (d, J=8.2 Hz, 1H), 6.46 (d, J=8.2 Hz, 1H), 6.34 (d, J=6.3 Hz, 1H), 5.68 (ddd, J=2.5, 5.8, 9.5 Hz, 1H), 5.39 (d, J=9.5 Hz, 1H), 4.89-4.46 (10H), 4.34 (t, J=6.3 Hz, 1H), 3.72-3.46 (6H), 3.30 (t, J=9.1 Hz, 1H), 3.18 (bs, 1H), 2.97 (d, J=18.1 Hz, 1H), 2.94 (bs, 1H), 2.74 (dd, J=2.5, 15.7 Hz, 1H), 2.55-2.16 (7H), 1.95 (dt, J=8.0, 12.6 Hz, 1H), 1.76 (d, J=11.3 Hz, 1H).

Example 17

6β-(β-D-Glucopyranosyl)acetamidodihydromorphine 11e

JMM-VI-116-2. The tetrabenzyl derivative 10b (16 mg, 0.018 mmol) was dissolved in MeOH (2 mL) and concentrated HCl (3 drops) and then 10% Pd—C (16 mg) were added. The mixture was stirred under a balloon of hydrogen for 24 h and then filtered through Celite, washing the Celite with MeOH (10 mL). The filtrate was concentrated and the residue was purified by preparative TLC ($SiO_2$, 5:4:0.5:0.5 $CHCl_3/MeOH/H_2O$/concentrated $NH_4OH$), providing 11c as a white film (2.3 mg, 26%): $R_f$=0.40; MS m/z=491 ($MH^+$).

Example 18

6β-(3-Methoxyphenyl)acetamidomorphine, 13a 7c (80 mg, 0.182 mmol) was dissolved in $CH_2Cl_2$ (4 mL) and NEt3 (72 uL, 0.517 mmol) and 3-methoxyphenylacetyl chloride (80 uL, 0.513 mmol) were added by syringe. The resulting pale yellow solution was stirred at rt under an atmosphere of dry nitrogen in a closed vial. After 2 h, the solution was concentrated and the residue was purified by flash chromatography (20:1 $CHCl_3$/MeOH) to provide 12a as a white foam (78 mg, 73%): $R_f$=0.18 (20:1 $CH_2Cl_2$/MeOH); MS m/z: 589 (M+H)+. 12a (64 mg, 0.109 mmol) was dissolved in 5% aqueous THF (2.2 mL). TBAF (0.18 mL, 1.0 M solution in THF) was added by syringe and the pale yellow solution was stirred at rt under an atmosphere of dry nitrogen for 2 h. The solution was concentrated and 1% HCl (2 mL) was added. The mixture was stirred for 2 min and then transferred to a seperatory funnel with the aid of water (20 mL). The mixture was alkalized (pH 8.5) with solid $NaHCO_3$ and extracted with $CHCl_3$ (5×10 mL). The combined $CHCl_3$ extract was washed with brine (4 mL), dried ($Na_2SO_4$), filtered and concentrated. Flash chromatography (20:1 $CHCl_3$/MeOH) provided 13a as a white solid (38 mg, 81%): mp 144° C.; $R_f$=0.14 (20:1 $CHCl_3$/MeOH); $^1$H NMR δ 7.24 (J=7.9H, 1H), 6.82-6.79 (m, 3H), 6.64 (d, J=8.2 Hz, 1H), 6.49 (d, J=8.2 Hz, 1H), 5.67 (ddd, J=3.6, 6.1, 9.1 Hz, 1H), 5.58-5.53 (m, 2H), 4.65 (s, 1H), 4.37 (t, J=6.4 Hz, 1H), 3.79 (s, 3H), 3.54 (s, 2H), 3.34 (m, 1H), 3.00 (d, J=18.6 Hz, 1H), 2.89 (s, 1H), 2.61 (dd, J=4.0, 12.2 Hz, 1H), 2.43 (s, 3H), 2.38-2.29 (m, 2H), 1.99 (dt, J=9.6, 12.2 Hz, 1H), 1.76 (dd, 1.9, 12.6 Hz, 1H); $^{13}$C NMR δ 171.1, 160.2, 144.5, 138.9, 136.2, 132.8, 130.3, 129.9, 128.6, 125.8, 121.7, 119.6, 117.1, 115.1, 113.1, 93.0, 59.3, 55.4, 50.5, 47.3, 44.1, 43.9, 43.0, 39.8, 35.5, 20.5; MS m/z=433 [M+H]$^+$, 455 [M+Na]$^+$; HRMS m/z 433.2115 [M+H]% the average purity of 15a was found to be ≧99% by analytical HPLC giving $t_R$=4.38 min (mobile phase A) and $t_R$=5.09 min (mobile phase B).

Example 19

6β-(4-Methoxyphenyl)acetamidomorphine 13b

According to the general procedure described for 12a, 7c (78.4 mg, 0.178 mmol), $NEt_3$ (72 uL, 0.517 mmol) and 4-methoxyphenylacetyl chloride (80 uL, 0.523 mmol) gave 12b as a white foam (70 mg, 67%): $R_f$=0.11 (20:1 $CHCl_3$/MeOH); MS m/z: 589 (M+H)$^α$, 611 (M+Na)$^+$. Reference V-99. According to the procedure described for 13a, 12b (65 mg, 0.110 mmol) and TBAF (0.18 mL, 0.18 mmol) gave 13b (29 mg, 61%) as a white solid: mp 247 (dec); $R_f$=0.14 (20:1 $CHCl_3$/MeOH); $^1$H NMR δ 7.15 (d, J=8.6 Hz, 2H), 6.86 (d, J=8.6 Hz, 2H), 6.64 (d, J=8.1 Hz, 1H), 6.48 (d, J=8.1 Hz, 1H), 5.67 (ddd, J=3.0, 5.6, 9.5 Hz, 1H), 5.56 (dd, J=1.5, 9.5 Hz, 1H), 5.45 (d, J=6.4 Hz, 1H), 4.65 (s, 1H), 4.36 (t, J=6.3 Hz, 1H), 3.79 (s, 3H), 3.50 (s, 2H), 3.34 (m, 1H), 3.00 (d, J=18.6 Hz, 1H), 2.87 (s, 1H), 2.61 (dd, J=3.8, 11.9 Hz, 1H), 2.44 (s, 3H), 2.38-2.28 (m, 2H), 1.98 (dt, 4.9, 12.5 Hz, 1H), 1.77 (d, J=10.7 Hz, 1H); $^{13}$C δ 171.5, 158.8, 144.4, 138.7, 132.6, 130.4, 129.7, 128.3, 126.5, 125.6, 119.3, 117.0, 114.5, 92.8, 59.1, 55.3, 50.3, 47.0, 43.9, 42.9, 42.7, 39.6, 35.4, 20.2; MS m/z=433 (M+H)+, 456 (M+Na)$^+$; FIRMS m/z 433.2136 [M+H]$^+$; the average purity of 13b was found to be >99% by analytical HPLC giving $t_R$=4.44 min (mobile phase A) and $t_R$=5.24 min (mobile phase B).

Example 20

6β-(3-Methoxy)benzamidomorphine 13c

According to the general procedure described for 12a, 7c (82 mg, 0.185 mmol), $NEt_3$ (76 uL, 0.545 mmol) and anisoyl chloride (71 uL, 0.521 mmol) gave 12c as a white foam (88 mg, 82%); $R_f$=0.28 (10:1 $CH_2Cl_2$/MeOH); MS m/z: 575 (M+H)$^+$. According to the general procedure described for 13a, 12c (73 mg, 0.174 mmol) and TBAF (0.210 mL, 0.210 mmol) gave 13c as a white solid (42.5 mg, 58%): $R_f$=0.15 (15:1 dcm/MeOH); mp=212.9° C. (dec); $^1$H NMR δ 7.34-7.33 (m, 1H), 7.27-7.23 (m, 2H), 7.02-7.00 (m, 1H), 6.68 (d, J=8.1 Hz, 1H), 6.51 (d, J=8.1 Hz, 1H), 6.27 (d, J=6.8 Hz, 1H), 5.84 (ddd, J=3.0, 5.8, 9.2 Hz, 1H), 5.68 (dd, J=1.2 Hz, 9.9 HZ, 1H), 4.85 (s, 1H), 4.59 (t, J=6.4 Hz, 1H), 3.81 (s, 3H), 3.47 (dd, J=3.0, 5.0 Hz, 1H), 3.19-3.16 (m, 1H), 3.04 (d, J=18.5 Hz, 1H), 2.68 (dd, J=4.0, 12.0 Hz, 1H), 2.49 (s, 3H), 2.43-2.38 (m, 1H), 2.11 (dt, J=4.8, 12.6 Hz, 1H), 1.80 (d, J=10.9 Hz, 1H); $^{13}$C NMR δ 167.5, 160.0, 144.7, 139.1, 135.6, 132.7, 129.9, 129.8, 128.9, 125.5, 119.7, 119.0, 118.2, 117.4, 112.6, 93.0, 59.5, 55.7, 50.9, 47.4, 44.1, 43.0, 39.9, 35.4, 20.6; MS m/z 419 (M+H)$^+$, 441 (M+Na); HRMS m/z=419.1984 [M+H]$^+$; the average purity of 13c was found to be 99% by analytical HPLC giving $t_R$=4.41 min (mobile phase A) and $t_R$=5.05 min (mobile phase B).

Example 21

60-Benzamidomorphine, 13d

According to the general procedure described for 12a, 7c (82 mg, 0.232 mmol), $NEt_3$ (76 uL, 0.55 mmol) and benzoyl chloride (61 uL, 0.521 mmol) gave 12d as a white foam (79 mg, 78%); $R_f$=0.23 (20:1 $CHCl_3$/MeOH); MS m/z: 545 (M+H)$^+$. According to the general procedure described for 13a, 12d (65 mg, 0.110 mmol) and TBAF (0.18 mL, 0.18 mmol) gave 13d as a white solid (29 mg, 61%): $R_f$=0.15 (15:1 $CH_2Cl_2$/MeOH); mp=184.4° C. (dec); $^1$H NMR δ 7.78 (m, 2H), 7.53-7.50 (m, 1H), 7.42-7.41 (m, 1H), 6.72 (d, J=8.1 Hz, 1H)), 6.55 (d, J=8.1 Hz, 1H), 6.18 (d, J=6.2 Hz, 1H), 5.89 (ddd, J=3.0, 5.3, 9.5 Hz, 1H), 5.69 (dd, J=1.5, 9.5 Hz, 1H), 4.86 (s, 1H), 4.64 (t, J=6.3 Hz, 1H), 3.54 (s, 1H), 3.31 (s, 1H), 3.06 (d, J=18.7 Hz, 1H), 2.77 (m, 1H), 2.57 (s, 3H), 2.50-2.48 (m, 3H), 2.23-2.19 (m, 1H), 1.86 (dd, J=2.2, 12.9 Hz, 1H); $^{13}$C NMR δ 167.4, 144.5, 138.8, 133.9, 132.9, 131.7, 129.8, 128.6, 128.6, 127.0, 125.7, 119.4, 117.1, 92.8, 59.1, 50.6, 47.0, 44.0, 42.9, 39.9, 35.5, 20.5; MS m/z=389 [M+H]$^+$, 411 (M+Na)$^+$; HRMS m/z=389.1867 [M+H]$^+$; the average purity of 13d was found to be 99% by analytical HPLC giving $t_R$=4.43 min (mobile phase A) and $t_R$=5.16 min (mobile phase B).

Example 22

6β-(3'-Carbomethoxy)benzamidomorphine 13e

According to the general procedure described for 12a, 7c (159 mg, 0.362 mmol), $NEt_3$ (151 uL, 1.09 mmol) and monomethylphthaloyl chloride (217 mg, 1.01 mmol) 12e as a white foam (122 mg, 56%); $R_f$=0.22 (20:1 CHCl$_3$/MeOH); MS m/z: 603 (M+H)$^+$. According to the general procedure described for 13a, 12e (102 mg, 0.170 mmol) and TBAF (0.47 mL, 0.470 mmol) gave 13e as a white solid: $R_f$=0.14 (30:1 dcm/MeOH); mp=166.0° C. (dec); $^1$H NMR δ 8.32 (s, 1H), 8.14 (d, J=7.8 Hz, 1H), 8.00 (d, J=7.8 Hz, 1H), 7.49 (t, J=7.8 Hz, 1H), 6.68 (d, J=8.1 Hz, 1H), 6.52 (d, J=8.1 Hz, 1H), 6.33 (d, J=7.0 Hz, 1H), 5.85 (ddd, J=9.4, 5.6, 3.1 Hz, 1H), 5.73 (d, J=9.9, 1H), 4.85 (s, 1H), 4.62 (t, J=6.2 Hz, 1H), 3.93 (s, 3H), 3.42 (dd, J=3.2, 5.2, 1H), 3.10 (bs, 1H), 3.05 (d, J=18.5 Hz, 1H), 2.63 (dd, J=12.1, 4.2 Hz, 1H), 2.46 (s, 3H), 2.40-2.34 (m, 2H), 2.08 (dt, J=12.5, 4.9 Hz, 1H), 1.81 (d, J=10.8 Hz, 1H); $^{13}$C δ 166.4, 166.2, 144.3, 138.7, 134.2, 133.0, 132.7, 131.9, 130.5, 129.8, 128.9, 128.3, 127.6, 125.7, 119.5, 117.0, 92.9, 59.1, 52.4, 50.9, 47.1, 44.0, 42.9, 39.9, 35.4, 20.2; MS m/z=447 [M+H]$^+$; HRMS m/z=447.1930 [M+H]$^+$; the average purity of 13e was found to be ≧99% by analytical HPLC giving $t_R$=4.39 min (mobile phase A) and $t_R$=5.06 min (mobile phase B).

Example 23

6β-(3'Nitro)benzamidomorphine 13f

According to the general procedure described for 12a, 7c (80 mg, 0.182 mmol), NEt$_3$ (76 uL, 0.55 mmol) and 3-nitrobenzoyl chloride (95 mg, 0.51 mmol) gave 12f as a white foam (87 mg, 81%); $R_f$=0.17 (20:1 CHCl$_3$/MeOH); MS m/z: 590 (M+H)$^+$. According to the general procedure described for 13a, 12f (73 mg, 0.168 mmol) and TBAF (0.200 mL, 0.200 mmol) gave 13f as a light yellow solid (36 mg, 49%): $R_f$=0.11 (20:1 CHCl$_3$/MeOH); mp 208.3° C. (dec); $^1$H NMR δ 8.54 (t, J=1.4 Hz, 1H), 8.26 (dd, J=1.4, 8.2 Hz, 1H), 8.11 (d, J=8.0 Hz, 1H), 7.55 (t, J=8.0 Hz, 1H), 6.85 (d, J=6.4 Hz, 1H), 6.65 (d, J=8.1 Hz, 1H), 6.51 (d, J=8.1 Hz, 1H), 5.84 (ddd, J=3.0, 5.5, 9.2 Hz, 1H), 5.71 (d, J=10.3 Hz, 1H), 4.88, s, 1H), 4.63 (t, J=6.3 Hz, 1H), 3.45 (t, J=3.2 Hz, 1H), 3.18 (s, 1H), 3.04 (d, J=18:6 Hz, 1H), 2.68 (dd, J=3.8, 11.8 Hz, 1H), 2.47 (s, 3H), 2.41-2.34 (m, 2H), 2.15 (dt, J=7.6, 12.4 Hz, 1H), 1.78 (d, J=11.5 Hz, 1H); $^{13}$C δ 165.2, 148.0, 144.4, 138.9, 135.5, 133.3, 132.7, 129.8, 129.7, 128.2, 126.1, 125.4, 122.0, 119.5, 117.3, 92.5, 59.2, 51.1, 47.1, 43.9, 42.8, 39.6, 35.1, 20.3; MS m/z=434 [M+H]$^+$; HRMS m/z=434.1719 [M+H]$^+$; the average purity of 13f was found to be >99% by analytical HPLC giving $t_R$=4.11 min (mobile phase A) and $t_R$=4.78 min (mobile phase B).

Example 24

6β-(3',4'-Dichloro)benzamidomorphine, 13g

According to the general procedure described for 12a, 7c (81 mg, 0.184 mmol), NEt$_3$ (77 uL, 0.55 mmol) and 3,4-dichlorobenzoyl chloride (108 mg, 0.518 mmol) gave 12 g as a white foam (96 mg, 85%); $R_f$=0.20 (20:1 CH$_2$Cl$_2$/MeOH); MS m/z: 614 (M+H)$^+$, 616 (M+2+H)$^+$; 618 (M+4+H). According to the general procedure described for 13a, 12g (81 mg, 0.177 mmol) and TBAF (0.22 mL, 0.22 mmol) gave 13g as a white solid (48 mg, 49%): $R_f$=0.17 (15:1 CH$_2$Cl$_2$/MeOH); mp 228.5° C. (dec); $^1$H NMR δ 7.82 (d, J=2.1 Hz, 1H), 7.54 (dd, J=2.1, 8.4 Hz, 1H), 7.39 (d, J=8.4 Hz, 1H), 6.67 (d, J=8.0 Hz, 1H), 6.56 (d, J=6.2 Hz, 1H), 6.52 (d, J=8.0 Hz, 1H), 5.82 (ddd, J=2.9, 5.3, 9.5 Hz, 1H), 5.68 (dd, J=1.2, 9.5 Hz, 1H), 4.83 (s, 1H), 4.58 (t, J=6.3 Hz, 1H), 3.47 (dd, J=3.0, 5.3 Hz, 1H), 3.19 (m, 1H), 3.05 (d, J=18.6 Hz, 1H), 2.70 (dd, J=3.8, 11.9 Hz, 1H), 2.50 (s, 3H), 2.43-2.37 (m, 2H), 1.77 (d, J=11.0 Hz, 1H), $^{13}$C NMR δ 165.4, 144.4, 138.9, 136.1, 133.7, 133.0, 132.5, 130.5, 129.6, 129.3, 128.4, 126.3, 125.2, 119.5, 117.4, 92.5, 59.2, 52.4, 50.8, 47.2, 43.8, 42.7, 39.5, 35.1, 29.7, 25.8, 20.3, 20.5, 13.6; MS m/z 457 (M+H)$^+$; HRMS m/z=457.1087 [M+H$^+$]; the average purity of 13g was found to be >99% by analytical HPLC giving $t_R$=3.93 min (mobile phase A) and $t_R$=4.43 min (mobile phase B).

Example 25

6β-(Thiophen-2'-yl)acetamidomorphine 13h

According to the general procedure described for 12a, 7c (86 mg, 0.196 mmol), 2-thiopheneacetyl chloride (0.068 mL, 0.552 mmol) and NEt$_3$ (0.082 mL, 0.588 mmol) gave 12h as a white foam (66 mg, 60%); $R_f$=0.23 (20:1 CHCl$_3$/MeOH); MS m/z=565 [M+H]$^+$. According to the general procedure described for 13a, 12h (56 mg, 0.099 mmol) and TBAF (0.120 mL, 0.120 mmol) gave 13h as a white solid (32 mg, 79%): $R_f$=0.10 (20:1 CHCl$_3$/MeOH); mp 154.4° C.; $^1$H NMR δ 7.18 (d, J=4.5 Hz, 1H), 6.94-6.91 (m, 2H), 6.64 (d, J=8.1 Hz, 1H), 5.82 (d, J=7.1 Hz, 1H), 5.69 (ddd, J=3.5, 5.5, 9.4 Hz, 1H), 5.59 (dd, J=1.2, 9.9 Hz. 1H), 4.65 (s, 1H), 4.39 (t, J=6.4 Hz, 1H), 3.77 (s, 2H), 3.37 (dd, J=3.3, 5.8 Hz, 1H), 3.01 (d, J=18.5 Hz, 1H), 2.93 (m, 1H), 2.64 (dd, J=4.1, 12.1 Hz, 1H), 2.45 (s, 3H), 2.39-2.31 (m, 2H), 2.02 (dt, J=7.6, 12.6 Hz, 1H), 1.77 (dd, J=10.8, 1.7 Hz, 1H); $^{13}$C NMR δ 170.2, 144.6, 139.0, 136.0, 133.2, 129.9, 128.4, 127.6, 125.9, 125.6, 119.6, 117.3, 92.9, 59.2, 50.4, 47.3, 44.1, 43.0, 39.7, 37.7, 35.5, 20.5; MS m/z=409 [M+H]$^+$, 431 (M+Na)$^+$; HRMS m/z=409.1572 [M+H]$^+$; the average purity of 13h was found to be >99% by analytical HPLC giving $t_R$=4.31 min (mobile phase A) and $t_R$=5.02 min (mobile phase B).

Example 26

6β-(3'Carboxy)benzamidomorphine 14

Reference V-110. 13e (31 mg, 0.067 mmol) was dissolved in 4 mL of 1:1 THF/water and LiOH—H$_2$O (27 mg, 0.643 mmol) was added. The colorless solution was stirred at rt for 3.75 h, glacial acetic acid was added (15 drops) and the solution was concentrated. The residue was purified by flash chromatography on SiO$_2$ (5:1 to 1:1 CHCl$_3$/MeOH). The appropriate fractions were concentrated and the residue was stirred with 10 mL of 10:1 CHCl$_3$/MeOH and filtered through paper. The filtrate was concentrated to provide the title compound as a white solid, 20 mg (69%): $R_f$=0.17 (1:1 CHCl$_3$/MeOH with 0.2% AcOH), mp=217.1° C. (dec); $^1$H NMR δ 8.41-8.40 (m, 1H), 8.13-8.12 (m, 1H), 7.90-7.88 (m, 1H), 7.47 (t, J=7.7 Hz, 1H), 6.62 (d, J=8.2 Hz, 1H), 6.55 (d, J=8.2 Hz, 1H), 5.81-5.78 (m, 1H), 5.69 (d, J=9.9 Hz, 1H), 4.82 (s, 1H), 4.51-4.50 (m, 1H), 3.65 (dd, J=3.2, 5.4 Hz, 1H), 3.27 (bs, 1H), 3.12 (d, J=18.9 Hz, 1H), 2.87 (dd, J=4.0, 12.9 Hz, 1H), 2.64-2.57 (m, 2H), 2.20 (dt, J=4.8, 12.9 Hz, 1H), 1.81 (dd, J=2.4, 12.9 Hz, 1H); $^{13}$C NMR δ 180.5, 170.2, 145.6, 141.2, 139.4, 135.5, 133.6, 131.0, 130.9, 130.5, 130.3, 129.5, 129.2, 125.6, 120.7, 118.5, 93.8, 61.3, 52.8, 42.6, 39.9, 35.1, 30.9, 22.1 MS m/z 431 (M–H)$^-$; HRMS m/z calcd for C$_{25}$H$_{25}$N$_2$O$_5$ 433.1758, found 433.1749; the average purity of 14 was found to be 99% by analytical HPLC giving $t_R$=3.93 min (mobile phase A) and $t_R$=4.43 min (mobile phase B).

Example 27

In Vitro Binding Assays

A. Methods. Binding to cell membranes was conducted in a 96-well format. [See, N. Zaveri et al., *Eur. J. Pharmacol.*, 428:29-36 (2001)]. Cells were removed from the plates by scraping with a rubber policeman, homogenized in Tris buffer using a Polytron homogenizer, then centrifuged once and washed by an additional centrifugation at 27,000×g for 15 min. The pellet was resuspended in 50 mM Tris, pH 7.5, and the suspension incubated with [$^3$H]DAMGO, [$^3$H]DPDPE, or [$^3$H]U69593, for binding to u, d or k opioid receptors, respectively. The total volume of incubation was 1.0 mL and samples were incubated for 60-120 min at 25° C. The amount of protein in the binding reaction varied from approximately 15 μg to 30 μg. The reaction was terminated by filtration using a Tomtec 96 harvester (Orange, Conn.) with glass fiber filters. Bound radioactivity was counted on a Pharmacia Biotech beta-plate liquid scintillation counter (Piscataway, N.J.) and expressed in counts per minute. $IC_{50}$ values were determined using at least six concentrations of test compound, and calculated using Graphpad/Prism (ISI, San Diego, Calif.). $K_i$ values were determined by the method of Cheng and Prusoff. [See Y. Cheng, and W. H. Prusoff, *Biochem. Pharmacol.*, 22:3099-3108 (1973).]

B. Results. Affinity and Selectivity of the Ligands. Table 1 contains the $K_i$ values for compounds 5 and 6. $K_i$ is the parameter that measures the inhibition of radioligand binding to the receptor by the test compound. As with M6G, each ligand tested was mu selective. With respect to the type I compounds, the rank order of affinity for the most active compounds was 6b=5a>5d>6a. Each of these compounds possessed a free phenolic hydroxyl group. Compared to M6G their affinities were increased 1.5 to 2.4-fold at mu, 2.9 to 10.3 at delta and 1.4 to 369-fold at the kappa receptor. Compounds 5a and 5b each possessing a carbomethoxy group at the C-5' position showed a 1.7 to 2.7-fold selectivity for the kappa receptor over the delta receptor. All of the other ligands showed selectivity for the delta receptor over the kappa receptor. The replacement of the carbomethoxy group at C-5' in compound 5a with an acetoxymethyl group in compound 5d decreased the affinity for the kappa receptor by a factor of 270. The affinity of the remaining compounds for the mu, delta and kappa receptors possessing either 3-acetoxy groups or 3-methyl ether groups was significantly decreased when compared to M6G. In each instance, hydrolysis of the ester functional groups in the sugar moiety greatly diminished affinity of the ligands for the kappa receptor, while having a significantly less pronounced effect on the affinity of the ligands for the mu and delta receptors.

With respect to the mu binding affinity of type H compounds, the morphine analogue 10 (2.80 nM) possessing a free phenolic hydroxyl group and a fully esterified glucuronic acid moiety had the highest affinity. This observation is consistent with those results observed for the type I analogue 3a. Interestingly, the codeine derivative 9b (7.43 nM) showed significantly higher affinity than any type I codeine compound. Compound 11a (14.6 nM) and 11b (41.5 nM) showed reduced affinity. In comparison to M6G, compound 10 showed a 4.5-fold higher affinity for the mu receptor and compound 9b showed a 1.7-fold higher affinity. The type H compounds were significantly more selective than the type I compounds. The selectivity of compound 11b for the mu receptor approached that of M6G, although it possessed a 3.2-fold reduction in binding affinity. These results suggest that the carbon bridge between the morphine or codeine nucleus and the sugar residue may be critical for mu receptor selectivity. It is conceivable that the additional conformational mobility imparted by this bridge allows these molecules to interact with the mu receptor more similarly to M6G, which possesses a C-6 alpha sugar residue.

With the exception of compound 14 (19.92 nM), the $K_i$ values for type III compounds at the mu receptor were between 0.21 and 0.59 nM. These compounds were between 20-fold and 6-β-fold higher affinity for the mu receptor than M6G. Type III compounds were at least 9-fold higher affinity than the highest affinity type I compound and at least 4.7-fold higher affinity than the highest affinity type II compound. These results suggest that the C-6 substituent in these ligands was interacting with a hydrophobic region of the mu binding pocket. This observation is further supported by the decrease in affinity observed in compound 14 (19.92 nM). In most instances, type II compounds showed an increased mu versus delta selectivity and a reduced mu versus kappa selectivity. Replacement of the N-methyl substituent of the bridgehead N with cyclopropyl methyl or cyclobutyl methyl or similar substituents will typically afford antagonists of the receptors for the activity described below.

TABLE 1

Inhibition constants from competition binding assays of M6G derivatives at the mu, delta and kappa opiod receptors.

| entry | cmpd | Ki (nM) | | | δ/μ | κ/μ |
|---|---|---|---|---|---|---|
| | | μ | δ | κ | | |
| morphine | 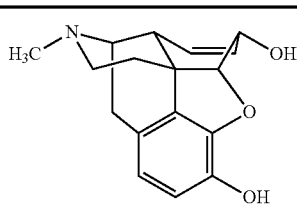 | 1.1 ± 0.05 | 140 ± 2 | 46.9 ± 14 | 127 | 42 |

TABLE 1-continued
Inhibition constants from competition binding assays of M6G
derivatives at the mu, delta and kappa opiod receptors.
| entry | cmpd | Ki (nM) | | | δ/μ | κ/μ |
|---|---|---|---|---|---|---|
| | | μ | δ | κ | | |
| M6G | 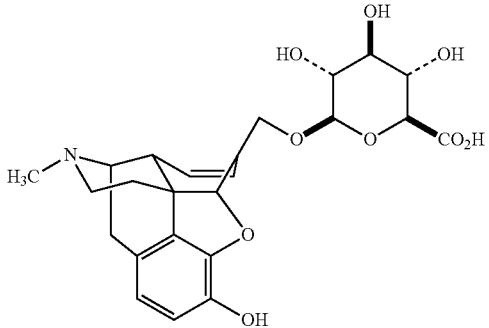 | 12.85 ± 0.95 | 160.96 ± 0.73 | 4058.75 ± 230 | 13 | 317 |
| 3a | 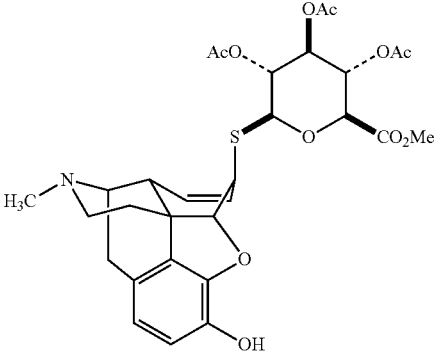 | 5.37 ± 0.14 | 15.6 ± 2.4 | 11.0 ± 0.06 | 2.9 | 2.0 |
| 3b | 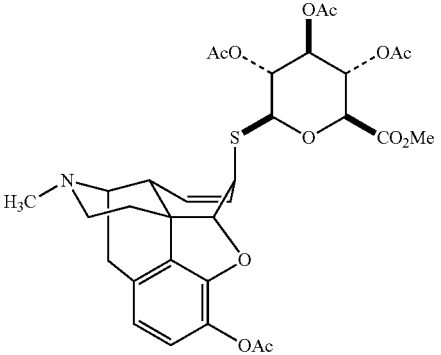 | 100 ± 1.9 | 528 ± 47 | 189 ± 14 | 5.3 | 1.9 |
| 3c | 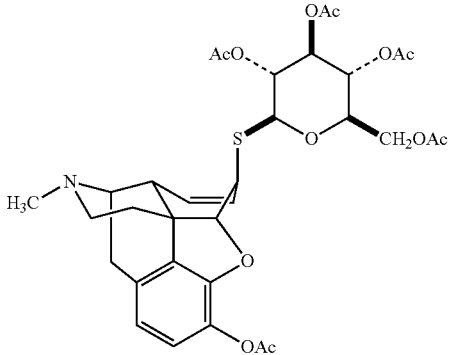 | 305.04 ± 66.04 | 762.07 ± 166.54 | 1385.66 ± 197.40 | 2.5 | 4.5 |

TABLE 1-continued

Inhibition constants from competition binding assays of M6G
derivatives at the mu, delta and kappa opiod receptors.

| entry | cmpd | Ki (nM) μ | Ki (nM) δ | Ki (nM) κ | δ/μ | κ/μ |
|---|---|---|---|---|---|---|
| 3d | | 7.78 ± 0.48 | 19.49 ± 0.31 | 2973.60 ± 947.83 | 2.5 | 382 |
| 3e | | 64 ± 1.1 | 438 ± 5 | 499 ± 6.6 | 6.8 | 7.8 |
| 3f | | 164.61 ± 27.66 | 465.77 ± 118.71 | 2186 ± 878.08 | 2.8 | 13 |
| 4a | | 8.73 ± 0.85 | 31.4 ± 2.3 | 288 ± 12 | 3.6 | 33 |

TABLE 1-continued

Inhibition constants from competition binding assays of M6G derivatives at the mu, delta and kappa opiod receptors.

| entry | cmpd | Ki (nM) μ | Ki (nM) δ | Ki (nM) κ | δ/μ | κ/μ |
|---|---|---|---|---|---|---|
| 4b | (structure) | 5.35 ± 0.78 | 56.23 ± 2.15 | 136.0 ± 16.93 | 10.4 | 25 |
| 4c | (structure) | 463 ± 57 | 2679 ± 205 | >10,000 | 5.8 | >21 |
| 4d | (structure) | 127.12 ± 22.72 | 1138.22 ± 353.73 | 2476.68 ± 536.30 | 9 | 19.5 |
| 10 | (structure) | 2.80 ± 0.1 | 16.2 ± 1.2 | 26.2 ± 0.6 | 5.8 | 9.4 |

TABLE 1-continued

Inhibition constants from competition binding assays of M6G
derivatives at the mu, delta and kappa opiod receptors.

| entry | cmpd | Ki (nM) μ | δ | κ | δ/μ | κ/μ |
|---|---|---|---|---|---|---|
| 11a | | 14.6 ± 2.4 | 53.8 ± 3.1 | 325 ± 17 | 3.7 | 22 |
| 9b | | 7.43 ± .55 | 176 ± 27 | 499 ± 49 | 24 | 67 |
| 11b | | 41.5 ± 5.3 | 984 ± 61 | >10,000 | 24 | 241 |
| 13a | | 0.35 ± 0.08 | 9.5 ± 2.58 | 0.96 ± 0.2 | 27 | 2.7 |

TABLE 1-continued

Inhibition constants from competition binding assays of M6G derivatives at the mu, delta and kappa opiod receptors.

| entry | cmpd | Ki (nM) | | | δ/μ | κ/μ |
| --- | --- | --- | --- | --- | --- | --- |
| | | μ | δ | κ | | |
| 13b | (structure with 4-methoxyphenylacetamide) | 0.59 ± 0.19 | 8.89 ± 2.1 | 2.84 ± 0.96 | 44 | 4.8 |
| 13c | (structure with 3-methoxybenzamide) | 0.21 ± 0.07 | 8.96 ± 1.95 | 2.65 ± 1.25 | 42 | 12.8 |
| 13d | (structure with benzamide) | 0.40 ± 0.03 | 24.95 ± 2.33 | 4.13 ± 1.21 | 62.5 | 10.3 |
| 13e | (structure with 3-methoxycarbonylbenzamide) | 0.23 ± 0.05 | 3.39 ± 0.03 | 1.53 ± 0.2 | 15 | 6.7 |

TABLE 1-continued

Inhibition constants from competition binding assays of M6G derivatives at the mu, delta and kappa opiod receptors.

| entry | cmpd | Ki (nM) μ | Ki (nM) δ | Ki (nM) κ | δ/μ | κ/μ |
|---|---|---|---|---|---|---|
| 13f | (structure: M6G derivative with 3-nitrobenzamide) | 0.20 ± 0.04 | 18.0 ± 5.63 | 2.63 ± 1.1 | 36 | 13 |
| 13g | (structure: M6G derivative with 3,4-dichlorobenzamide) | 0.20 ± 0.04 | 0.94 ± 0.02 | 0.75 ± 0.2 | 4.7 | 3.8 |
| 13h | (structure: M6G derivative with 2-thienylacetamide) | 0.33 ± 0.02 | 14.42 ± 1.26 | 0.58 ± 0.17 | 44 | 1.8 |
| 14 | (structure: M6G derivative with 3-carboxybenzamide) | 19.92 ± 4.29 | 50.78 ± 8.86 | >10K | 2.5 | 502 |

Example 28

[$^{35}$S]GTP γ-S Binding Studies to Measure Coupling to G Proteins

A. Methods. Radiolabelled S binding was conducted basically as described by [J. R. Traynor and S. R. Nahorski, *Mol. Pharmacol.*, 47:848-854 (1995)]. Cells were scraped from tissue culture dishes into 20 mM Hepes, 1 mM EDTA, then centrifuged at 500×g for 10 min. Cells were resuspended in this buffer and homogenized using a Polytron homogenizer. The homogenate was centrifuged at 27,000×g for 15 min and the pellet resuspended in Buffer A, containing 20 mM Hepes, 10 mM $MgCl_2$, 100 mM NaCl, pH 7.4. The suspension was recentrifuged at 27,000×g and suspended once more in Buffer A. For the binding assay, membranes (8-15 μg protein) were incubated with [$^{35}$S]GTPγ-S (50 μM), GDP (10 μM), and the appropriate compound, in a total volume of 1.0 mL, for 60 min at 25° C. Samples were filtered over glass fiber filters and counted as described for the binding assays. Statistical analysis was conducted using the program Prism.

B. Results. Potency and Efficacy of Ligands. In order to evaluate the opioid receptor-mediated activation of its associated G protein, the compounds were evaluated using [$^{35}$S] GTP γS assays. These data are summarized in Table 2. In this assay, the compound's potency or affinity for the receptor is defined by its $EC_{50}$ for stimulating [$^{35}$S]GTPγS binding. Agonist efficacy is defined as the degree to which the compound maximally stimulates [$^{35}$S]GTPγS binding relative to the control. The $EC_{50}$ value represents the concentration of a compound that produced 50% maximal stimulation of [$^{35}$S] GTPγS binding by that compound. Full agonists stimulate [$^{35}$S]GTPγS binding to a maximal extent and partial agonists cause a reduced level of binding. Table 2 gives the $E_{max}$ and $EC_{50}$ values for stimulation of [$^{35}$S]GTPγS binding at human mu, delta and kappa opioid receptors. With the exception of compound 6c all of the compounds stimulated [$^{35}$S]GTPγS binding at the mu and delta receptors. The compounds were much less efficacious at the kappa receptor. This trend was also observed for M6G. The most efficacious compounds at the mu receptor were compounds 3b (88.0%), 3d (76.0%), 4b (64.5%), and 4a (46.6%) (see Table 2). Each of these compounds possessed a free phenolic hydroxyl group. These compounds were all more efficacious than M6G. The same general trend was observed at the delta receptor with compounds possessing a free phenolic hydroxyl showing increased efficacy. The most efficacious compounds were 3b (104.4%), 4a (78.70%), 3e (64.3%), and 4b (51.5%). Protection of the phenolic hydroxyl group with an acetate group or a methyl group diminished the efficacy and potency at each receptor. Compounds that effected maximal stimulation may be viewed as agonists at a given receptor. Those ligands that elicited less than maximal binding may be viewed as partial agonists or antagonists if no stimulation was observed. The overall rank order of the $EC_{50}$ values correlated with the values. With respect to the type IX compounds, ligands 10 and 9b produced maximum stimulation of [$^{35}$S]GTPgammaS binding by the mu receptor and reduced stimulation of [$^{35}$S] GTPgammaS binding at the delta and kappa receptors. With respect to type III compounds 13a-h and 14 each of the compounds stimulated [$^{35}$S]GTPγS binding at the mu, delta and kappa receptors.

The compounds were generally more efficacious at the mu and kappa receptors as opposed to the delta receptor. Compounds that effected maximal stimulation may be viewed as agonists at a given receptor. Those ligands that elicited less than maximal binding may be viewed as partial agonists or antagonists if no stimulation was observed. The overall rank orders of the $EC_{50}$ values correlated with the $K_i$ values.

TABLE 2

Stimulation of $^{35}$S-GTP-γ-S binding by M6G derivatives

| entry | cmpd | mu $EC_{50}$ | % stimulation | delta $EC_{50}$ | % stimulation | kappa $EC_{50}$ | % stimulation |
|---|---|---|---|---|---|---|---|
| M6G | 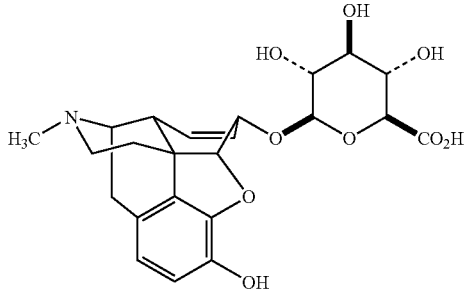 | 72.3 ± 26.7 | 45.0 ± 5.0 | 190.35 ± 22.9 | 80.0 ± 0 | >10K | |
| 3a | | 1424 ± 239 | 37.8 ± 6.7 | 1323 ± 304 | 46.83 ± 1.98 | flat | flat |

TABLE 2-continued

Stimulation of $^{35}$S-GTP-γ-S binding by M6G derivatives

| entry | cmpd | mu | | delta | | kappa | |
|---|---|---|---|---|---|---|---|
| | | $EC_{50}$ | % stimulation | $EC_{50}$ | % stimulation | $EC_{50}$ | % stimulation |
| 3b | (structure) | 43.7 ± 16.48 | 88.3 ± 19.5 | 80.16 ± 0.16 | 104.4 ± 19.95 | 29.11 ± 8.23 | 23.52 ± 0.92 |
| 3c | (structure) | 4794 ± 1615 | 44.1 ± 4.9 | 3659 ± 1510 | 39.3 ± 0.8 | 1722 ± 634 | 36.9 ± 1.9 |
| 3d | (structure) | 33.7 ± 11.3 | 76.0 ± 3.0 | 63.8 ± 14.6 | 45.5 ± 1.5 | 52.0 ± 4.9 | 26.5 ± 2.5 |
| 3e | (structure) | 732.2 ± 47.1 | 19.3 ± 0.3 | 1009 ± 178 | 64.3 ± 8.3 | 2667 ± 64 | 24.34 ± 4.2 |

TABLE 2-continued

Stimulation of $^{35}$S-GTP-γ-S binding by M6G derivatives

| entry | cmpd | mu EC$_{50}$ | mu % stimulation | delta EC$_{50}$ | delta % stimulation | kappa EC$_{50}$ | kappa % stimulation |
|---|---|---|---|---|---|---|---|
| 3f | (structure) | 993.7 ± 13.3 | 41.9 ± 2.1 | 871.5 ± 241.6 | 44.9 ± 1.2 | >10K | flat |
| 4a | (structure) | 90.6 ± 22.94 | 46.6 ± 10.1 | 50.13 ± 36.7 | 78.70 ± 0.92 | flat | flat |
| 4b | (structure) | 91.5 ± 23.4 | 64.5 ± 0.5 | 191.7 ± 14.8 | 51.5 ± 6.5 | 320.9 ± 93.1 | 42.5 ± 2.5 |
| 4c | (structure) | flat | flat | 1331 ± 20.5 | 44.25 ± 5.4 | flat | flat |

TABLE 2-continued

Stimulation of $^{35}$S-GTP-γ-S binding by M6G derivatives

| entry | cmpd | mu | | delta | | kappa | |
|---|---|---|---|---|---|---|---|
| | | $EC_{50}$ | % stimulation | $EC_{50}$ | % stimulation | $EC_{50}$ | % stimulation |
| 4d | [structure] | 1059 ± 22 | 42.0 ± 6.0 | 1740 ± 312 | 27.7 ± 3.3 | 4628 ± 1773 | 21.0 ± 0 |
| 10 | [structure] | 9.4 ± 3.2 | 104.3 ± 1.2 | 29.57 ± 3.7 | 62.35 ± 9.36 | 119 ± 59.6 | 45.2 ± 3.4 |
| 11a | [structure] | 113.9 ± 5.55 | 44.5 ± 7.1 | 67.62 ± 0.9 | 69.81 ± 0.58 | 1213 ± 19 | 49.5 ± 1.3 |
| 9b | [structure] | 83.9 ± 4.3 | 96.8 ± 8.22 | 424.9 ± 100 | 76.49 ± 19.94 | 1844.5 ± 54.5 | 30.65 ± 3.86 |

TABLE 2-continued

Stimulation of $^{35}$S-GTP-γ-S binding by M6G derivatives

| entry | cmpd | mu | | delta | | kappa | |
|---|---|---|---|---|---|---|---|
| | | $EC_{50}$ | % stimulation | $EC_{50}$ | % stimulation | $EC_{50}$ | % stimulation |
| 11b | [structure] | 672.3 ± 6.4 | 27.1 ± 3.4 | 1031 ± 34.2 | 48.92 ± 5.5 | flat | flat |
| 13a | [structure] | 1.7 ± 0.17 | 99.0 ± 4.0 | 18.8 ± 2.21 | 51.0 ± 4.0 | 4.8 ± 0.1 | 89.0 ± 6.0 |
| 13b | [structure] | 4.8 ± 2.05 | 72.5 ± 14.5 | 25.2 ± 3.0 | 59.5 ± 3.5 | 5.0 ± 1.0 | 81.5 ± 1.5 |
| 13c | [structure] | 2.8 ± 0.24 | 87.5 ± 6.5 | 37.8 ± 1.9 | 65.5 ± 5.5 | 9.8 ± 0.02 | 86.0 ± 0.0 |

TABLE 2-continued
Stimulation of $^{35}$S-GTP-γ-S binding by M6G derivatives
| entry | cmpd | mu | | delta | | kappa | |
|---|---|---|---|---|---|---|---|
| | | EC$_{50}$ | % stimulation | EC$_{50}$ | % stimulation | EC$_{50}$ | % stimulation |
| 13d | 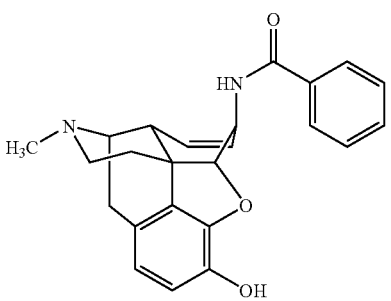 [SMILES: CN1CCC23c4c5ccc(O)c4OC2C(NC(=O)c2ccccc2)C=CC3C1C5] | 5.5 ± 0.9 | 90.5 ± 9.5 | 62.7 ± 24.0 | 61.3 ± 2.3 | 5.3 ± 1.3 | 81.1 ± 8.9 |
| 13e | 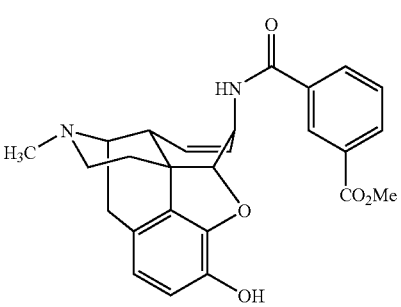 [SMILES: COC(=O)c1cccc(C(=O)NC2C=CC3C4Cc5ccc(O)c6c5C3(CCN4C)C2O6)c1] | 2.4 ± 0.32 | 98.1 ± 7.9 | 6.20 ± 0.42 | 99.63 ± 2.19 | 11.22 ± 3.51 | 88.6 ± 8.6 |
| 13f | 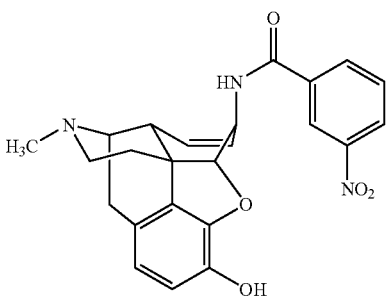 [SMILES: CN1CCC23c4c5ccc(O)c4OC2C(NC(=O)c2cccc([N+](=O)[O-])c2)C=CC3C1C5] | 1.9 ± 0.16 | 95.5 ± 7.5 | 24.5 ± 3.0 | 94.1 ± 10.9 | 1.2 ± 0.1 | 90.3 ± 4.8 |
| 13g | 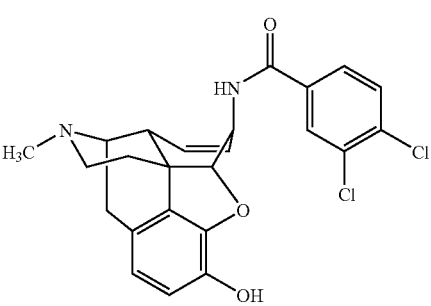 [SMILES: CN1CCC23c4c5ccc(O)c4OC2C(NC(=O)c2ccc(Cl)c(Cl)c2)C=CC3C1C5] | 0.1 ± 0.00 | 95.5 ± 10.5 | 1.3 ± 0.3 | 106.5 ± 11.5 | 0.03 ± 0.02 | 78.5 ± 1.5 |

TABLE 2-continued

Stimulation of $^{35}$S-GTP-γ-S binding by M6G derivatives

| | | mu | | delta | | kappa | |
|---|---|---|---|---|---|---|---|
| entry | cmpd | $EC_{50}$ | % stimulation | $EC_{50}$ | % stimulation | $EC_{50}$ | % stimulation |
| 13h | 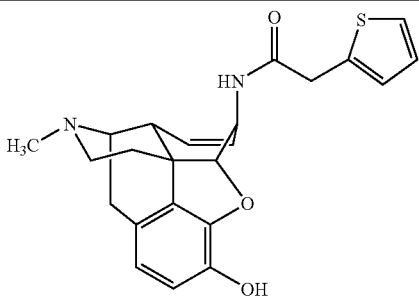 | 6.0 ± 2.1 | 95.8 ± 19.3 | 32.4 ± 2.1 | 57.3 ± 2.8 | 4.5 ± 0.2 | 98.0 ± 1.0 |
| 14 | 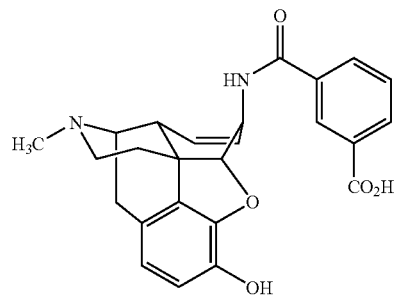 [SMILES: CN1CCC23c4c5ccc(O)c4OC2C(NC(=O)c2cccc(C(=O)O)c2)C=CC3C1C5] | 65.1 ± 21.8 | 71.0 ± 8.0 | 74.0 ± 12.7 | 69.5 ± 3.5 | 5096 | 71 ± 12 |

Example 29

Mu Receptor Internalization

A. Methods. Mu receptor internalization was evaluated according to the method of [D. E. Keith et al., *Mol. Pharm.*, 53:377-384 (1998)]. In general terms, this phenomenon was studied using flow cytometric analysis in which surface receptors can be quantified by staining with FITC-labeled FLAG M1 and measuring fluorescence. Drugs that were effective at causing internalization caused reduced staining relative to the control.

B. Results. Type III compounds were evaluated for their ability to effect mu receptor internalization because of the role this process may play in the development of tolerance and dependence (see Table 3). From the data, it can be seen that the dichloro compound 13g (47%) and the nitro compound 13f (59%) were both more effective than etorphine (61%) at causing mu receptor internalisation. The other amides were moderate to weak internalizers of the mu receptor. It should be pointed out that morphine (93%) does not cause mu receptor internalization at normal plasma concentrations (1-50 nM). The concentration of the compounds used in these experiments was 1 µM.

TABLE 3

Mu receptor internalization for selected ligands.

| entry | structure | % control |
|---|---|---|
| 13a | 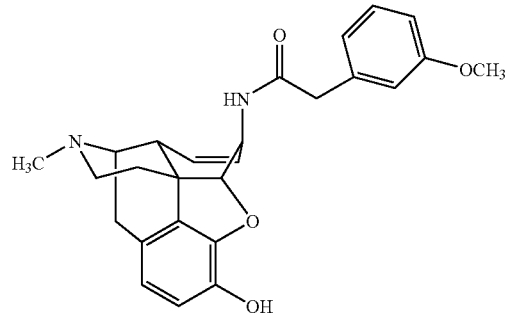 [SMILES: COc1cccc(CC(=O)NC2C=CC3C4Cc5ccc(O)c6c5C3(CCN4C)C2O6)c1] | 76.14 |

TABLE 3-continued

Mu receptor internalization for selected ligands.

| entry | structure | % control |
|---|---|---|
| 13b | 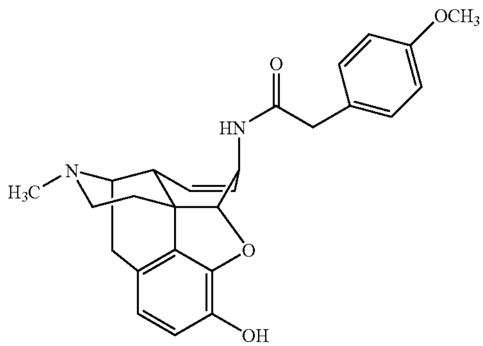 [SMILES: COc1ccc(CC(=O)NC2C=CC3C4Cc5ccc(O)c6c5C3(CCN4C)C2O6)cc1] | 84.84 |
| 13c | 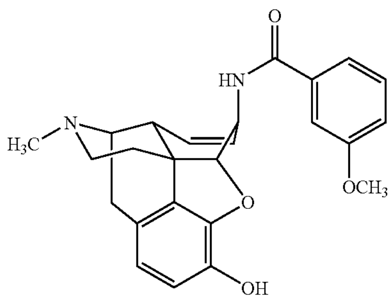 [SMILES: COc1cccc(C(=O)NC2C=CC3C4Cc5ccc(O)c6c5C3(CCN4C)C2O6)c1] | 74.53 |
| 13d | 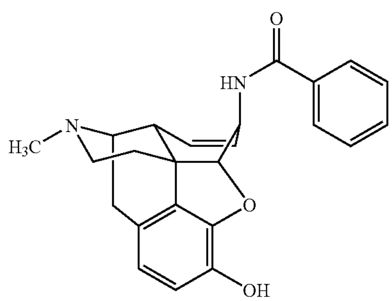 [SMILES: CN1CCC23c4c5ccc(O)c4OC2C(NC(=O)c2ccccc2)C=CC3C1C5] | 72.11 |
| 13e | 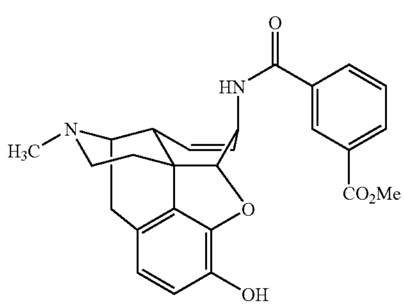 [SMILES: COC(=O)c1cccc(C(=O)NC2C=CC3C4Cc5ccc(O)c6c5C3(CCN4C)C2O6)c1] | 81.83 |
| 13f | 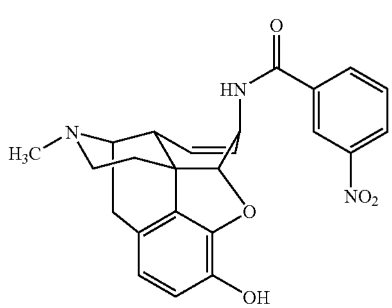 [SMILES: CN1CCC23c4c5ccc(O)c4OC2C(NC(=O)c2cccc([N+](=O)[O-])c2)C=CC3C1C5] | 58.69 |

TABLE 3-continued

Mu receptor internalization for selected ligands.

| entry | structure | % control |
|---|---|---|
| 13g | 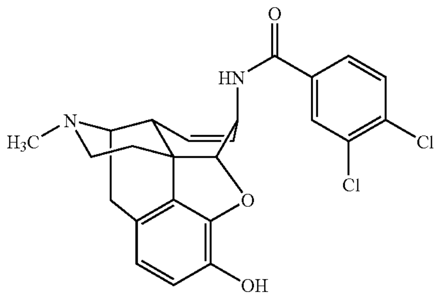 [SMILES: CN1CCC23c4c5ccc(O)c4OC2C(NC(=O)c2ccc(Cl)c(Cl)c2)C=CC3C1C5] | 47.11 |
| 13h | 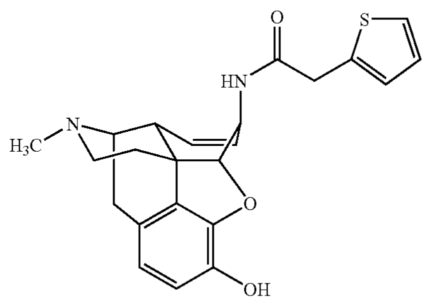 [SMILES: CN1CCC23c4c5ccc(O)c4OC2C(NC(=O)Cc2cccs2)C=CC3C1C5] | 91.11 |
| 14 | 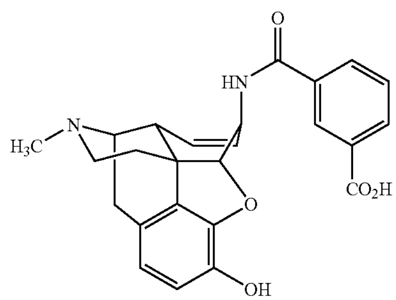 [SMILES: CN1CCC23c4c5ccc(O)c4OC2C(NC(=O)c2cccc(C(=O)O)c2)C=CC3C1C5] | 95.85 |

Example 30

Chemical and Metabolic Stability Evaluation

A. Methods. The chemical stability of selected compounds were examined at pH 7.4 and pH 2.0. Compounds (0.1 M) at either pH 7.4 or 2.0 in the presence of 10 uM potassium phosphate buffer were concentrated after 5 min, 1 h, 2 h, 3 h, 24 h, 48 h or 72 h. Then HPLC was used to analyze the decomposition of the starting material. The metabolic stability of selected compounds was examined in human liver S9 and microsomes. Human liver pooled S9 (HLS9) stability and mouse liver microsomes (MLM). Assay buffer contains 3.2 mg/mL HLS9 or 1.2 mg/mL MLM, 0.1 M potassium phosphate buffer (pH 7.4), 0.1 mM compounds, 0.5 mM NADP+, 0.5 mM glucose-6-phosphate, 5 U/mL glucose-6-phosphate dehydrogenase, 1 mg/mL DETAPAC, 7 mM $MgCl_2$ for a final incubation volume of 0.25 mL. After 0, 10, 25, 40 or 60 min the reactions were stopped by the addition of 1 mL $CH_2Cl_2$/IPA (3:1 v:v). After centrifugation, the extraction solvent (organic phase) was evaporated off with a nitrogen stream, resolved by 200 uL methanol, vortexed, centrifuged, transferred to HPLC vial inserts. HPLC was used to analyze the decomposition of the starting material by comparing area under the curve to at before addition of microsomes to the area under the curve at the given time interval (0, 10, 25, 40 or 60 min).

B. Results. Select type I and III compounds were evaluated in the presence of mouse liver microsomes (MLM), human liver microsomes S-9 (HLS9) and at pH 2 and 7.4 (see Table 4). A longer half-life is correlated with greater stability under the given conditions. In compounds of type I, the M6G sulfur analogue 4a showed equal stability to M6G in the presence of HLS9 and at pH 2 and 9. The presence of ester protecting groups reduced the stability of type 1 molecules. The stability of compound 3a to HLS9 is greater than compound 3b (17.86 min) suggesting that the 3-position acetate group is the most labile ester group in type 1 molecules. This hypothesis was verified by HPLC co-injection. No differences could be detected in the stabilities of deprotected compounds 4a-d Type III compounds were significantly more stable than type I compounds under all conditions tested. The presence of the methyl ester group in compound 13e reduced the stability of this compound to HLS9 and at pH 7.4 when compared to other type III compounds. Sufficient amounts of type II compounds could not be obtained for evaluation. The presence of ester protecting groups in type II compounds should render them less stable than type III compounds. The amide linkage is expected to impart improved stability over the S-glycosidic linkage.

TABLE 4

Stability analysis of selected ligands.

| entry | cmpd | MLM t 1/2 (min) | HLS9 t 1/2 (min) | pH 2.0 t 1/2 (min) | pH 7.4 t 1/2 (min) |
|---|---|---|---|---|---|
| morphine | | — | — | — | — |
| M6G | | stable | stable | stable | stable |
| 3a | | 16.74 | 17.86 | 835.6 | stable |
| 3b | | 39.95 | stable | stable | 94.1 h |

TABLE 4-continued
Stability analysis of selected ligands.
| entry | cmpd | MLM t 1/2 (min) | HLS9 t 1/2 (min) | pH 2.0 t 1/2 (min) | pH 7.4 t 1/2 (min) |
|---|---|---|---|---|---|
| 3c | 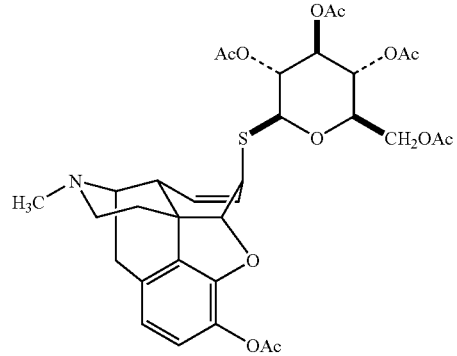 | 14.11 | 11.76 | — | — |
| 3d | 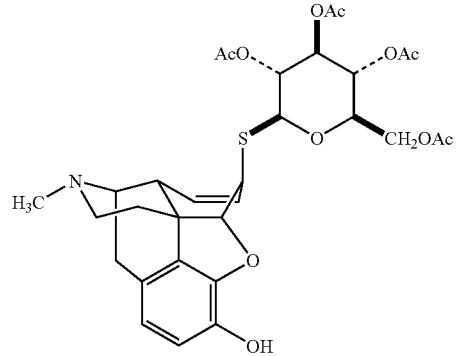 | 94.65 | 156.5 | — | — |
| 3e | 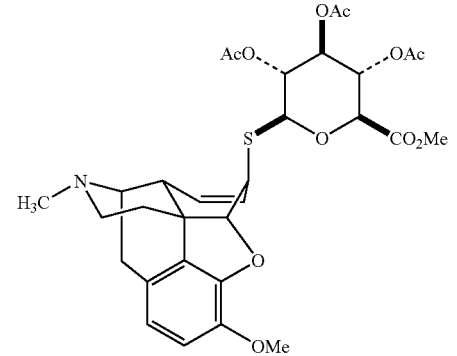 | ≦12.5 | 37.44 | 1042.0 | 51 h |
| 3f | 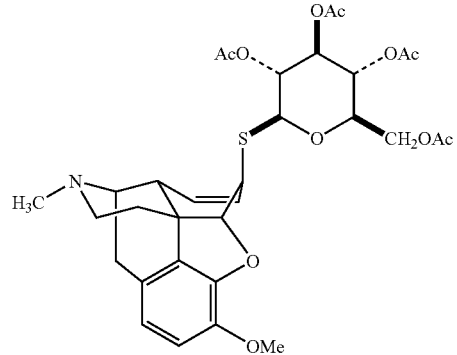 | 491.8 | 628.8 | | |

TABLE 4-continued
Stability analysis of selected ligands.
| entry | cmpd | MLM t 1/2 (min) | HLS9 t 1/2 (min) | pH 2.0 t 1/2 (min) | pH 7.4 t 1/2 (min) |
|---|---|---|---|---|---|
| 4a | 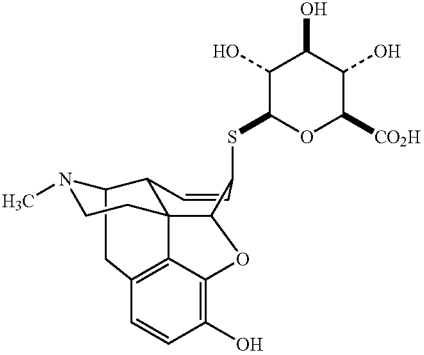 | stable | stable | stable | stable |
| 4b | 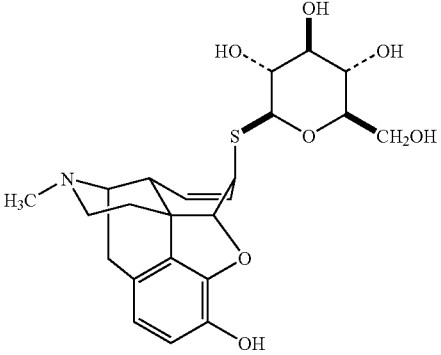 | stable | stable | — | — |
| 4c | 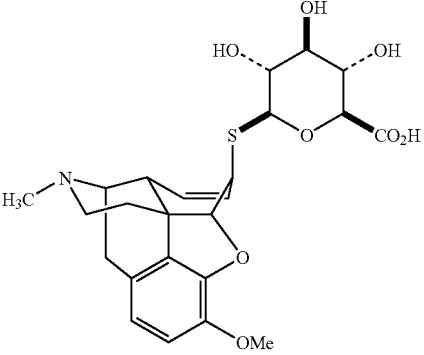 | stable | stable | — | — |
| 4d | 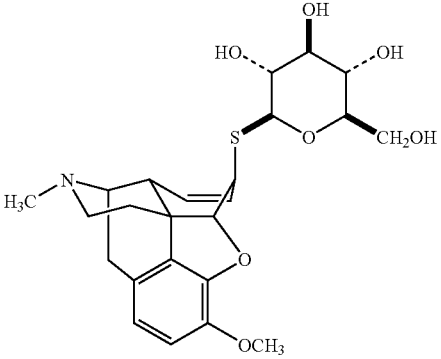 | stable | stable | — | — |

TABLE 4-continued

Stability analysis of selected ligands.

| entry | cmpd | MLM t 1/2 (min) | HLS9 t 1/2 (min) | pH 2.0 t 1/2 (min) | pH 7.4 t 1/2 (min) |
|---|---|---|---|---|---|
| 10 | | — | — | — | — |
| 11a | | — | — | — | — |
| 9b | | — | — | — | — |
| 11b | | — | — | — | — |
| 13a | | stable | stable | — | — |

TABLE 4-continued

Stability analysis of selected ligands.

| entry | cmpd | MLM t 1/2 (min) | HLS9 t 1/2 (min) | pH 2.0 t 1/2 (min) | pH 7.4 t 1/2 (min) |
|---|---|---|---|---|---|
| 13b | (structure with 4-methoxyphenylacetamide) | 310.2 | stable | — | — |
| 13c | (structure with 3-methoxybenzamide) | stable | stable | — | — |
| 13d | (structure with benzamide) | stable | stable | — | — |
| 13e | (structure with 3-CO₂Me benzamide) | stable | 202.8 | stable | 828.1 |

TABLE 4-continued

Stability analysis of selected ligands.

| entry | cmpd | MLM t 1/2 (min) | HLS9 t 1/2 (min) | pH 2.0 t 1/2 (min) | pH 7.4 t 1/2 (min) |
|---|---|---|---|---|---|
| 13f | (3-nitrobenzamide morphine analog) | 1123.5 | 361.1 | — | — |
| 13g | (3,4-dichlorobenzamide morphine analog) | stable | 231.4 | — | — |
| 13h | (2-thienylacetamide morphine analog) | 670.2 | stable | — | — |
| 14 | (3-carboxybenzamide morphine analog) | stable | stable | — | — |

Example 31

Determination of Analgesic Activity of Morphine Analogs 3a and 13e

A. Methods.

1. Animals. Male ICR mice weighing 20-25 g at the start of the experiment were used. Animals were group-housed under standard laboratory conditions and were kept on a 12:12 hr day-night cycle (lights on at 08:00). Animals were handled for 1-2 days prior to conducting the experiments.

2. Drugs. Morphine, 13e and 3b were dissolved in water. Drugs were injected at a volume of 0.1 ml.

3. Test for Nociception. Nociception was assessed using the tail flick assay with an analgesia instrument (Stoelting) that uses radiant heat. This instrument is equipped with an automatic quantification of tail flick latency, and a 15-sec cutoff to prevent damage to the animal's tail. During testing, the focused beam of light was applied to the lower half of the animal's tail, and tail flick latency was recorded. Baseline values for tail flick latency were determined before drug administration in each animal. Basal tail flick latency was between 3.2-8.0-sec (average 5.86±0.16 SEM). Immediately after testing, animals were injected subcutaneously with the test compound or saline as a vehicle control. Following injections, animals were tested for tail flick latencies at 30-, and 60-min post-injection.

4. Data Analysis. Antinociception was quantified by the following formula: % Antinociception=100*[(test latency−baseline latency)/(15−baseline latency)]. If the animal did not respond prior to the 15-s cutoff, the animal was assigned a score of 100%. Behavioral results were analyzed using ANOVAs with morphine, 13e, and 3b as between group variables and post-drug treatment time (30-, 60-min) as the repeated measure followed by Student Newman-Keuls post-hoc tests where appropriate. The level of significance was set at $p<0.05$.

B. Results.

Figure 5:
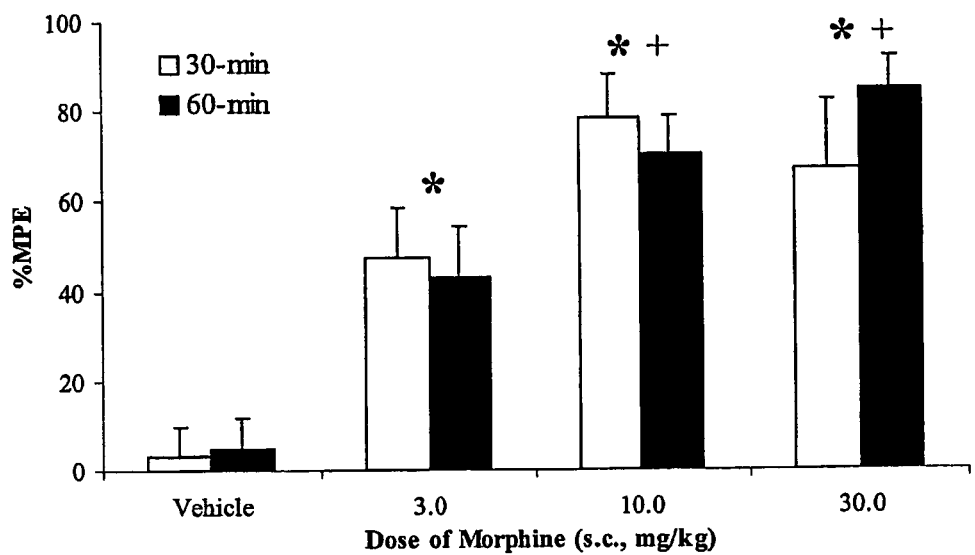
FIG. 5 depicts dose-dependent analgesia induced by administration of morphine. Data are mean % MPE (±SEM). Asterisks represent significant differences from vehicle controls (Student Newman-Keuls, $p<0.05$). Plus signs represent a significant difference from 3 mg/kg morphine (Student Newman-Keuls, $p<0.05$).

1. Effects of morphine on tail-flick latency. As shown in FIG. 5, morphine produced dose-dependent increases in tail-flick latency. The overall ANOVA indicated a significant effect of dose [$F(3,45)=25.52$, $P<0.0001$]. Thus, regardless of post-injection time, morphine produced the same effect on tail flick latency. Averaged across post-injection time, the 3-30 mg/kg dose of morphine produced a significant increase in tail-flick latency relative to controls (Student Newman-Keuls, $p<0.05$). An escalating dose response curve for % MPE was observed, where the 3 mg/kg dose of morphine produced analgesic effects to a lower degree relative to the 10 and 30 mg/kg doses (Student Newman-Keuls, $p<0.05$).

Figure 6:
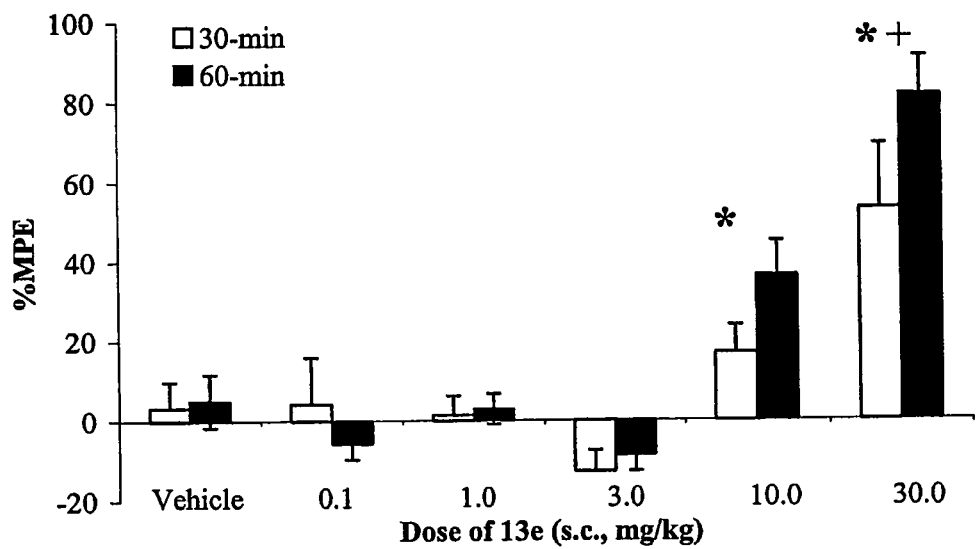
FIG. 6 analgesic effects produced by two high doses 13e. Data are mean % MPE (±SEM). Asterisks represent significant differences from vehicle controls (Student Newman-Keuls, $p<0.05$). Plus signs represent a significant difference between 10 and 30 mg/kg 13e (Student Newman-Keuls, $p<0.05$).

2. Effects of 13e on tail-flick latency. Administration of 13e produced an increase in tail-flick latency that was evident at 30 min and continued to be present at 60 min (see FIG. 6). The overall ANOVA indicated a significant effect of dose [$F(5, 72)=14.86$, $P<0.0001$]. Averaged across post-injection time, the two highest doses of 13e produced a significant increase in tail-flick latency relative to controls (Student Newman-Keuls, $p<0.05$). The analgesic effects of 30 mg/kg dose of 13e were 2-fold greater than that produced by the mg/kg dose (Student Newman-Keuls, $P<0.05$). Compound 13e seemed to have a slower onset of action than morphine, with significantly increased potency at 60 min over 30 min. Considering its very high affinity ($K_i=0.23$ nM at μ receptors) and potent full agonist activity with respect to stimulation of [$^{35}$S]GTPγS binding ($EC_{50}=2.4$ nM at μ), this compound had relatively weak antinociceptive activity, with ED50 values of 30.2 mg/kg and 12.6 mg/kg at 30 and 60 min respectively. This probably less short-term potency relative to morphine, which has an $ED_{50}$ of approximately 3 mg/kg.

Figure 7:
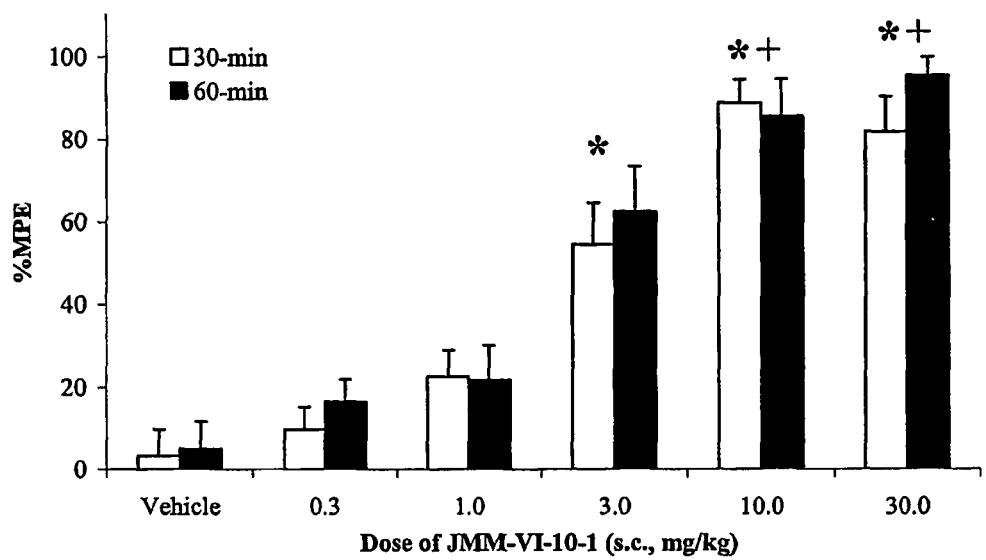
FIG. 7 depicts dose-dependent analgesia induced by administration of 3a. Data are mean % MPE (±SEM). Asterisks represent significant differences from vehicle controls (Student Newman-Keuls, $p<0.05$). Plus signs represent a significant difference from 3 mg/kg 3a (Student Newman-Keuls, $p<0.05$).
Figure 8A:
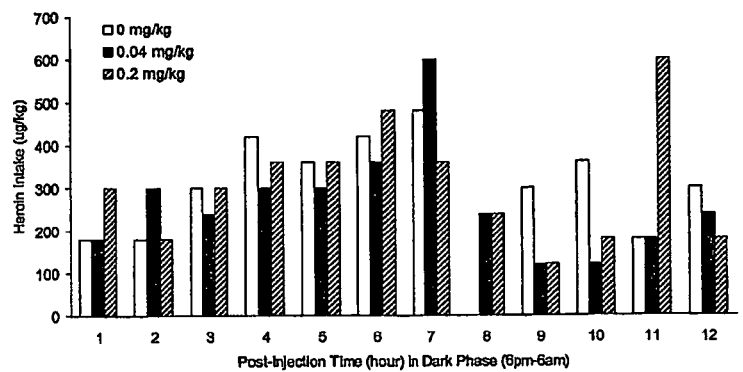
FIGS. 8A-C depict an effect of the opiate analog 13e on heroin intake in a heroin-dependent rat (Rat #96). Rats were injected in a within-subjects design with the opiate analog 13e (0, 0.04, and 0.2 mg/kg, s.c.) 15 mins prior (5:45 pm) to the active/dark phase (6 pm-6 am). Data are expressed as total heroin intake (60 µg/kg/0.1 ml infusion) for each hour (FIG. 8A), every 3 hours (FIG. 8B), and all 12 hours (FIG. 8C) in the dark phase.
Figure 8B:
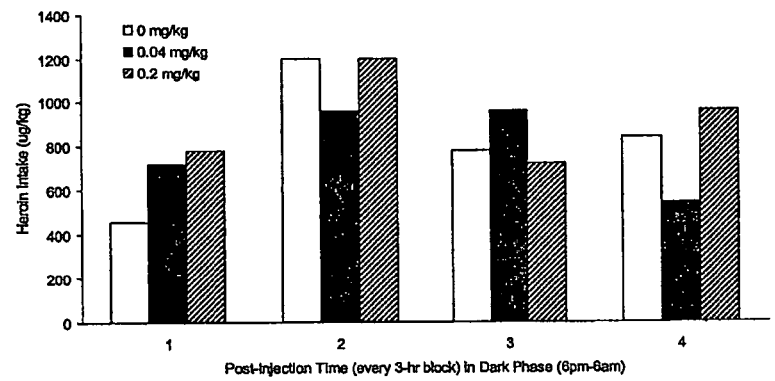
Figure 8C:
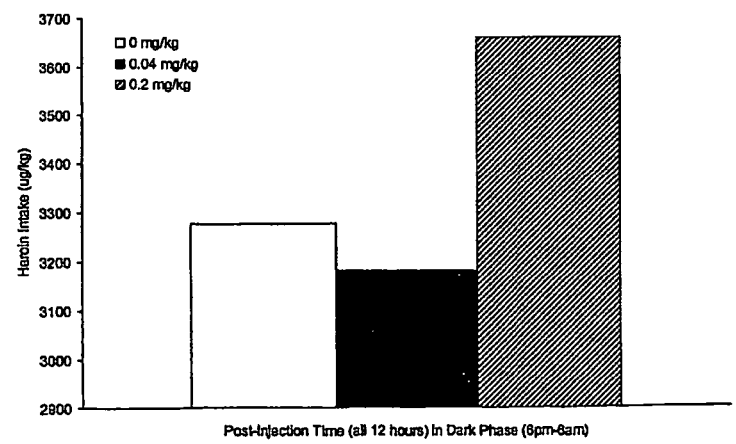
Figure 9A:
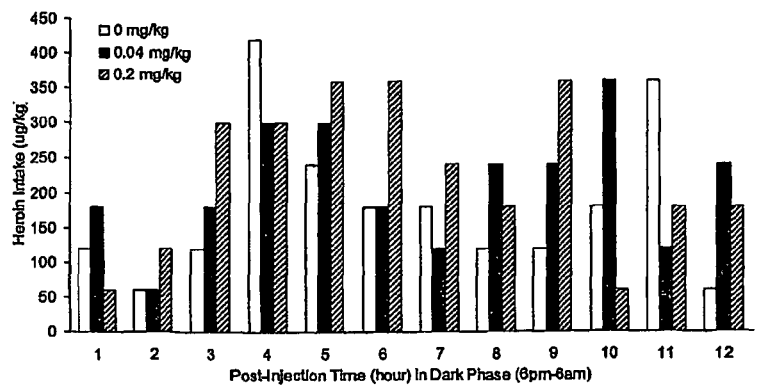
FIGS. 9A-C depict an effect of the opiate analog 3a on heroin intake in a heroin-dependent rat (Rat #99). Rats were injected in a within-subjects design with the opiate analog 3a (0, 0.04, and 0.2 mg/kg, s.c.) 15 mins prior (5:45 pm) to the active/dark phase (6 pm-6 am). Data are expressed as total heroin intake (60 µg/kg/0.1 ml infusion) for each hour (FIG. 9A), every 3 hours (FIG. 9B), and all 12 hours (FIG. 9C) in the dark phase.
Figure 9B:
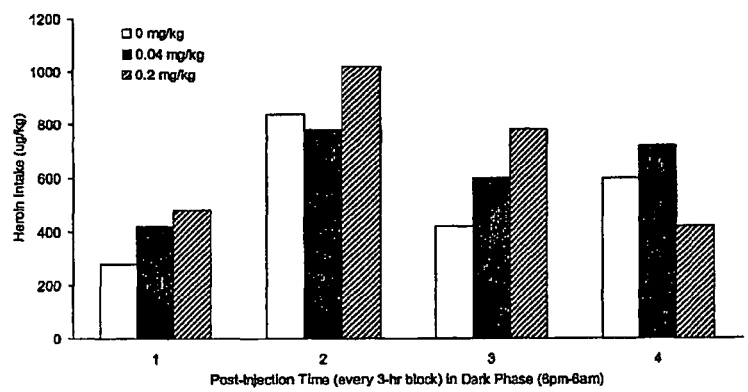
Figure 9C:
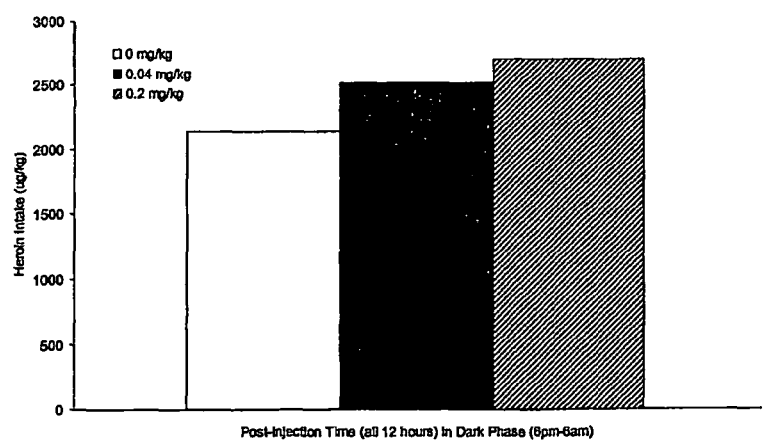
Figure 10A:
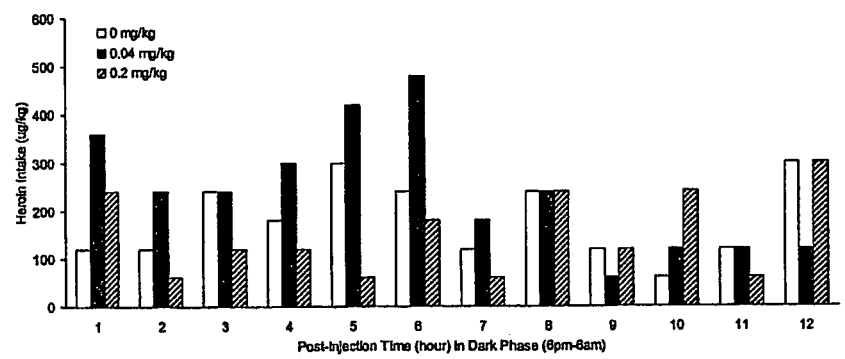
FIGS. 10A-C depict an effect of the opiate analog 13g on heroin intake in a heroin-dependent rat (Rat #100). Rats were injected in a within-subjects design with the opiate analog 13g (0, 0.04, and 0.2 mg/kg, s.c.) 15 mins prior (5:45 pm) to the active/dark phase (6 pm-6 am). Data are expressed as total heroin intake (60 µg/kg/0.1 ml infusion) for each hour (FIG. 10A), every 3 hours (FIG. 10B), and all 12 hours (FIG. 10C) in the dark phase.
Figure 10B:
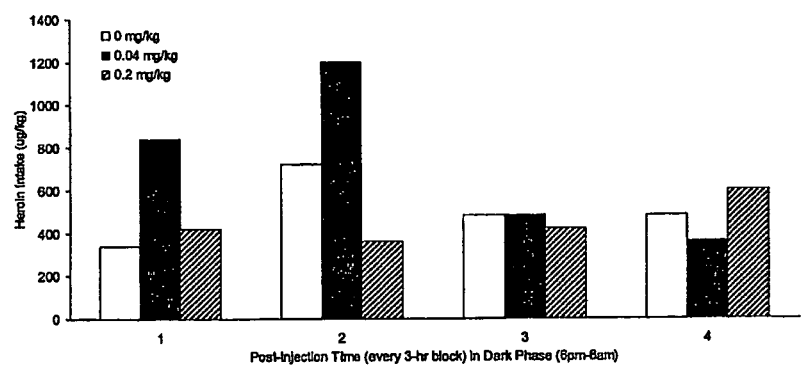
Figure 10C:
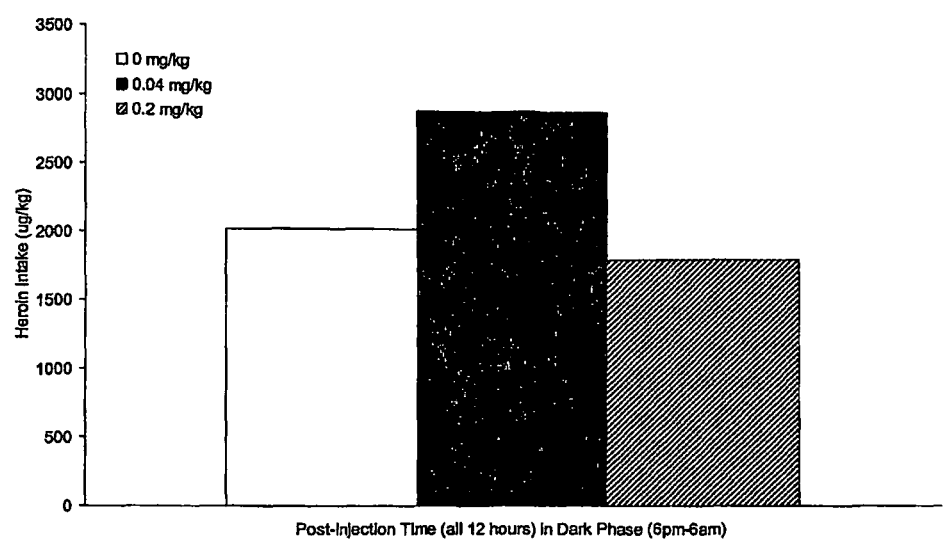
Figure 11A:
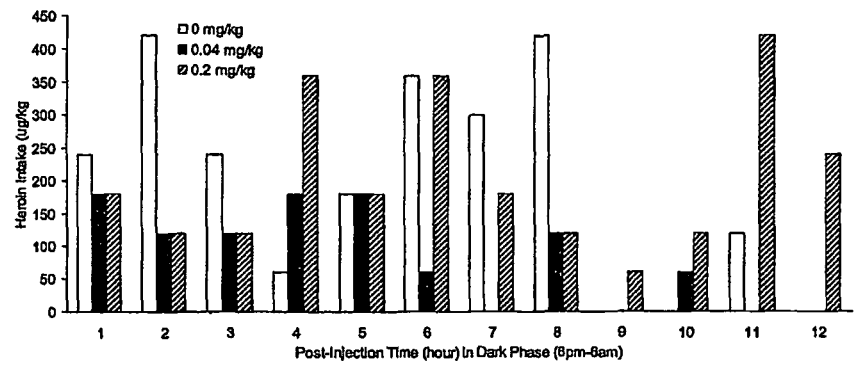
FIGS. 11A-C depict an effect of M6G on heroin intake in a heroin-dependent rat (Rat #103). Rats were injected in a within-subjects design with M6G (0, 0.04, and 0.2 mg/kg, s.c.) 15 mins prior (5:45 pm) to the active/dark phase (6 pm-6 am). Data are expressed as total heroin intake (60 µg/kg/0.1 ml infusion) for each hour (FIG. 11A), every 3 hours (FIG. 11B), and all 12 hours (FIG. 11C) in the dark phase.
Figure 11B:
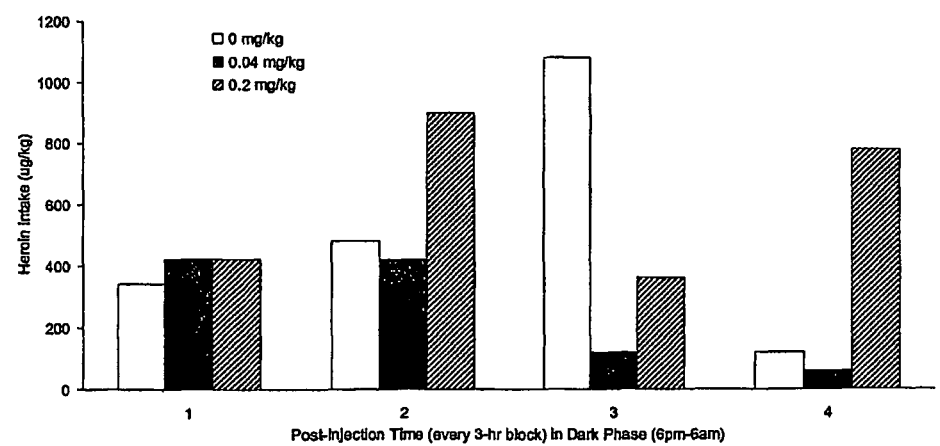
Figure 11C:
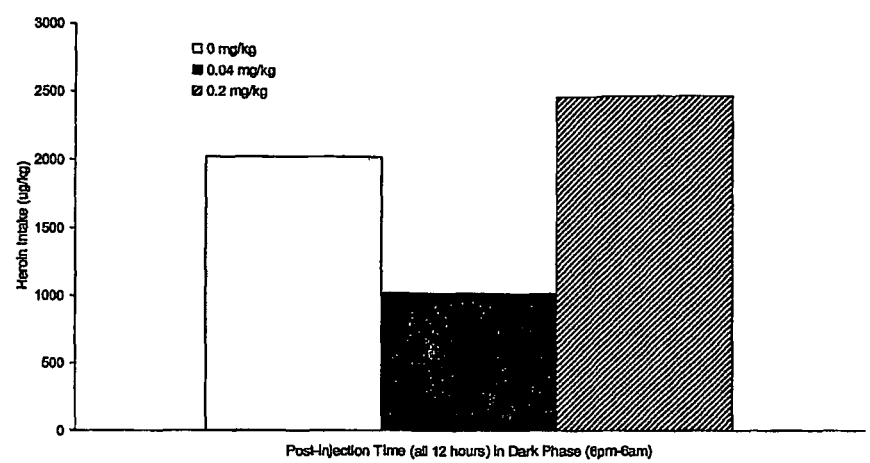
Figure 12A:
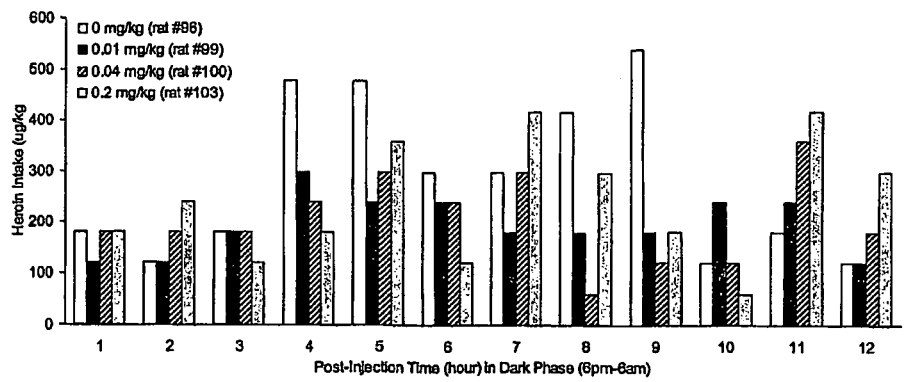
FIGS. 12A-C depict an effect of the opiate analog 13 h on heroin intake in heroin-dependent rats (n=4). Rats were injected in a between-subjects design with the opiate analog 13 h (0 [Rat #96], 0.01 [Rat #99], 0.04 [Rat #100], and 0.2 mg/kg [Rat #103], s.c.) 15 mins prior (5:45 pm) to the active/dark phase (6 pm-6 am). Data are expressed as total heroin intake (60 µg/kg/0.1 ml infusion) for each hour (FIG. 12A), every 3 hours (FIG. 12B), and all 12 hours (FIG. 12C) in the dark phase.
Figure 12B:
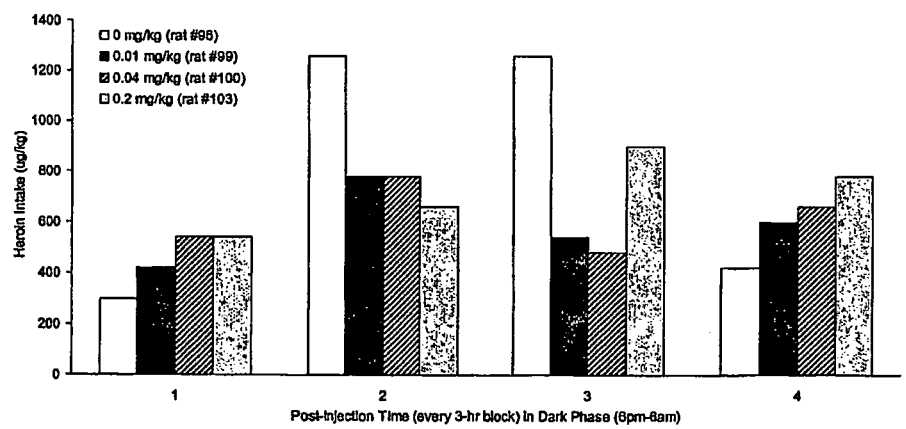
Figure 12C:
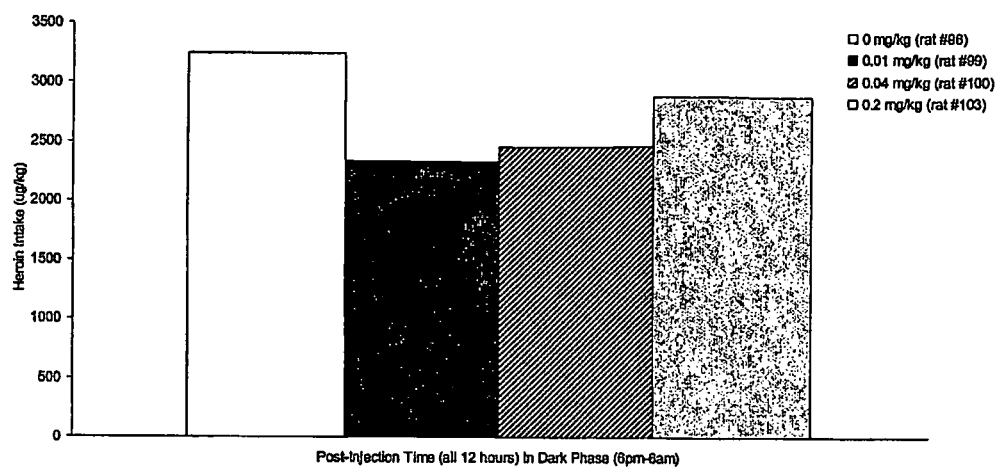
Figure 13:
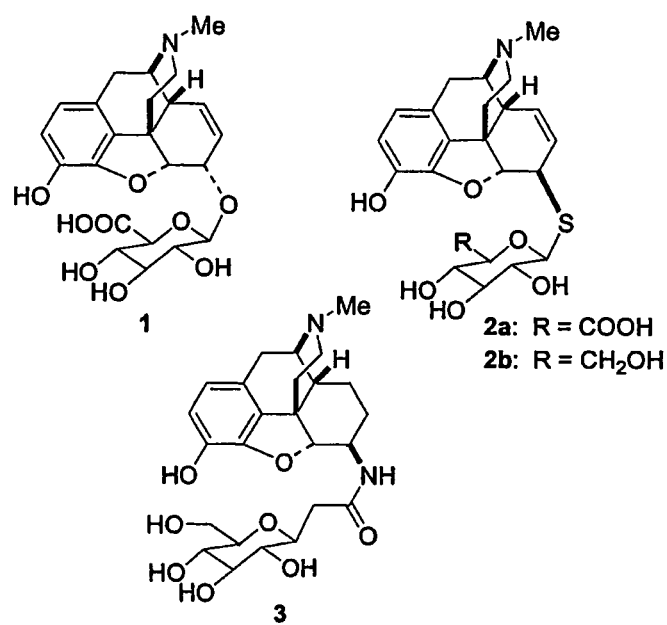
FIG. 13 depicts chemical structures of MG6 (1) and two metabolically stable analogs (2 and 3) described in Example 33.
Figure 14:
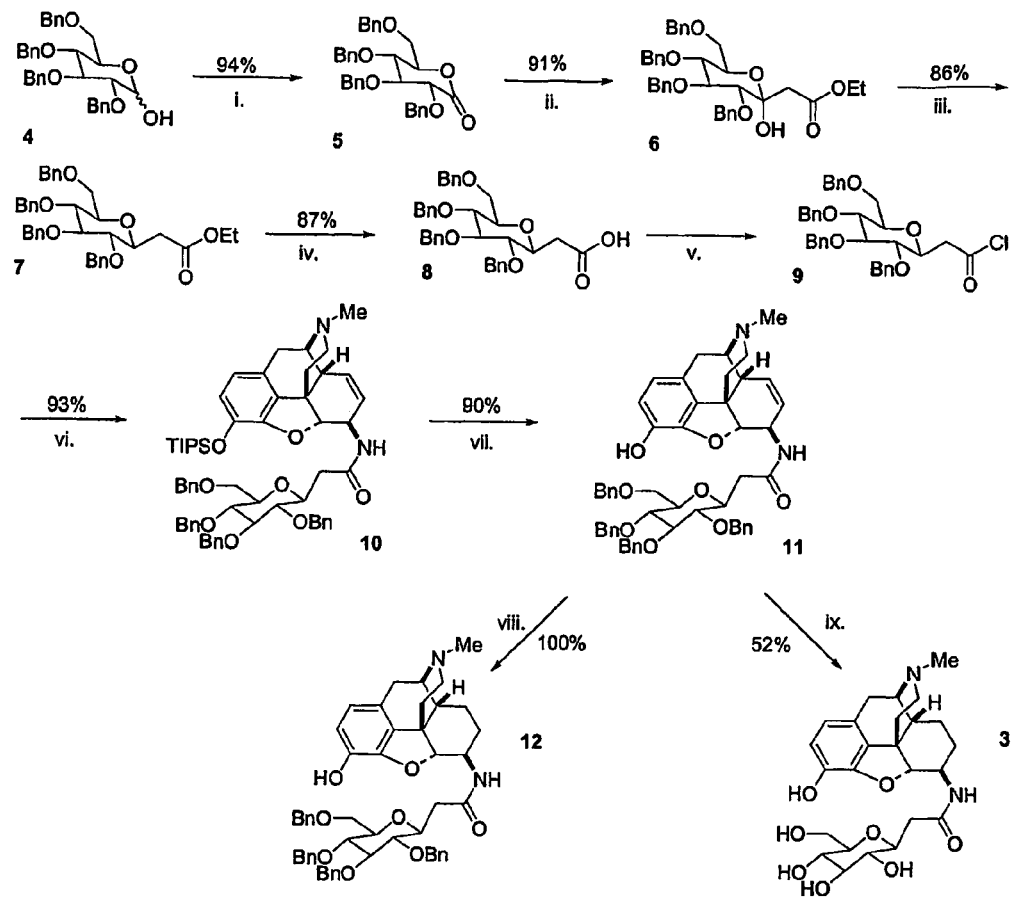
FIG. 14 depicts the preparation of the C-glycosides of MG6 described in Example 33. (i) $CH_3S(O)CH_3$, $Ac_2O$; (ii) $LiCH_2CO_2Et$, THF then HCl, $-78°$ C. to rt; $Et_3SiH$, $BF_3"OEt_2$, $CH_3CN$, $0°$ C. to rt; (iv) NaOH, $H_2O$, THF, reflux then HCl; (v) $SOCl_2$; (vi) 3-O-triisopropylsilyl-6-β-aminomorphine, $Et_3N$, $CH_2Cl_2$; (vii) $B_{u4}NF$, THF, $H_2O$; (viii) $H_2$, 10% Pd—C, MeOH; (ix) $H_2$, 10% Pd—C, MeOH, HCl.

3. Effects of 3a on tail-flick latency. Administration of 3a produced a dose-dependent increase in tail-flick latency indicative of the strong analgesic effects of the compound (see FIG. 7). The overall ANOVA indicated a significant effect of dose [$F(5,64)=37.26$, $P<0.0001$]. Averaged across post-injection time, the 3-30 mg/kg doses of 3a produced a significant increase in tail-flick latency relative to controls (Student Newman-Keuls, $p<0.05$). The two highest doses (10 and 30 mg/kg) of 3a produced a greater amount of analgesia relative to the 3 mg/kg dose (Student Newman-Keuls, $p<0.05$). Compound 3a was significantly more potent as an analgesic than 13e, with an $ED_{50}$ of approximately 2.5 mg/kg at both 30 and 60 min. This value also suggests that 3a is slightly more potent morphine (ED50 of 3 mg/kg). Although 3a has slightly lower in vitro binding affinity than morphine, it has roughly similar [$^{35}$S]GTPγS potency and percent stimulation (see tables 1 and 2), indicating that the bioavailability of 3a is also similar to that or greater than that of morphine. Because this compound is somewhat non-selective with respect to each of the opioid receptors, it is not certain at this point which receptor mediates the antinocieptive activity. The onset of action for 3a is apparently faster than that for morphine (the activity is greater for the 60-min rather than 30 min time point).

Example 32

Heroin Dependence and Withdrawal

A. Methods. Effects of M6G Analogs on Heroin Dependent Animals. Heroin self-administration was done using a dose of heroin that produced optimal measures of dependence. 0.06 mg/kg/0.1 ml infusion was estimated based upon previous work. After stable responding was established (approx. 40 days at 23 hour/day access), the effects of low doses of naloxone (0.05 to 0.2 mg/kg) as a positive control and M6G analogues (0, 0.01, 0.04, 0.1 mg/kg, s.c.) and other analogs on different behavioral measures of heroin intake were examined. Four doses were tested for each compound. An attempt was made to perform within-subjects dose-effect studies for each M6G analog, but studies also employed between-subjects dose-effect functions as needed. To explore the effects of naloxone and M6G analogs over a 12-hr period, a minipump connected to an on/off gating device developed in the Koob lab can also be used. Once stable heroin intake was achieved, the rats can be implanted with an osmotic minipump (in a gated-off position) at 6 AM. Twelve hours later, the gating device is turned to the on position and the rats are allowed access to heroin self-administration during the usual 23-hr sessions. During these sessions the minipump was in the gated-on position for a duration of 12 hours during the dark period which is the active phase (6 PM on 6 PM off). After 2 days, the minipump was removed and replaced with another minipump containing a different dose of the test compound (i.e., naloxone or M6G analog) in a Latin Square design. This cycle is repeated so that 3 doses and vehicle control are tested. The large number of drugs and doses required may force a between-subjects design of dose for naloxone and M6G analogs. The particular behaviors to be examined were determined from the results from tests of long term heroin exposure via self-administration that may reflect the transition from self-administration in a non-dependent pattern to self administration in a dependent pattern. Sophisticated statistical modeling was done by using a Hiearchical Linear Modeling approach where individual acquisition trajectories were fitted with a polynomial function while accounting for within-subject and between-subject variables.

B. Results. Heroin self-administration paradigms are now well-established in the rat. [See Walker et al., *Eur. J. Pharmacol.*, 383:115 (1999)]. Fewer studies have explored the change in behavior associated with unlimited access to heroin and the development of self-administration of heroin to the point of dependence. Preliminary results have established that rats will reliably self-administer heroin i.v. with unlimited access, under conditions of no food deprivation or restriction. The pattern of unlimited access self-administration changes over time and produces animals that exhibit measures of dependence. An animal model of the development of heroin dependence in humans was developed. Animals given extended access (23-hour access to heroin self administration at doses of 0.06 mg/kg/0.1 ml infusion) exhibited sustained intake of heroin for 50-60 days. During this period, the self-infusion pattern changed from one observed only in the "active/dark" phase to a pattern where self-administration occurred about every 15-20 mins. From weeks 2-3 to week 7 essentially uniform self-administration was observed. Each self-administration per day was recorded for about 50 days. These studies have provided full information about heroin doses, patterns of intake, and time of day for maximal drug intake. Heroin dependence can be measured as a manifestation of withdrawal from chronic heroin administration. [See Woolverton and Schuster (1983)]. Dependence can be expressed as overt withdrawal signs following the removal of heroin or following administration of a heroin antagonist in dependent rats. Both produce somatic signs and motivational effects. [See Weeks and Collins (1964).] The ability of M6G analogs to decrease heroin self-administration was tested in the extended-access model during self-administration and after administration of M6G analogs.

The effect of M6G analogs 3a, 13e, 13g and 13h on self-administration of heroin was examined in dependent rats that are consistent with effects in humans dependent on heroin. The goal of these experiments was to identify M6G analogs that were efficacious at decreasing heroin self-administration. Examination of FIGS. 8-12 reveals that M6G analogs 13e (0.04 mg/kg), 13g (0.2 mg/kg), M6G (0.04 mg/kg), 13h (0.01, 0.04, 0.2 mg/kg) were effective at reducing heroin self-administration. The most effective compound was 13h which reduced heroin intake by 1000 ug/kg at a dose of 0.01 mg/kg.

Example 33

Synthesis and Biological Evaluation of a C-glycoside Analog of MG6

Morphine-6-glucuronide (M6G) is a phase II metabolic conjugate of morphine with approximately 100-fold the analgesic potency of morphine itself when injected intracerebroventricularly into rats. [Carrupt et al., *J. Med. Chem.* 34, 1272-1275 (1991)] M6G is currently in late stage clinical trials for the treatment of postoperative pain. [Gutman et al., U.S. Pat. No. 6,737,518 (2004)] The oral bioavailability of M6G is only 11% [Penson et al., *Br. J. Clin. Pharmacol.*, 53:347-354 (2002)] and improvement of the metabolic stability of M6G could possibly increase its effectiveness as a potential pain medication. A general strategy for improving the in vivo metabolic stability of glycoconjugates involves the replacement of the glycosidic oxygen atom with carbon, nitrogen or sulfur atoms. [Postema et al., *Organic Lett.*, 5:1721-1723 (2003); Kiefel et al., *J. Carbohydr. Chem.*, 18:937-959 (1999).] This strategy in designing a library of glucosyl and glucuronosyl analogues of M6G, in which the glycosidic oxygen atom was replaced with a sulfur atom, was previously employed. [MacDougall et al., *J. Med. Chem.* 47:5809-5815 (2004).] The 6-β sulfur analogues of M6G showed modest improvement in μ opioid receptor affinity and functional efficacy, but showed less selectivity for μ versus δ and κ opioid receptors. Reported herein is an extension of this work detailing the results of a 14-step synthetic route and biological evaluation of a novel, p-selective, amide-linked carbon glycoside analogue of M6G.

The C-β-glycopyranosyl acyl chloride 9 was prepared by a five step procedure from commercially available 2,3,4,6-tetrabenzylglucopyranose 4. Compound 4 was oxidized with DMSO/Ac$_2$O to provide the corresponding lactone 5 (94%). [Kuzuhara, H.; Fletcher, H. G., *J. Org. Chem.*, 32:2531-2534 (1967).] Addition of 5 to a −78° C. THF solution of lithium ethyl acetate [Rathke, M. W., *J. Am. Chem. Soc.*, 92:3222-3223 (1970)], followed by acidic aqueous workup afforded the hemiketal 6, that was formed by a stereoselective aldol reaction (91%). [Lewis et al., *J. Am. Chem. Soc.*, 104:4976-4978 (1982).] The reduction [Lewis et al., supra; Tiedemann et al., *J. Org. Chem.*, 64:4030-4041 (1999)] of 6 with triethylsilane in the presence of BF$_3$□OEt$_2$ in acetonitrile at 0° C. gave the ethyl ester 7 (86%). Hydrolysis of the ethyl ester group of 7 with LiOH in 1:1 THF/H$_2$O at reflux and subsequent acidic aqueous workup gave the carboxylic acid 8 (87%). The conversion of 8 to the corresponding acyl chloride 9 was accomplished by stirring in neat thionyl chloride for 18 h. Addition of 1.5 equivalents of the crude acid chloride 9 to 3-triisopropylsilyl-6-O-aminomorphine [MacDougall et al., *Bioorg. Med. Chem.*, 12:5983-5990 (2004)] in CH$_2$Cl$_2$ in the presence of 2.0 equivalents of Et$_3$N gave the protected morphine glucose analogue 10 (93%). The triisopropylsilyl protecting group in 10 was removed by the addition of TBAF in THF to give the phenol 11 (90%). Subsequent catalytic hydrogenation of 11 with activated 10% Pd/C in acidic methanol gave the amide-linked C-β-glycopyranoside analogue of M6G, compound 3 (52%). Hydrogenolysis of 11 with Pd/C in the absence of HCl resulted in the reduction of the phenanthrene carbon double bond and afforded 12 in quantitative yield, but did not result in hydrogenolysis of the glucose benzyl ether groups. Under these conditions, the basic morphinan nitrogen atom in 11 likely inhibited O-debenzylation. [Czech, B. P.; Bartsch, R. A., *J. Org. Chem.* 49:4076-4078 (1984).] It is known that both saturation of the 7,8-double bond and substitution of the glucuronic acid moiety with a glucose moiety provide analogues of M6G with increased analgesic potency. [Stachulski et al., *Bioorg. Med. Chem. Lett.*, 13:1207-1214 (2003).] Accordingly, compound 3 was evaluated directly rather than develop an alternate route to the corresponding dehydro analogue or the glucuronic acid analogue of 3. The spectral data for all the synthetic compounds was in full agreement with the assigned structures. [New compounds 10, 11, 12 and 3 were characterized by $^1$H NMR, $^{13}$C NMR and MS. The purity of test compounds 3 and 11 was determined by HPLC and was found to be ≧98%.]

The IC$_{50}$ values obtained from competition binding assays with . μ, δ and κ opioid receptors for compounds 3 and 11 were converted into K$_i$ values as described in the Experimental section. The K$_i$ values for the test compounds and reference materials are listed in Table 5. In the binding assays the following radioligands were used: [$^3$H]DAMGO (μ opioid receptor agonist); [$^3$H]U69593 (κ opioid receptor agonist); [$^3$H]DPDPE (δ opioid receptor agonist). K$_i$ values were determined from measuring the inhibition of binding of these radioligands to the receptor by the test compounds 3 and 11. [Zaveri et al., *Eur. J. Pharmacol.*, 428:29-36 (2001)] The benzyl derivative 11 and the deprotected congener 3 were both μ receptor selective. Compared to M6G, compound II possessed 27-fold higher potency than M6G for the μ opioid receptor. The selectivity of compound II for the μ versus δ and μ versus κ receptors were 10-fold and 34-fold, respectively. Compared to M6G, compound 3 showed 3.7-fold greater potency for the μ opioid receptor. The selectivity of compound 3 for the μ versus δ; and μ versus κ receptors was 77- and 166-fold, respectively. It is noteworthy that the μ versus δ but not μ versus κ receptor selectivity of compound 3 was considerably improved relative to the value for M6G (i.e., 12.5- and 316-fold selectivity, respectively). Compound 3 showed slightly greater potency toward the p, receptor compared to thiosaccharides 2a (2.5-fold) and 2b (1.6-fold) and significantly improved δ/μ, and κ/μ receptor selectivity ratios. The functional activity of compounds 3 and 11 was evaluated using the [$^{35}$S]GTPγS assay. [Traynor, J. R. and Nahorski S. R. Modulation, *Mol. Pharmacol.* 47:848-854 (1995)]. The [$^{35}$S]GTPγS assay measures the ability of the test compound to activate the G protein associated with either the μ, δ or κ opioid receptor. Based on the E$_{max}$ values for stimulating [$^{35}$S]GTP-γ-S binding, compound 3 was determined to be a full agonist at the μ and δ receptors and a partial agonist at the κ receptor. Compound II was determined to be a full agonist at the δ receptor and a partial agonist at the μ and κ receptors. The efficacy ($E_{max}$) of compound 3 at the μ receptor (75%) was substantially higher than M6G (45%) and the thiosaccharide analogues 2a (46.6%) and 2b (36.0%), respectively.

In conclusion, the C-glycoside 3 was prepared by a 14-step convergent synthesis from 2,3,4,6-tetra-O-benzyl-D-glucose 4 and morphine sulfate. Compound 3 showed a 3.7-fold greater affinity for the μ opioid receptor compared to M6G. The selectivity ratios of compound 3 for the δ versus μ and κ versus μ receptors were 76.7 and 166, respectively. The δ/μ selectivity for compound 3 was significantly improved relative to the value for M6G which was 12.5. Further work is currently in progress to fully delineate the in vivo biological properties of these compounds. Increasing metabolic stability of M6G may provide a new class of longer-lived, potent opioids agonists.

TABLE 5

Competitive inhibition of μ, δ and κ opioid receptors by compounds 2a, 2b, 3 and 11.

| entry | $K_i$ (nM) ± SEM[a] | | | Receptor selectivity | |
|---|---|---|---|---|---|
| | μ | δ | κ | δ/μ | κ/μ |
| M6G[b] | 12.9 ± 0.9 | 170 ± 1 | 4060 ± 230 | 12.5 | 316 |
| 2a[b] | 8.7 ± 0.9 | 31.4 ± 2.3 | 288 ± 12 | 3.6 | 33 |
| 2b[b] | 5.4 ± 0.8 | 56.2 ± 2.2 | 136 ± 17 | 10.4 | 25.4 |
| 3 | 3.47 ± 0.37 | 266.33 ± 47.27 | 574.9 ± 7.8 | 76.7 | 166 |
| 11 | 0.47 ± 0.15 | 7.18 ± 1.2 | 15.82 ± 0.44 | 10.3 | 33.7 |

[a]SEM, standard error of the mean. Each value is the mean of at least three independent determinations ± SEM.
[b]Data taken from MacDougall et al., supra.

TABLE 6

Stimulation of [$^{35}$S]-GTP-γ-S binding by compounds 2a, 2b, 3 and 11 mediated by the μ, δ and κ opioid receptors

| | μ | | δ | | κ | |
|---|---|---|---|---|---|---|
| entry | $EC_{50}$[a] | $E_{max}$[b] | $EC_{50}$ | $E_{max}$ | $EC_{50}$ | $E_{max}$ |
| M6G[d] | 72.3 ± 26.7 | 45.0 ± 5.0 | 190 ± 20 | 80.0 ± 1.0 | >10K | ND[c] |
| 2a[d] | 90.6 ± 22.9 | 46.6 ± 10.1 | 50.1 ± 36.7 | 78.7 ± 0.9 | NA[c] | ND[c] |
| 2b[d] | 91.5 ± 23.4 | 64.5 ± 0.5 | 192 ± 15 | 51.5 ± 6.5 | 321 ± 93 | 42.5 ± 2.5 |
| 3 | 37.2 ± 0.5 | 75.2 ± 3.6 | 334.9 ± 123.2 | 73.95 ± 7.85 | 1717.5 ± 24.5 | 38.5 ± 5.5 |
| 11 | 622.6 ± 9.2 | 36.0 ± 11.2 | 2.17 ± 1.14 | 65.35 ± 1.85 | 1.81 ± 0.62 | 44.5 ± 16.3 |

[a]$EC_{50}$: The $EC_{50}$ value represents the concentration of a compound that produced 50% stimulation of [$^{35}$S]GTPγS binding.
[b]$E_{max}$: Agonist efficacy is defined as the degree to which the compound maximally stimulates [$^{35}$S]GTPγS binding relative to control.
[c]ND: No detectable activity.
[d]Data from reference 6.

General information. All reactions were run under a positive pressure of dry nitrogen with magnetic stirring at ambient temperature using oven-dried glassware unless otherwise indicated. Air- and moisture-sensitive liquids were transferred via syringe through rubber septa. The term brine refers to a saturated solution of sodium chloride. Silica gel (230-400 mesh) was used for column chromatography. DMF was dried through a column of neutral alumina and stored over activated 4 Å molecular sieves under nitrogen prior to use. $CH_2Cl_2$ and THF were distilled from $CaH_2$ immediately prior to use. All other solvents and reagents were used as received. $^1$H NMR spectra were recorded at 18° C. with a 300 MHz Varian NMR. Chemical shifts were reported in ppm (δ) relative to $CDCl_3$ at 7.26 ppm unless indicated otherwise. High-resolution mass spectra was done on a VG 7070 spectrometer with Opus V3.1 and DEC 3000 Alpha Station data system at the University of California at Riverside. Low resolution mass spectroscopy (LRMS) was done on a Hitachi M-8000 3DQMS (ion trap) mass spectrometer using ESI. Melting points were reported uncorrected. Analytical purity was determined by straight phase HPLC using a Hitachi L74 liquid chromatograph with a D7500 integrator and a Hamilton PRP-I stainless steel column (250 mm×4.6 mm, i.d.). For determination of analytical purifies a mobile phase A=60/40/0.02 MeOH/2-propanol/$HClO_4$ (v:v) or mobile phase B=55/45/0.018 MeOH/2-propanol/$HClO_4$ (v:v) was used.

3-O-Triisopropylsilyl-6-β-(2,3,4,6-Tetra-O-benzyl-β-D-glucopyranosypacetamidomorphine 10. $SOCl_2$ (2.0 mL) was added to the carboxylic acid 8 (389 mg, 0.67 mmol) and the solution was stirred at rt for 18 h. The excess $SOCl2$ was removed under high vacuum with the aid of a water bath (60° C.) and the yellow oil that resulted was dissolved in $CH_2Cl_2$ (5 mL) and added to 3-O-triisopropylsilyl-6-β-aminomorphine (196 mg, 0.445 mmol) and $Et_3N$ (0.12 mL, 0.89 mmol) in $CH_2Cl_2$ (5 mL). The solution was stirred at rt for 1 h, concentrated and purified by flash chromatography ($SiO_2$, 30:1 to 10:1 EtOAc/MeOH), providing 10 as a white solid (417 mg, 93%): $R_f$=0.46 (10:1 $CH_2Cl_2$/MeOH); mp=56.6° C.; $^1$H NMR ($CDCl_3$) δ 7.35-7.10 (20H), 6.59 (d, J=8.0 Hz, 1H), 6.40 (d, J=8.0 Hz, 1H), 6.22 (d, J=6.9 Hz, 1H), 5.71 (ddd, J=3.0, 6.0, 9.5 Hz, 1H), 5.41 (dd, J=1.9, 9.5 Hz, 1H), 4.89-4.48 (9H), 4.36 (t, J=6.3 Hz, 1H), 3.72-3.46 (5H), 3.29 (t, J=9.0 Hz, 1H), 3.17 (dd, J=3.0, 5.2 Hz, 1H), 2.96 (d, J=18.7 Hz, 1H), 2.88 (bs, 1H), 2.72 (dd, J=2.7, 15.2 Hz, 1H), 2.50-1.72 (10H), 1.30-1.05 (21H). $^{13}$C NMR ($CDCl_3$) δ 170.0, 147.9, 143.6, 138.2, 137.8, 137.6, 132.9, 130.4, 128.7, 128.4, 128.34, 128.32, 128.0, 127.8, 127.76, 127.6, 127.0, 120.8, 118.4, 92.0, 86.8, 80.9, 78.7, 78.1, 77.4, 76.1, 75.7, 75.2, 75.0, 73.3, 68.7, 59.0, 49.3, 46.8, 44.1, 43.1, 40.3, 39.0, 36.4, 20.3, 18.0, 17.99, 12.8, 11.3; MS (EI) m/z 1006 [M+H]$^+$.

6-β-(2,2,4,6-Tetra-O-benzyl-β-D-glucopyranosypacetamidomorphine 11. The silyl ether 10 (270 mg, 0.27 mmol) was dissolved in THF (4 mL). Water (0.05 mL) and TBAF (0.4 mL, 0.4 mmol, 1.0 M solution in THF) were added. After 2.5 h, 1% concentrated HCl (4 mL) was added and the mixture was stirred for 2 min, diluted with water (10 mL) and made basic with solid $NaHCO_3$. The mixture was extracted with $CH_2Cl_2$ (5×30 mL), dried ($Na_2SO_4$), filtered and concentrated. Flash chromatography (24:1 to 12:1 EtOAc/MeOH) provided 11 as a white solid (205 mg, 90%): $R_f$=0.15 (12:1 EtOAc/MeOH); mp=103.8° C.; $^1$H NMR δ 7.34-7.10 (20H), 6.64 (d, J=8.2 Hz, 1H), 6.46 (d, J=8.2 Hz, 1H), 6.34 (d, J=6.3 Hz, 1H), 5.68 (ddd, J=2.5, 5.8, 9.5 Hz, 1H), 5.39 (d, J=9.5 Hz, 1H), 4.89-4.46 (10H), 4.34 (t, J=6.3 Hz, 1H), 3.72-

3.46 (6H), 3.30 (t, J=9.1 Hz, 1H), 3.18 (bs, 1H), 2.97 (d, J=18.1 Hz, 1H), 2.94 (bs, 1H), 2.74 (dd, J=2.5, 15.7 Hz, 1H), 2.55-2.16 (7H), 1.95 (dt, J=8.0, 12.6 Hz, 1H), 1.76 (d, J=11.3 Hz, 1H); $^{13}$C δ 170.4, 144.2, 143.6, 138.1, 138.0, 137.8, 137.7, 137.6, 132.6, 129.8, 128.38, 128.37, 128.33, 128.3, 128.2, 128.0, 127.8, 127.7, 127.7, 127.65, 127.6, 125.9, 119.1, 116.3, 93.0, 86.8, 80.8, 78.7, 78.1, 77.4, 76.0, 75.7, 75.3, 75.0, 73.3, 68.7, 59.0, 50.0, 47.0, 44.0, 43.0, 39.9, 38.8, 35.9, 20.2; MS (EI) m/z 850 [M+H]$^+$; HRMS (ESI) calcd for $C_{53}H_{57}N_2O_8$ 849.4115, found 849.4099; the average purity of 11 was found to be ≧99% by analytical HPLC giving $t_R$=3.24 min (mobile phase A) and $t_R$=4.66 min (mobile phase B).

6-β-(2,3,4,6-Tetra-O-benzyl-β-D-glucopyranosyl)acetamido-7,8-dihydromorphine 12. The tetrabenzyl ether 12 (35.4 mg, 0.042 mmol) was dissolved in MeOH and 10% Pd—C (15 mg) was added. The mixture was stirred under an atmosphere of hydrogen for 24 h and then filtered through Celite. The Celite was washed with MeOH (10 mL) and $CH_2Cl_2$ (2 mL) and the filtrates were concentrated to provide 12 as a white solid (35 mg, 100%): $R_f$=0.66 (200:80:5:0.05 $CH_2Cl_2$/MeOH/$H_2O$/13% $NH_4OH$); mp=94.3° C.; $^1$H NMR ($CDCl_3$) δ 7.33-7.10 (20H), 6.92 (d, J=8.4 Hz, 1H), 6.69 (d, J=8.2 Hz, 1H), 6.56 (d, J=8.2 Hz, 1H), 4.88-4.29 (9H), 3.73-3.32 (8H), 3.05 (bs, 1H), 2.96 (d, J=18.4 Hz, 1H), 2.72 (dd, J=2.7, 15.7 Hz, 1H), 2.49-0.95 (15H); MS (EI) m/z 852 [M+H]$^+$.

Dihydromorphine-6-β-acetamidoglucose, 3. The tetrabenzyl derivative 11 (41 mg, 0.05 mmol) was dissolved in MeOH (2 mL). Concentrated HCl (13 μL) and then 10% Pd—C (40 mg) was added. The mixture was stirred under an atmosphere of hydrogen for 24 h. The solution was neutralized with Bio Rad RG 501-X8 mixed bed resin (1 g) and the mixture was filtered through Celite. The solids were washed with MeOH (30 mL) and the filtrate was concentrated. The residue was triturated with ethyl ether (3×2 mL) and dried under high vacuum, providing 3 as a white powder (12 mg, 52%): $R_f$=0.4 ($SiO_2$, 5:4:0.5:0.5 $CHCl_3$/MeOH/$H_2O$/concentrated $NH_4OH$); mp=266.4° C. (decomposed); $^1$H NMR δ 6.62 (s, 2H), 4.47 (d, J=7.8 Hz, 2H), 3.81-3.77 (m, 2H), 3.55-3.43 (m, 4H), 3.00 (t, J=9.3 Hz, 1H), 2.90 (d, J=5.4 Hz, 1H), 2.84 (s, 3H), 2.79-2.69 (m, 1H), 2.63 (dd, J=12.9, 14.4 Hz, 1H), 2.45 (d, J=11.7 Hz, 1H), 2.30-2.05 (m, 3H), 1.77-1.57 (m, 4H), 1.34-1.24 (2H), 1.00-0.92 (2H); $^{13}$C NMR (CD3OD) δ 173.9, 143.9, 142.6, 128.5, 122.3, 121.1, 119.4, 92.7, 81.6, 79.5, 77.9, 75.1, 72.0, 63.1, 52.7, 43.1, 41.9, 41.7, 40.3, 34.6, 29.2, 24.6, 21.7; MS (EI) m/z 491 [M+H]+; HRMS (ESI) calcd for $C_{25}H_{35}N_2O_8$ 491.2393, found 491.2375; the average purity of 3 was found to be ≧98% by analytical HPLC giving $t_R$=3.41 mM (mobile phase A) and $t_R$=3.74 mM (mobile phase B).

Receptor Binding. Binding to membranes from cells transfected with human μ, δ and κ opioid receptor was done in a 96-well format, as described previously (New compounds 10, 11, 12 and 3 were characterized by $^1$H NMR, $^{13}$C NMR and MS. The purity of test compounds 3 and 11 was determined by HPLC and was found to be >98%) Cells were removed from the plates by scraping with a rubber policeman, homogenized in Tris buffer using a Polytron homogenizer, then centrifuged once and washed by an additional centrifugation at 27,000×g for 15 min. The pellet was resuspended in 50 mM Tris, pH 7.5, and the suspension incubated with [$^3$H] DAMGO, [$^3$H]DPDPE, or [$^3$H]U69593, for binding to μ, δ or κ opioid receptors, respectively. The total incubation volume was 1.0 mL and samples were incubated for 60-120 min at 25° C. The amount of protein in the binding reaction varied from approximately 15 μg to 30 μg. The reaction was terminated by filtration using a Tomtec 96 harvester (Orange, Conn.) with glass fiber filters. Bound radioactivity was determined by counting with a Pharmacia Biotech beta-plate liquid scintillation counter (Piscataway, N.J.) and data expressed in counts per minute. $IC_{50}$ values were determined using at least six concentrations of test compound, and calculated using Graphpad/Prism (ISI, San Diego, Calif.). $K_i$ values were determined by the method of Cheng and Prusoff [Traynor, J. R. *Mol. Pharmacol.*, 47:848-854 (1995)].

[$^{35}$S]GTPγ-S binding. [$^{35}$S]GTPγ-S binding was done essentially as described by Traynor and Nahorski [Zaveri, N. et al., *Eur. J. Pharmacol.*, 428:29-36 2001]. Cells transfected with μ, δ and κ opiate receptors were scraped from tissue culture dishes into 20 mM Hepes, 1 mM EDTA, then centrifuged at 500×g for 10 min. Cells were resuspended in this buffer and homogenized using a Polytron homogenizer. The homogenate was centrifuged at 27,000×g for 15 min and the pellet resuspended in Buffer A, containing 20 mM Hepes, 10 mM $MgCl_2$, 100 mM NaCl, pH 7.4. The suspension was recentrifuged at 27,000×g and suspended once more in Buffer A. For the binding assay, membranes (8-15 μg protein) were incubated with [$^{35}$S]GTPγ-S (50 pM), GDP (10 μM), and the test compound, in a total volume of 1.0 mL, for 60 min at 25° C. Samples were filtered over glass fiber filters and counted as described for the binding assays. Statistical analysis was done using the program GraphPad Prism. In this assay, a compound's potency or affinity for the receptor was defined by its $EC_{50}$ for stimulating [$^{35}$S]GTPγS binding. Agonist efficacy was defined as the degree to which the compound maximally stimulated [$^{35}$S]GTP'γS binding relative to control. The $EC_{50}$ value represents the concentration of a compound that produced 50% maximal stimulation of [$^{35}$S]GTPγS binding.

Example 34

6-Naltrexamides for Alcohol and Nicotine Addiction

In the United States, alcoholism, nicotine addiction, and gambling addiction are serious psychiatric disorders with significant social and economic consequences. Epidemiological studies show that alcoholism will affect approximately 14% of the American population at some time in their lives [Regier, et al., *Arch. Gen. Psychiatry*, 50:85-94 (1993)]. An estimated 100,000 US citizens will die of alcoholism each year from direct and indirect causes [McKinnis and Foege, *JAMA*, 270:2207-2212 (1993)] and the economic costs including health and social costs are staggering at $166 billion per year (NIDA and NIAAA, 1998). Smoking is directly linked to lung cancer and stopping smoking is the major means of preventing lung cancer. Use of medications to treat withdrawal from alcoholism or nicotine and a role in rehabitation of alcoholic patients or smokers is limited. A number of medications have been tested to reduce or prevent the consumption of alcohol in addicted individuals. Some of these include disulfuram, lithium, selective serotonin reuptake inhibitors, and acamprosate. Disulfuram has been shown to have limited effectiveness [Garbutt et al., *JAMA*, 281:1318-1325 (1999)]. There are several ways that medications have been used to treat withdrawal from alcoholism. Several approaches to stopping smoking have been developed but the relapse rate is great. For alcoholism, deterrent drugs such as disulfuram make the ingestion of alcohol unpleasant. In contrast, medications attempt to decrease alcohol intake by reducing the reinforcing effects of alcohol or by reducing the urge or craving to ingest alcohol. Pharmacological agents appear to influence several neurotransmitter systems that underlie reinforcing or discrimination stimulus effects of ethanol or nicotine including endogenous opioids, catecholamines (especially dopamine, serotonin) and excitatory amino acids such as glutamate [Kranzler, *Am. J. Psychiat.,* 152:391-397 (1995)]. Despite the fact that a number of medications have been shown to be of value in the treatment of alcohol or nicotine dependence, pharmacotherapies have not had a large effect. There is some evidence that subgroups of alcoholics or smokers may respond well to certain medications, suggesting that treatment matching may increase the efficacy of medications. However, considerable basic information about strategic approaches, dosing and duration of treatment is just becoming available and much more information needs to be established. New approaches and new medications development are clearly needed to address these important issues.

In 1994, naltrexone was approved by the US FDA for treatment of alcoholism. Naltrexone is a pure opioid mu receptor antagonist with no agonist activity and no abuse potential. In a laboratory study of non-problem drinkers, naltrexone was found to decrease the reinforcing (i.e., stimulant) effects and increase the unpleasant (i.e., sedative) properties of initial alcohol consumption [Swift et al., *Am. J. Psychiat.,* 151:1463-1467 (1994)]. Studies using rodent and monkey have shown that the opioid antagonists naloxone and naltrexone reduce the voluntary consumption and stress-induced increase in alcohol consumption, suggesting that these agents may prevent the reinforcing effects of alcohol consumption [O'Brian et al., *Alcohol,* 13:35-39 (1996)]. Naltrexone may be most beneficial among alcoholics with higher levels of craving and poorer cognitive functioning [Jaffe et al., *J. Consult. Clin. Psychol.,* 64:1044-1053 (1996)]. However, in one study, 15% of patients undergoing treatment terminated treatment early due to adverse effects including intolerable nausea [Croop et al., *Arch. Gen. Psychiat.,* 54:1130-1135 (1997)]. Naltrexone is also associated with dose-dependent hepatotoxic side effects that complicate use and confound treatment of alcoholic patients with liver disease [Mason et al., *Arch. Gen. Psychiat.,* 56:719-724 (1999)]. Additional shortcomings include less than desirable duration of action and relatively low bioavailability [Wall et al., *Drug Metab. Dispos.,* 9:369-375 (1981)] and possibly, a relatively low affinity for delta and kappa receptors thought to be involved in diminishing the reinforcing effects of drinking alcohol. Beneficial effects of naltrexone diminish gradually over time. In addition, compliance with naltrexone treatment was variable and only among highly-compliant subjects was the active medication significantly better than placebo [Volpicelli et al., *Arch. Gen. Psychiat.,* 54:737-742 (1997)]. In summary, naltrexone appears to produce a modest effect on drinking behavior among alcoholics. In some cases, the effects of naltrexone have been quite robust but evidence of its efficacy has been less consistent. However, nalmefene, an opioid antagonist with superior pharmaceutical properties to naltrexone, may hold more promise as an alcohol treatment medication. Naltrexone has been reported to be useful for smoking cessation [O'Malley et al., U.S. Pat. No. 6,541,478].

Figure 15:
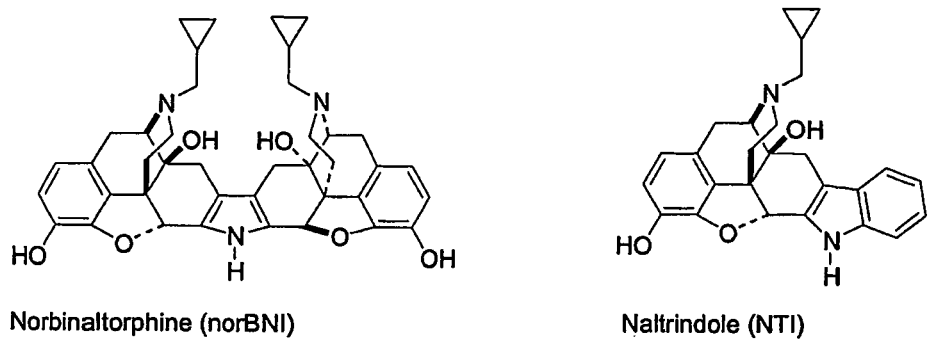
FIG. 15 depicts chemical structures of norBNI and naltrindole (NTI).

Opioid receptor antagonists apparently have direct effects on alcohol-seeking behavior. For example, direct perfusion of naloxone via microdialysis into the nucleus accumbens neurons inhibited alcohol-mediated dopamine release [Benjamin et al., *Brain Res.,* 621:137-140 (1993)]. The decrease in alcohol consumption by blockade of opioid receptors suggests direct effects of naloxone in this reinforcement system. Animal studies have provided evidence that μ-, δ- and κ-opioid receptors contribute to alcohol-induced reinforcement [Herz (1997); Ulm et al., *J. Clin. Psychiat.,* 56:5-14 (1995)]. Considerable work has been done related to the norbinaltorphimine (norBNI, FIG. 1) that is selective for the κ-opioid receptor [Portoghese et al., *J. Med. Chem.,* 31:1344-1347 (1987)]. The SAR of norBNI has been extensively investigated and is a bivalent ligand containing two naltrexone-derived pharmacophores. It is believed that only one of the norBNI pharmacophores is required for kappa antagonist activity and the basic group (at N-17') in the second pharmacophore of the receptor-bound ligand acts as an "address" to confer selectivity. In view of the apparent requirement of a rigid scaffold for orienting the molecule to the receptor, alternate structures have been developed including naltrindole (NTI, see FIG. 15). This indolomorphinan structures related to NTI is simpler than norBNI and has provided considerable evidence that K antagonists interact with a Glu297 address subsite [Stevens et al., *J. Med. Chem.,* 43:2759-2769 (2000)].

Figure 16:
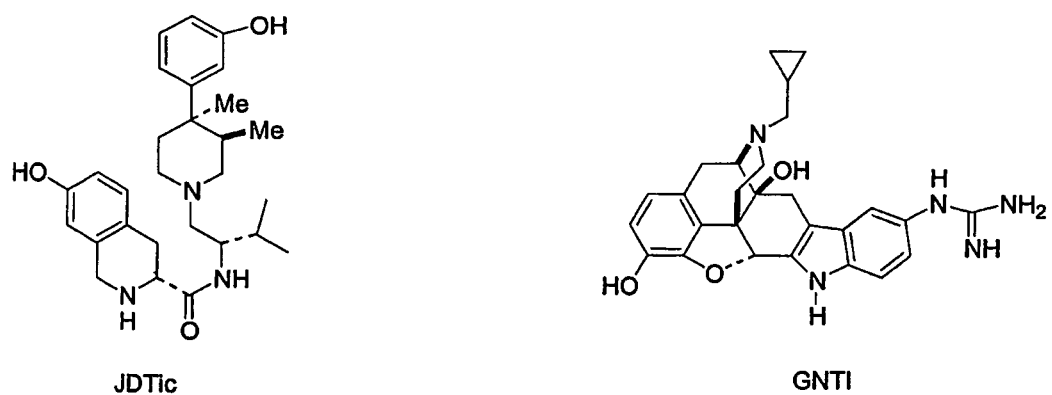
FIG. 16 depicts chemical structures of JDTic and guanidinenaltrindole (GNT1).

The requirement of a positively charged amino functionality in the address group necessary for is antagonist activity was further evidenced in a recent report that described a nonopiate-derived compound as a potent and selective opioid κ antagonist. The compound, JDTic (see FIG. 16) illustrates the importance of two basic amine groups: one each in both the address and message group. Further work showed the importance of a phenol group in κ selectivity that was not observed for the nor-BNI series [Thomas et al., *J. Med. Chem.,* 47:1070-1073 (2004)]. Based on chimeric kappa-mu opioid receptors, it is apparent that a negatively charged residue (i.e., Glu 297) is important in κ-selective binding and functional activity. Highly active κ-selective or non-κ-selective receptor selective antagonists would be useful for the treatment of addictions, particularly addictions to substances such as, e.g., nicotine or alcohol.

Figure 17:
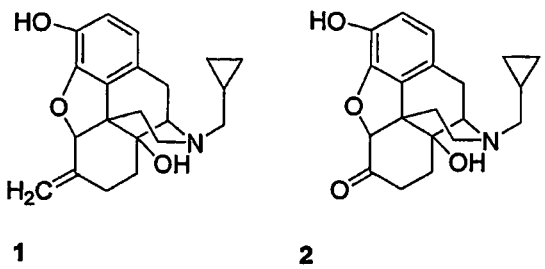
FIG. 17 depicts the chemical structures of nalmefene (1) and naltrexone (2).
Figure 18:
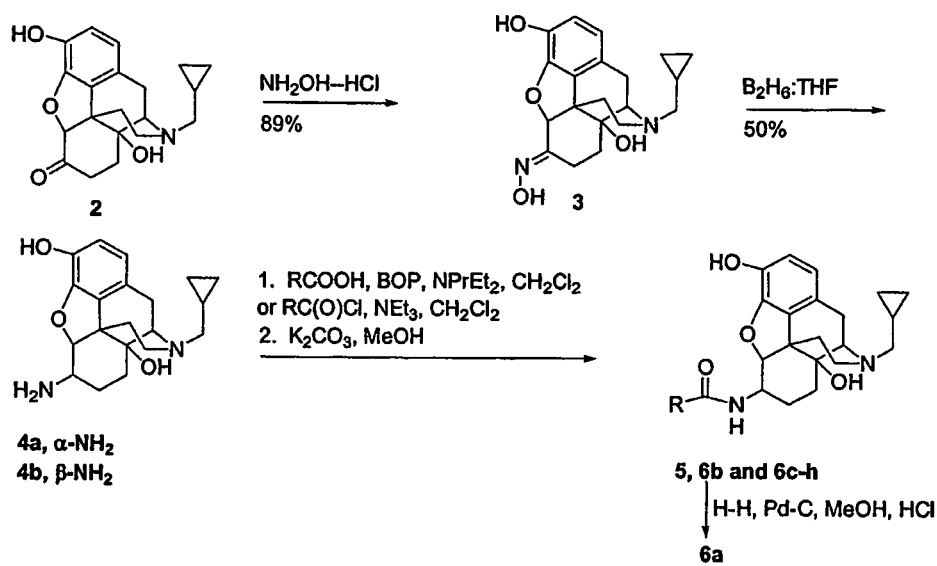
FIG. 18 depicts the general synthesis of opioid antagonists.

The chemical structures of nalmefene 1 and naltrexone 2 are shown in FIG. 17. These compounds are used for the treatment of opioid overdose, addiction and alcoholism. The medicinal chemistry objective of the present study was to develop metabolically stable analogues of these compounds by replacing the metabolically labile 6-methylene or 6-keto groups in 1 and 2, respectively, with an amide moiety. Various substitution patterns in the aromatic ring of the amide group were explored in order to increase mu and kappa opioid receptor selectivity and potency. A novel four step synthesis of either 6-α- or 6-β-naltrexamides was developed in order to meet this objective. The condensation of naltrexone 2 with hydroxylamine hydrochloride in the presence of NaOAc in refluxing aqueous ethanol provided the corresponding oxime 3 (see FIG. 18). Subsequent reduction of the oxime functional group in 3 to the corresponding amine 4 was accomplished by heating with $BH_3$/THF for 48 hours and subsequent aqueous workup giving the amines 4 as a 9:1 (β/α) mixture of diastereomers. The diastereomeric amines were separated by chromatography on silica gel. The amines 4 were coupled with carboxylic acids (RCOOH) in the presence of benzotriazol-1-yl-oxy-tris-(dimethylamino)phosphonium hexa-fluorophosphate (BOP) and diisopropylethylamine in $CH_2Cl_2$. Alternatively, the amides could be formed by the reaction of an acid chloride, triethylamine and 4 in $CH_2Cl_2$. In both cases, the product was treated with $K_2CO_3$ in methanol to deesterify the side-product resulting from esterification of the 3-position hydroxyl group. While the BOP coupling procedure resulted in less esterification at the 3-position than the acid chloride method, some esterification at the 3-position could not be avoided. Thus, it was found to be more convenient to run the reaction with an excess of the acid derivative to aid in the purification of the intermediate amide ester. These methods allowed us to conveniently prepare the amides 5 and 6a-h. The benzyl groups in compound 5 were removed by hydrogenolysis in the presence of Pd—C and HCl to give the glucose conjugate 6a.

TABLE 7

$K_i$, $K_e$ and $pA_2$ binding values of mu, delta and kappa opioid binding to CHO membranes.

| compound | $K_i$ (nM) mu | delta | kappa | Ke (mu) | Ke(other) | pA2 (mu) |
|---|---|---|---|---|---|---|
| morphine | 1.1 ± 0.1 | 140 ± 2 | 46.9 ± 14 | NA | | |
| naltrexone | 0.2 ± 0.03 | 11 ± 1.1 | 0.3 ± 0.03 | NA | | |
| 5 | 2.5 ± 0.6 | 140 ± 13.9 | 39 ± 6.3 | 0.16 + 0.02 | 10.35 + 2.01 (delta) | 2.5 ± 0.6 |
| 6a | 1.8 ± 0.5 | 91.3 ± 3.8 | 10.4 ± 2.8 | 0.37 + 0.03 | 13.39 + 1.51 (kappa) | 9.33 + 0.05 |
| 6b | NA | NA | NA | NA | NA | NA |
| 6c | 2.9 ± 0.1 | 6.2 ± 0.6 | 7.1 ± 0.8 | 0.41 + 0.02 | — | 9.34 + 0.02 |
| 6d | 0.6 ± 0.1 | 10.6 ± 1.2 | 0.6 ± 0.01 | 0.17 + .009 | — | 9.78 + 0.04 |
| 6e | 2.9 ± 0.1 | 6.2 ± 0.6 | 7.1 ± 0.8 | 0.41 + 0.02 | — | 9.34 + 0.02 |
| 6d | NA | NA | NA | NA | NA | NA |
| 6e | NA | NA | NA | NA | NA | NA |
| 6f | NA | NA | NA | NA | NA | NA |

NA, Not available.

The potency and selectivity observed for the corresponding agonists [MacDougall et al., *J. Med. Chem.*, 47:5809-5815 (2004); MacDougall et al., *Bioorganic Med. Chem.*, 12:5983-5990 (2004); MacDougall et al., *Bioorganic Med. Chem.*, 15:583-1586 (2005)] was generally retained in the antagonists. The amides 6d, 6e and 6c all possessed high affinity for the opioid receptors and partial or full or partial agonism at delta and kappa receptors (Table 8). All the compounds were strong antagonists at the mu receptor, based on GTPγS binding to cell membranes. Compound 6a had high affinity for mu and moderate affinity for delta and kappa receptors. 6a is a strong antagonist at mu and kappa and a partial agonist at delta receptors. In summary, the data shows potent leads are present with the functional consequences of antagonizing mu-alone or mu- and kappa-receptors.

The data show the feasibility that metabolically stable opioid antagonists can be synthesized and tested in vitro. Metabolically stable C-6 substituted opioid antagonists will retain favorable side effect profiles. In vitro results show that potent mu antagonists with either agonistic or antagonistic kappa properties can be synthesized. To examine whether kappa antagonism or agonism is more efficacious in decreasing alcohol consumption, leads were studied in an animal model of alcoholism and nicotine addiction. Highly active κ-selective or non-κ-selective receptor selective antagonists would be useful for the treatment of addictions, particularly addictions to substances such as, e.g., nicotine or alcohol.

In the following examples (Examples 35-43), all reactions were run under a positive pressure of nitrogen with magnetic stirring at ambient temperature using oven-dried glassware

TABLE 8

Stimulation of $^{35}$S-GTP-gamma-S binding by HBRI Compounds.

| Entry | mu $EC_{50}$ | % stimulation | delta $EC_{50}$ | % stimulation | kappa $EC_{50}$ | % stimulation |
|---|---|---|---|---|---|---|
| morphine | 15.6 ± 0.5 | 93 ± 3 | ND | ND | ND | ND |
| M6G | 72.3 ± 26.7 | 45.0 ± 5.0 | 190.4 ± 22.9 | 80.0 ± 1.0 | >10,000 | — |
| 5 | 9.7 ± 0.5 | 21.4 ± 0.5 | 106.8 | 20.5 | 10.8 | 45.5 |
| 6a | 42.3 ± 5.4 | 15.8 ± 1.6 | 90.9 | 43.1 | 11.2 | 11.01 |
| 6b | NA | NA | NA | NA | NA | NA |
| 6c | 4.6 ± 0.9 | 19.3 ± 0.1 | 7.3 | 100 | 1.1 | 126.5 |
| 6d | 1.2 ± 0.6 | 20.6 ± 1.5 | 11.1 | 98.7 | 1.7 | 109.1 |
| 6e | 5.2 ± 1.6 | 16.1 ± 1.9 | 24.5 | 88.5 | 100.1 | 53.6.1 |

To investigate metabolic stability, HPLC and LCMS assays were developed to study the metabolic and chemical stability and found that generally, the compounds in these series were remarkably stable to metabolism and to degradation. The analogs were designed to be stable in hepatic preparations due to blockade of the C-6 position and this is what was observed. Preliminary results showed that 6d and 6a hold promise as potent opioid antagonists (Tables 7 and 8). Because the tetra-O-benzyl-β-D-glucopyranosyl protected compound 5 had been synthesized, its in vitro binding and functional properties were investigated. Compound 5 had high affinity for mu and moderate affinity for kappa and low affinity for delta receptors. The studies point to the glucose analogs themselves as promising development candidates.

unless otherwise indicated. Air- and moisture-sensitive liquids were transferred via syringe through rubber septa. Silica gel (230-400 mesh) was used for column chromatography. DMF was dried by filtration through a column of neutral alumina and stored over activated 4 Å molecular sieves under nitrogen prior to use. All other solvents and reagents were used as received. $^1$H NMR spectra were recorded at 300 MHz using a Varian NMR. Chemical shifts were reported in ppm (δ) relative to CDCl$_3$ at 7.26 ppm. $^1$H NMR spectra were recorded in CDCl$_3$ unless stated otherwise. Melting points were reported uncorrected. High-resolution mass spectra was done on a VG 7070 spectrometer with an Opus V3.1 and DEC 3000 Alpha Station data system at the University of California Riverside. Where combustion analyses was not specified, analytical purities were determined by straight phase HPLC using a Hitachi L74 liquid chromatograph with a L-7400 uv detector, a D7500 integrator and a Hamilton PRP-I stainless steel column (250 mm×4.6 mm i.d.).

Naltrexone oxime, 3 was prepared according to the following method. Naltrexone (6.2 g, 1.46 mmol), $NH_2OH$—HCl (1.5 g) and NaOAc (2.9 g) were dissolved in absolute EtOH (80 mL) and water (5 mL). The mixture was heated at reflux for 2.5 h and then concentrated. Water (20 mL) was added and the mixture was made basic with $K_2CO_3$ and extracted with $CHCl_3$. The $CHCl_3$ extract was washed with brine, dried over $Na_2SO_4$, filtered and concentrated to a white solid (5.83 g, 90%): $R_f$=0.65 (5:1:0.2 EtOAc/MeOH/$NH_4OH$); MS (EI) m/z=357 [MH]$^+$.

6-β-Naltrexamine and 6-α-naltrexamine, 4b, 4a were prepared according to the following method. Naltrexone oxime (5.83 g, 16.3 mmol) was dissolved in THF (40 mL) and transferred by cannula to a 10° C. solution of $BH_3$:THF (300 mL, 300 mmol, 1 M solution in THF) over 10 min. A white precipitate formed and then slowly dissolved as the reaction was heated at reflux for 2 d. The solution was cooled to rt and water (10 mL) and 1 N KOH (200 mL) were added slowly with caution. The solution was heated at reflux for 2 h. The pH was then reduced to 2.5 with 10% HCl (225 mL). The solution was heated at reflux for 2 h, concentrated to remove the THF and then made basic (pH 8-9) with $K_2CO_3$. The mixture was extracted with $CHCl_3$ (4×150 mL) and the extract was dried over $Na_2SO_4$, filtered and concentrated. The resulting oil was purified by chromatography on $SiO_2$ (26×60 cm, elution with $CH_3CN$/MeOH/$NH_4OH$, 25:5:1) providing 4b (2.14 g, 38%) as a white-yellow solid: $R_f$=0.20; $^1H$ NMR (300 MHz, $CDCl_3$ with 2 drops of CD3OD) δ 6.61 (d, J=8.1 Hz, 1H), 6.49 (d, J=8.1 Hz, 1H), 4.17 (d, J=7.5 Hz, 1H), 3.39-0.45 (20H); MS m/z=343 [MH]$^+$. An additional 0.64 g (12%) of material consisting of a mixture of the α- and β-diastereomers was isolated. Preparative chromatography ($SiO_2$, $CH_3CN$/MeOH/$NH_4OH$, 25:5:1) of the tailing fractions of this material gave an analytical sample of 4a: $R_f$=0.16; $^1H$ NMR δ 6.65 (d, J=8.1 Hz, 1H), 6.46 (d, 8.1 Hz, 1H), 4.50 (d, J=3.0 Hz, 1H), 3.34 (dt, J=3.9, 12.6 Hz, 1H), 3.04 (t, J=6.6 Hz, 1H), 2.95 (s, 1H), 2.63-0.29 (17H); MS m/z 343 [MH]$^+$.

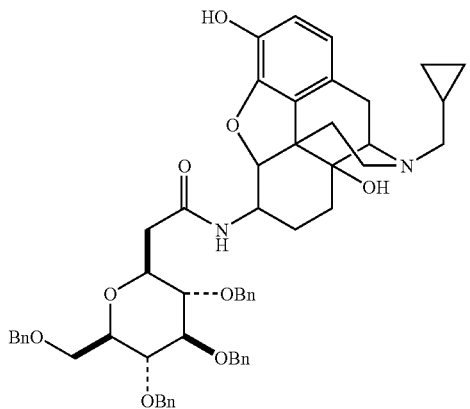

Example 35

6-acetamido-2,3,4,6-tetra-O-benzyl-D-glucopyranosyl-14-Hydroxy-17-(cyclopropylmethyl)nordesmorphine, 5

6-Naltrexamine (100 mg, 0.292 mmol), carboxylic acid (RCOOH, Scheme 1) (187 mg, 0.321 mmol) and BOP (142 mg, 0.321 mmol) were dissolved in $CH_2Cl_2$ (3 mL) and $NPr_2Et$ (0.16 mL, 0.92 mmol) was added. The colorless solution was stirred at rt for 90 min and concentrated. The residue was filtered through $SiO_2$ (20:1 EtOAc/MeOH) providing a white solid. This material (240 mg) was dissolved in MeOH (10 mL) and $K_2CO_3$ (36 mg, 0.26 mmol) was added. The mixture was stirred for 115 min and saturated $NH_4Cl$ (10 drops) was added. The mixture was concentrated and adsorbed onto $SiO_2$ and purified by $SiO_2$ chromatography (20:1 $CHCl_3$/MeOH) providing 7 as a white solid (200 mg, 75% from 6-naltrexaminenaltrexamine, 2-steps): $R_f$=0.11 (20:1 $CHCl_3$/MeOH); MS (EI) m/z=907 [M]$^+$; $^1H$ NMR ($CDCl_3$, key resonances) δ 7.31-7.06 (m); 6.76 (d), 6.71 (d); 6.55 (d); 6.54 (d) 4.94-4.38 (m); 3.86-3.79 (m); $^{13}C$ NMR ($CDCl_3$) δ 170.4, 143.6, 138.1, 137.6, 128.4, 128.4, 128.3, 128.1, 127.9127.8, 127.78, 127.7, 127.69, 127.64, 118.9, 93.8, 86.8, 81.0, 78.4, 75.8, 75.7, 75.2, 75.0, 73.2, 70.1, 59.2, 50.9, 30.2, 4.1, 3.9.

Example 36

14-Hydroxy-17-(cyclopropylmethyl)nordesmorphine-6-acetamidoglucose, 6a

Anhydrous MeOH (8 mL) was added to benzylated derivative 5 (180 mg, 0.198 mmol) and 10% activated Pd—C (180 mg). Concentrated HCl (0.015 mL) was added by syringe. The flask was purged with nitrogen and then stirred under a balloon of hydrogen for 21 h, filtered through Celite (eluting with MeOH) and concentrated. The resulting white solid was triturated with ethyl ether (anhyd, 3×2 mL) to provide 6a as a white solid (92 mg, 85%): $R_f$=(5:4:0.5:0.5 $CHCl_3$/MeOH/$H_2O$/$NH_4OH$); $^1H$ NMR (CD3OD, key resonances) δ 6.72 (s), 4.67 (d); 4.60-4.52 (m); 3.99 (d); 3.90-3.48 (m); MS m/z=547 [M+H]$^+$.

Example 37

General Procedure for the Amidation of 6-naltrexamines with an Acid Chloride. 6-(Pyridine-3'-yl)carboxamido-14-hydroxy-17-(cyclopropylmethyl)nordesmorphine, 6b 6-Aminonaltrexamine (53 mg, 0.155 mmol) was dissolved in $CH_2Cl_2$ (2 mL) and nicotinyl chloride-HCl (40 mg, 0.226 mmol) and $NEt_3$ (0.085 mL, 0.465 mmol) were added. The solution was stirred for 1.5 h and concentrated. The residue was purified by chromatography on $SiO_2$ (10:1 $CH_2Cl_2$/MeOH) providing the amide ester as a yellow-white solid (63 mg, 74%): $R_f$=0.11 (10:1 $CH_2Cl_2$/MeOH); MS m/z=552. The amide ester (53 mg, 0.096 mmol) was dissolved in MeOH (2 mL) and $K_2CO_3$ (46 mg, 0.33 mmol) was added. The mixture was stirred at rt for 1 h and $NH_4Cl$ (sat. aq. 10 drops) and $SiO_2$ (2 g) were added. The mixture was concentrated and purified by $SiO_2$ chromatography (10:1 $CHCl_3$/MeOH) providing the title compound as an off-white solid (27 mg, 63%): $R_f$=0.31 (10:1 $CHCl_3$/MeOH); MS m/z=447.

Example 38

General Procedure for the Amidation of 6-naltrexamines with the BOP Reagent and a Carboxylic Acid. 6-(3'-dimethylamino)benzamido-14-hydroxy-17-(cyclopropylmethyl)nordesmorphine, 6c $CH_2Cl_2$ (1.5 mL) was added to naltrexamine (50 mg, 0.146 mmol), 3-dimethylaminobenzoic acid (24 mg, 0.14 mmol), BOP reagent (64 mg, 0.14 mmol) and Pr$_2$EtN (0.081 mL, 0.47 mmol). The yellow solution was stirred at rt for 80 min and concentrated. The residue was chromatographed on SiO$_2$ (10:1 EtOAc/MeOH) providing a white solid (70 mg). This material was dissolved in MeOH (4 mL) and K$_2$CO$_3$ (30 mg, 0.22 mmol) was added. After 90 min the mixture was concentrated. The residue was purified by chromatography on SiO$_2$ (10:1 CHCl$_3$/MeOH) to provide the title compound as a white solid (17.4 mg, 24% from naltrexamine): R$_f$=0.16 (10:1 CHCl$_3$/MeOH); MS m/z=490 [MH]$^+$.

Example 39

6-(3'-Methoxy)benzamido-14-hydroxy-17-(cyclopropylmethyl)nordesmorphine, 6d

Reference JMM-VIII-42. Employing the general procedure described for compound 6b, 6-naltrexamine (90 mg, 0.263 mmol), 3-anisoylchloride (0.09 mL, 0.69 mmol), NEt$_3$ (0.11 mL, 0.83 mmol) and CH$_2$Cl$_2$ (2 mL) gave the intermediate amide ester as a white foam (96 mg); MS m/z=611. Hydrolysis of this material with K$_2$CO$_3$ (43 mg, 0.31 mmol) in MeOH (3 mL), followed by SiO$_2$ chromatography (10:1 CH$_2$Cl$_2$/MeOH) gave 6d as a white solid: 57 mg (78%); MS m/z=477.

Example 40

6-(Thiophen-2'-yl)acetamidomido-14-hydroxy-17-(cyclopropylmethyl) nordesmorphine, 6e Employing the general procedure described for compound 6b, 6-naltrexamine (19 mg, 0.055 mmol), 2-thiophene acetylchloride (0.014 mL, 0.11 mmol), NEt$_3$ (0.019 mL, 0.14 mmol) and CH$_2$Cl$_2$ (2 mL) gave the intermediate amide ester as a white foam (15 mg, 46%); R$_f$=0.12 (30:1 CH$_2$Cl$_2$/MeOH); MS m/z=591 [MH$^+$]. Hydrolysis of this material (13 mg, 0.022 mmol) with K$_2$CO$_3$ (2.5 mg, 0.0.018 mmol) in MeOH (2 mL), followed by SiO$_2$:chromatography (15:1 CH$_2$Cl$_2$/MeOH) gave 6e as a white solid (10 mg, 100%): R$_f$=0.17 (15:1 CH$_2$Cl$_2$/MeOH); MS m/z=467.

Example 41

6-(3',5'-Dimethoxy)benzamido-14-hydroxy-17-(cyclopropylmethyl)nordesmorphine, 6f According to the general procedure described for compound 6c, 4 (90 mg, 0.263 mmol), 3,5-dimethoxybenzoic acid (72 mg, 0.395 mmol), BOP (174 mg, 0.394 mmol), NPr$_2$Et (0.15 mL, 0.84 mmol) and CH$_2$Cl$_2$ (3 mL) provided the intermediate amide ester as a white-orange solid (186 mg). MS analysis of this material indicated that it consisted of a mixture of the amide ester (m/z=671) and the amide (m/z=507). Deesterification of this material with K$_2$CO$_3$ (150 mg, 1.1 mmol) in MeOH (4 mL) and SiO$_2$ chromatography (20:1 CH$_2$Cl$_2$/MeOH) provided 6f as a white solid: MS m/z=507.

Example 42

6-(4'-Chloro)benzamido-14-hydroxy-17-(cyclopropylmethyl)nordesmorphine, 6g

Reference VIII-58. According to the general procedure described for compound 6c, 4 (90 mg, 0.26 mmol), 4-chlorobenzoic acid (62 mg, 0.39 mmol), BOP (174 mg, 0.394 mmol) and NEtPr$_2$ (0.15 mL, 0.842 mmol), followed by SiO$_2$ chromatography (20:1 EtOAc/MeOH) afforded the intermediate amide ester as a white solid: R$_f$=0.5 (20:1 EtOAc/MeOH); MS m/z=620. Deesterification of this material with K$_2$CO$_3$ (72 mg, 0.53 mmol) in MeOH (4 mL), followed by SiO$_2$ chromatography (20:1 CH$_2$Cl$_2$/MeOH) provided 6g as a white solid (76 mg, 60%): R$_f$=0.41 (20:1 CH$_2$Cl$_2$/MeOH); MS m/z=480.

Example 43

6-(3'-Hydroxy)benzamido-14-hydroxy-17-(cyclopropylmethyl)nordesmorphine, 6h

Reference JMM-VIII-59, VIII-64. According to the general procedure described for compound 8b, 4 (90 mg, 0.26 mmol), 3-acetoxybenzoic acid (71 mg, 0.39 mmol), NEtPr$_2$ (0.15 mL, 0.84 mmol), BOP (174 mg, 0.39 mmol) and CH$_2$Cl$_2$ (2 mL) and SiO$_2$:chromatography (20:1 EtOAc/MeOH) gave the intermediate amide ester as a white foam (180 mg): R$_f$=0.28 (10:1 CHCl$_3$/MeOH); MS m/z=667. Deesterification of this material with K$_2$CO$_3$ (72 mg, 0.53 mmol) in MeOH (2 mL) and SiO$_2$ chromatography (20:1 CH$_2$Cl$_2$/MeOH) gave 8 h as a white solid (76 mg, 60%), R$_f$=0.41 (20:1 CH$_2$Cl$_2$/MeOH); MS m/z=480.

Example 44

In Vitro Metabolic Stability

The metabolic stability of a compound in an in vitro study can provide significant information about the potential for metabolic stability in an in vivo experiment. Because a prominent route of metabolism in the opioid class of compound is for metabolism at the C-6 position, metabolic stability was designed into the compounds to increase half life, to increase bioavailability, and to improve the pharmacokinetic profile and the side effect profile of the synthetic compounds. By overcoming ADMET liabilities in the early stage of drug design and development, more drug-like compounds were produced.

In vitro metabolic stability studies of selected compounds were studied in the presence of pooled human liver S9, rat liver microsomes and mouse liver microsomes. The studies were done to mimic the human metabolic situation and the animal liver metabolism studies were done as a model study of in vivo animal studies (see below). The assay buffer contained 3.2 mg/mL human liver pooled S9 or 1.2 mg/mL rat or mouse liver microsomes, 0.1 M potassium phosphate buffer (pH 7.4), 0.1 mM compounds, 0.5 mM NADP+, 0.5 mM glucose-6-phosphate, 5 IU/mL glucose-6-phosphate dehydrogenase, 1 mg/mL DETAPAC, 7 mM MgCl$_2$ for a final incubation volume of 0.25 mL. After 0, 10, 25, 45 or 60 min the reactions were stopped by the addition of 1 mL CH$_2$Cl$_2$/PA (3:1 v:v) and mixed thoroughly. After centrifuged, the organic phase was evaporated to dryness with a stream of nitrogen, taken up into 200 µL methanol, vortexed, and centrifuged. HPLC was used to analyze the organic extract with an Axxi-Chrom Silica 5 micron column purchased from Richard Scientific (Novato, Calif.) on a Hitachi HPLC. The mobile phase consisted of: 55/45/0.018 (MeOH/IPA/HClO$_4$) and a flow rate of 1.5 mL/min with UV detection at 254 nm. The retention time of naltrexone, nalmefene and compound 6d was 2.7 min, 2.1 min, and 2.6 min, respectively.

As shown in Table 9, naltrexone and nalmefene possessed considerable metabolic instability in the presence of the liver preparations examined. In contrast, in the presence of human liver S-9 and mouse liver microsomes, compound 6d was not detectably metabolized. In the presence of rat liver microsomes, a minor amount of metabolism was observed, but it was 6- or 22-fold more stable than naltrexone or nalmefene, respectively. In summary, considerable metabolic stability was observed for compound 6d and the prediction is that the bioavailability of compound 6d and congeners will be considerable.

TABLE 9

Metabolic stability of C-6-substituted Opiate Antagonists.

| Compound | Human liver S-9[a] | Half life in various liver preparations (mins) | |
|---|---|---|---|
| | | Rat liver microsomes | Mouse liver microsomes |
| Naltrexone | 47 | 93.5 | 430 |
| Nalmefene | 217.5 | 25 | 34 |
| Compound 6d | ND | >545 | ND |

[a]Human liver S-9 is the post-mitochondria supernatant from the 9000 x g centrifugation.
[b]ND, No Detectable change Example 45

In Vivo Activity

Figure 19:
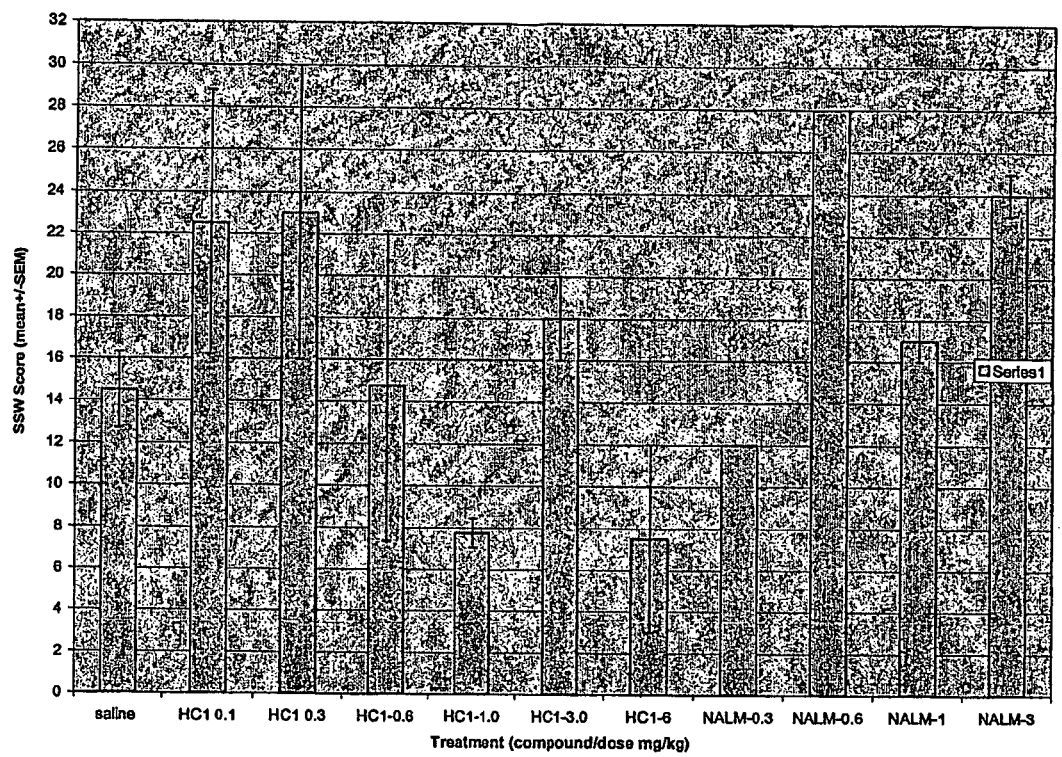
FIG. 19 depicts the effect of compound 6d of Example 38 on somatic signs of withdrawal.
Figure 20:
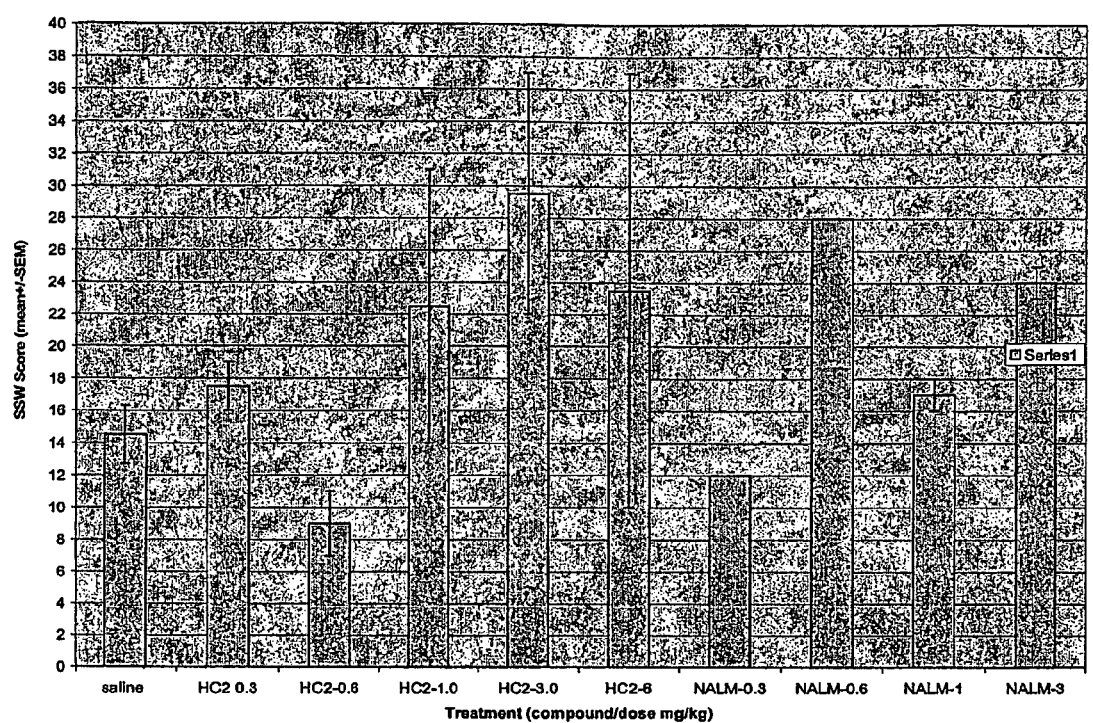
FIG. 20 depicts the effect of compound 6a of Example 35 on somatic signs of withdrawal.

The observation of an acute dependence state as defined by antagonist-precipitation of somatic withdrawal signs following acute pretreatment with opiates has been reported in humans, monkeys, dogs, hamsters, mice and rats. In both humans and rats, opiates precipitate signs of opiate withdrawal after a single exposure to morphine. The paradigm in rats resembled the condition in humans. Thus, naloxone (0.03-3.0 mg/kg) precipitated somatic signs of withdrawal following a single treatment with morphine (5.0 mg/kg) 4 hr prior to injection of naloxone [Schulteis et al., *Psychopharmacology*, 129:56-65 (1997)]. The overall index of withdrawal intensity used the weighted scale of Gellert and Holtzman [*J. Pharmacol. Exper. Ther.*, 205:536-546 (1978)]. The scale consists of graded signs of weight loss, number of escape attempts, rearings, number of wet dog shakes, instances of abdominal constrictions, and checked signs (present or absent) including diarrhea, facial fasciculations/teeth chattering, swallowing-movements, profuse salivation, chromodacryorrhea, ptosis, abnormal posture, penile grooming/erection/ejaculation and irritability upon handling. For our studies, the Global somatic sign (SS) rating included all the above individual signs based on the weighted scale of Gellert and Holtzman (1978). Four hr after a single dose of morphine (5.0 mg/kg), a single dose of compound 6a or 6d was administered to groups of rats. One min after s.c injection, somatic signs of withdrawal were observed for 10 mins. The results are summarized in FIGS. 19 and 20.

In summary, compounds 6a and 6d administered by subcutaneous route of administration precipitated somatic signs of withdrawal in adult male rats 4 hr after administration of 5.0 mg/kg of morphine. Compound 6d caused a dose-dependent increase in somatic signs of withdrawal that peaked at 0.3 mg/kg. An approximate $EC_{50}$ value of less than 0.1 mg/kg was observed. At higher doses, the effect was decreased. For compound 6a, an approximate $EC_{50}$ of approximately 1 mg/kg was observed for precipitation of somatic signs of withdrawal. For comparison, nalmefene caused a dose-dependent (albeit noisy) increase in somatic signs of withdrawal that gave an approximate $EC_{50}$ value of 0.6-1 mg/kg. For a literature standard, the minimum effective dose of naloxone to precipitate somatic signs of withdrawal was calculated to be 0.1-0.3 mg/kg [Schulteis et al., *Psychopharmacology*, 129:

56-65 (1997)]. In conclusion, the data supports the in vivo efficacy of compounds 6a, 6d and congeners as potent antagonists of the opiate receptor. The compounds get into the central nervous system relatively rapidly (within 10 minutes) and exert a potent effect on the opiate receptor. Because this receptor system is prominent in controlling addiction susceptibility to alcohol and nicotine, opiate antagonists such as 6 should be effective at decreasing nicotine and alcohol addiction.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:
1. A compound having the formula:

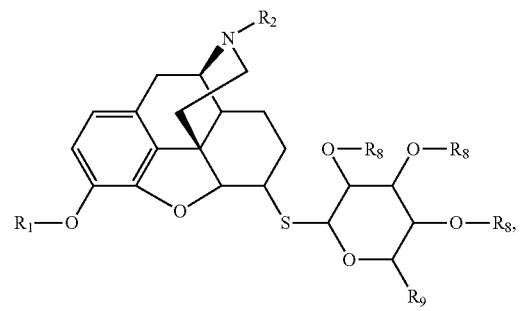

or a pharmaceutically acceptable salt thereof and all stereochemical arrangements of substituents, including racemic or stereochemically pure compounds, wherein:
$R_1$ is selected from the group consisting of H, $(C_1-C_5)$alkylC(O)—, $(C_7-C_{10})$aralyl, and $(C_1-C_5)$alkyl;
$R_2$ is selected from the group consisting of $(C_1-C_5)$alkyl, $C_3-C_6$(cycloalkyl)alkyl, $C_5-C_7$(cycloalkenyl)alkyl, $(C_6-C_{12})$aryl$(C_7-C_{12})$aralkyl, trans$(C_4-C_5)$alkenyl, allyl, and furan-2-ylalkyl;
each $R_8$ is independently selected from the group consisting of H, $(C_1-C_5)$alkylC(O), $(C_7-C_{10})$aralylC(O), $(C_7-C_{10})$aralyl, and $(C_1-C_5)$alkyl; and
$R_9$ is selected from the group consisting of $CH_2OH$, $CH_2O_2C(C_1-C_5)$alkyl, $CH_2O(C_7-C_{10})$aralyl, $CO_2H$, $CO_2(C_1-C_5)$alkyl, and $CO_2(C_7-C_{10})$aralyl.
2. The compound of claim 1 having the formula:

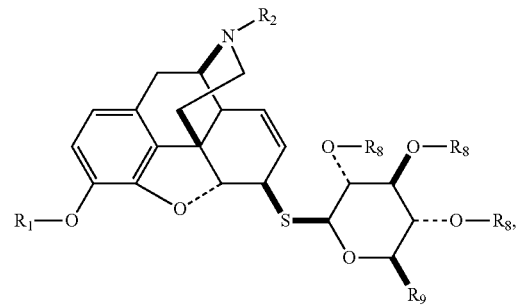

wherein
$R_1$ is selected from the group consisting of H, $(C_1-C_5)$alkylC(O)—, $(C_7-C_{10})$aralyl, and $(C_1-C_5)$alkyl;

R$_2$ is selected from the group consisting of (C$_1$-C$_5$)alkyl, C$_3$-C$_6$(cycloalkyl)alkyl, C$_5$-C$_7$(cycloalkenyl)alkyl, (C$_6$-C$_{12}$)aryl (C$_{7-12}$)aralkyl, trans(C$_4$-C$_5$)alkenyl, allyl, and furan-2-ylalkyl;

each R$_8$ is independently selected from the group consisting of H, (C$_1$-C$_5$)alkylC(O), (C$_7$-C$_{10}$)aralylC(O), (C$_7$-C$_{10}$ aralyl, and (C$_1$-C$_5$)alkyl; and R$_9$ is selected from the group consisting of CH$_2$OH, CH$_2$O$_2$C(C$_1$-C$_5$)alkyl, CH$_2$O(C$_7$-C$_{10}$)aralyl, CO$_2$H, CO$_2$(C$_1$-C$_5$)alkyl, and CO$_2$(C$_7$-C$_{10}$)aralkyl.

3. The compound of claim 1 having the formula:

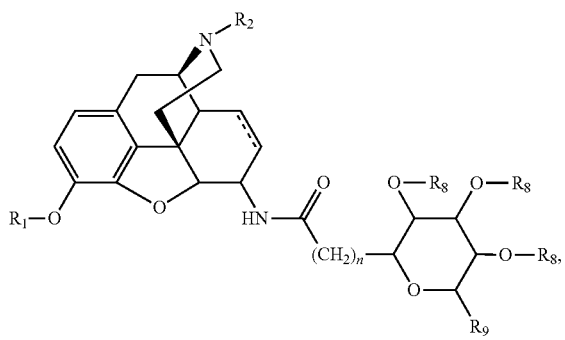

or a pharmaceutically acceptable salt thereof and all stereochemical arrangements of substituents, Including racemic or stereochemically pure compounds wherein R$_1$ is selected from the group consisting of H, (C$_1$-C$_5$)alkylC(O)—, (C$_7$-C$_{10}$)aralyl and (C$_1$-C$_5$)alkyl;

R$_2$ is selected from the group consisting of (C$_1$-C$_5$)alkyl, C$_3$-C$_6$(cycloalkyl)alkyl, C$_5$-C$_7$(cycloalkenyl)alkyl, (C$_6$-C$_{12}$)aryl (C$_7$-C$_{12}$)aralkyl, trans(C$_1$-C$_5$)alkenyl, allyl and furan-2-ylalkyl;

each R$_8$ is independently selected from the group consisting of H, (C$_1$-C$_5$)alkylC(O), (C$_1$-C$_{10}$)aralylC(O), (C$_7$-C$_{10}$)aralyl, (C$_1$-C$_5$)alkyl, R$_9$ is selected from the group consisting of CH$_2$OH, CH$_2$O$_2$C(C$_1$-C$_5$)alkyl, CH$_2$O(C$_7$-C$_{10}$)aralyl, CO$_2$H, CO$_2$(C$_1$-C$_5$)alkyl and CO$_2$(C$_7$-C$_{10}$)aralkyl;

and the subscript n is an integer of from 0 to 5.

4. The compound of claim 3 having the formula:

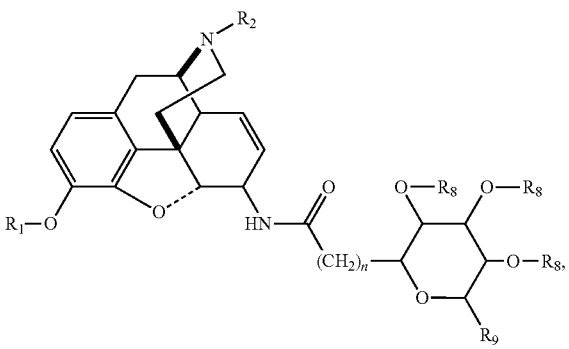

wherein

R$_1$ is selected from the group consisting of H, (C$_1$-C$_5$)alkylC(O)—, (C$_7$-C$_{10}$)aralyl and (C$_1$-C$_5$)alkyl;

R$_2$ is selected from the group consisting of (C$_1$-C$_5$)alkyl, C$_3$-C$_2$6(cycloalkyl)alkyl, C$_5$-C$_7$(cycloalkenyl)alkyl, (C$_6$-C$_{12}$)aryl (C$_7$-C$_{12}$)aralkyl, trans(C$_4$-C$_5$)alkenyl, alkyl and furan-2-ylalkyl;

each R$_8$ is independently selected from the group consisting of H, (C$_1$-C$_5$)alkyl C(O), (C$_7$-C$_{10}$)aralylC(O), (C$_7$-C$_{10}$)aralyl, (C$_1$-C$_5$) alkyl, R$_9$ is selected from the group consisting of CH$_2$OH, CH$_2$O$_2$C(C$_1$-C$_5$)alkyl, CH$_2$O(C$_7$-C$_{10}$)aralyl, CO$_2$H, CO$_2$(C$_1$-C$_5$)alkyl and CO$_2$(C$_7$-C$_{10}$)aralkyl; and the subscript n is an integer of from 0 to 5.

5. The compound of claim 1 or claim 3, wherein R$_2$ is selected from the group consisting of cyclopropylmethyl, cyclobutylmethyl, and allyl.

6. The compound of claim 1 or claim 3 selected from the group consisting of:

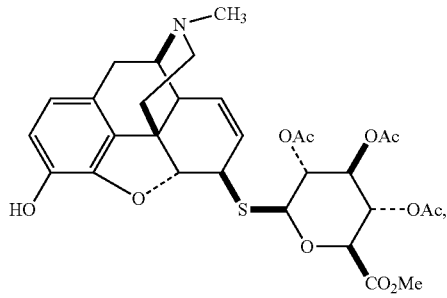

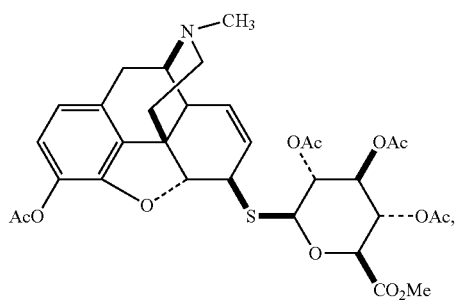

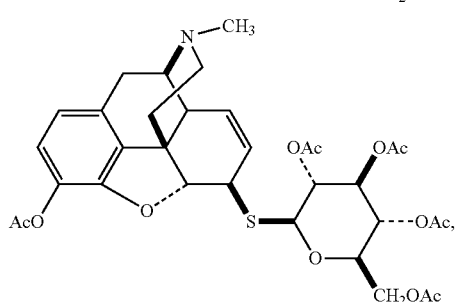

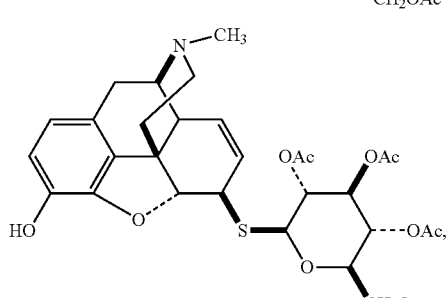

-continued
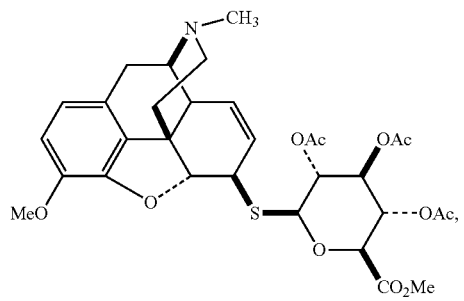
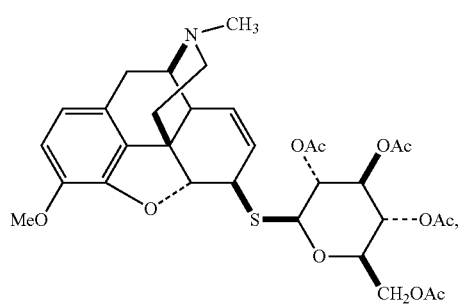
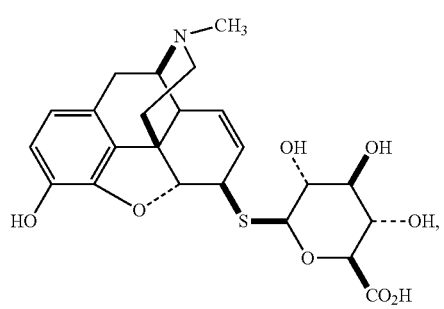
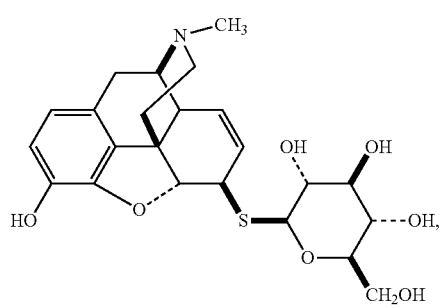
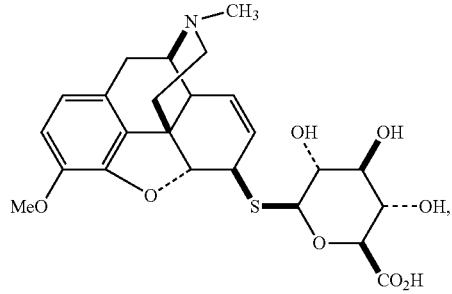
-continued
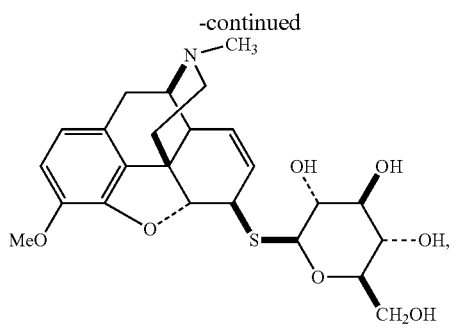
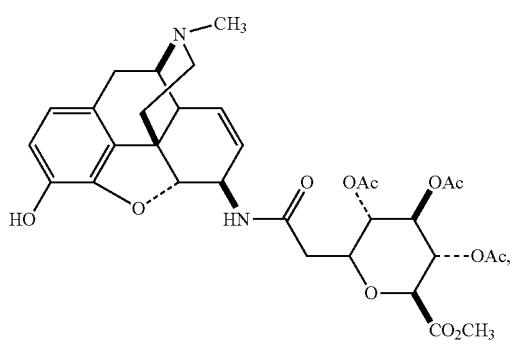
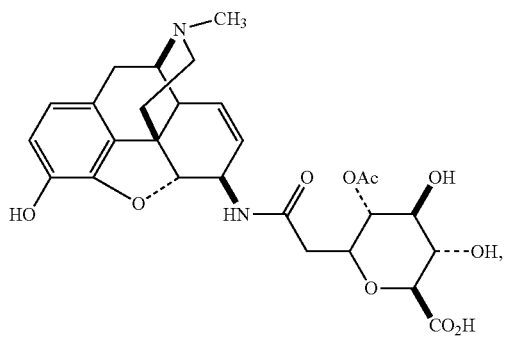
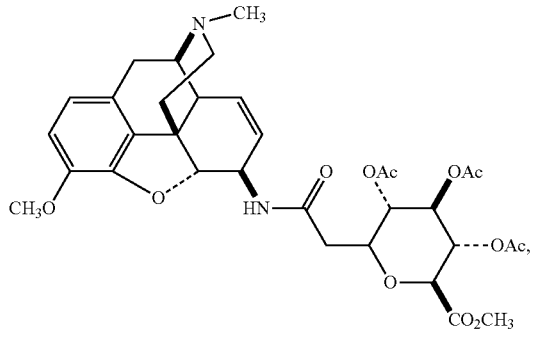
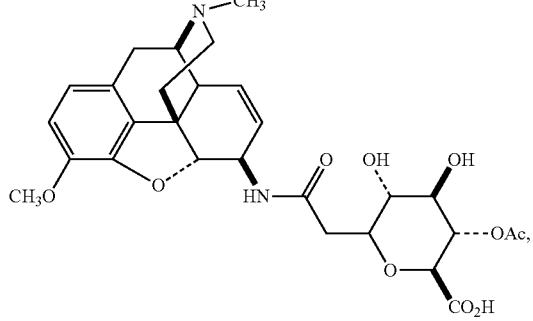

-continued

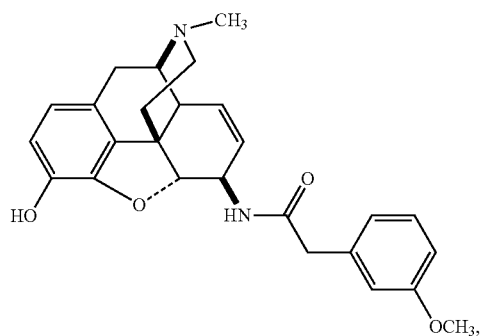

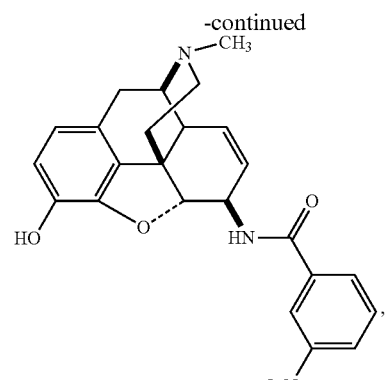

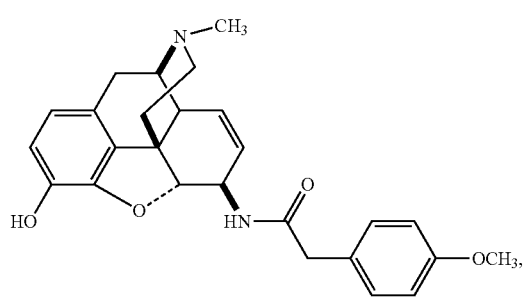

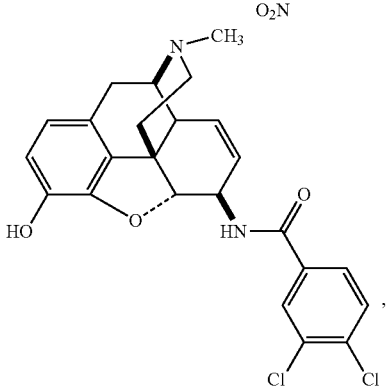

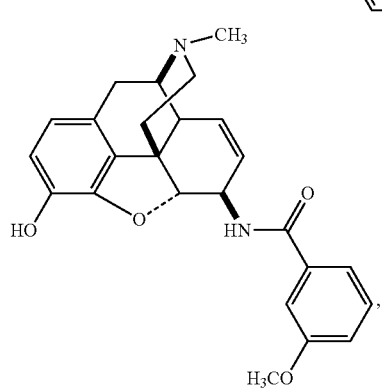

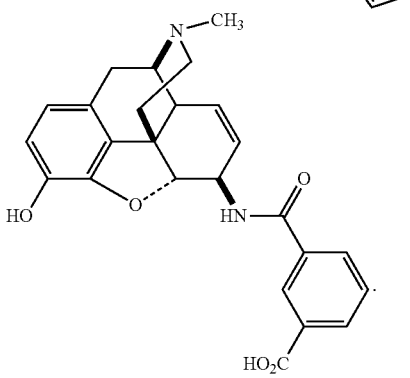

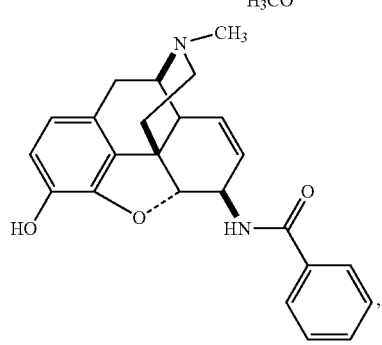

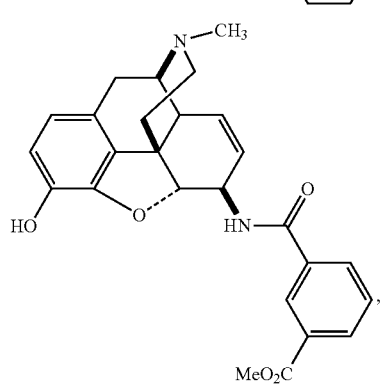

7. A pharmaceutical composition comprising: a compound of claim 1 or claim 3; and a pharmaceutically acceptable excipient or carrier.

8. A method of reducing pain in a subject in need thereof, the method comprising: administering to a subject suffering from pain an effective amount of a compound as set forth in claim 1 or claim 3.

9. The method of claim 8, wherein the agent promotes efficient internalization of an opioid receptor.

10. The method of claim 8, wherein the method is for treating pain in the periphery and the agent has a constant charge at physiological pH.

11. A method of treating an addiction in a subject, the method comprising: administering to a subject suffering from an addiction an effective amount of a compound as set forth in claim 1 or claim 3.

12. The method of claim 11, wherein the compound is an opioid receptor antagonist.

13. The method of claim 11, wherein the addiction is a substance addiction.

14. The method of claim 13, wherein the substance addiction is selected from the group consisting of a narcotic addiction, alcohol addiction, and nicotine addiction.

15. The method of claim 11, wherein the addiction is a gambling addiction.

\* \* \* \* \*